(12) United States Patent
Botyanszki et al.

(10) Patent No.: US 7,141,680 B2
(45) Date of Patent: Nov. 28, 2006

(54) AROMATIC COMPOUNDS POSSESSING ANTIFUNGAL OR ANTIBACTERIAL ACTIVITY

(75) Inventors: Janos Botyanszki, Fremont, CA (US); Dong-Fang Shi, Fremont, CA (US); Christopher Don Roberts, Belmont, CA (US); Mikail Hakan Gezginci, Foster City, CA (US); Stephen Corey Valdez, San Francisco, CA (US); Sherwin Sattarzadeh, San Francisco, CA (US)

(73) Assignee: Genelabs Technologies, Inc., Redwood City ( * ) Notice: Subject to any disclaimer, the term of this patent is extended or adjusted under 35 U.S.C. 154(b) by 357 days.

(21) Appl. No.: 10/667,085

(22) Filed: Sep. 18, 2003

(65) Prior Publication Data

US 2004/0063645 A1 Apr. 1, 2004

Related U.S. Application Data

(60) Provisional application No. 60/412,410, filed on Sep. 20, 2002.

(51) Int. Cl.
*C07D 209/14* (2006.01)
*C07D 233/48* (2006.01)
*A01N 43/38* (2006.01)
*A01N 43/54* (2006.01)

(52) U.S. Cl. ............... 548/492; 548/313.1; 548/312.1; 548/331.5; 548/348.1; 548/350.1; 514/419; 514/414; 564/230

(58) Field of Classification Search ............... 548/492, 548/313.1, 312.1, 331.5, 348.1, 350.1; 514/419; 514/414; 564/230
See application file for complete search history.

(56) References Cited

U.S. PATENT DOCUMENTS 6,548,532 B1 4/2003 Dalko et al.
6,849,713 B1 2/2005 Zhang et al.
6,906,103 B1 6/2005 Zhang et al.

FOREIGN PATENT DOCUMENTS

WO WO 98/21202 5/1998
WO WO 99/50266 10/1999
WO WO 01/96313 12/2001

OTHER PUBLICATIONS

Bally, Christian, et al., Sequence-Specific DNA Minor Groove Binders. Design and Synthesis of Netropsin and Distamycin Analogues, *Bioconjugate Chemistry*, 9(5), (Sep./Oct. 1998), pp. 513-538.
Filipowsky, Mark E., et al., Linked Lexitropsins and the in Vitro Inhibition of HIV-1 Reverse Transcriptase RNA-Directed DNA Polymerization: A Novel Induced-Fit of 3.5 m-Pyridyl Bisdistamycin to Enzyme-Associated Template-Primer, *Biochemistry*, (Dec. 3, 1996), 35(40), pp. 15399-15410.
Kissinger et al., Molecular Recognition between Oligopeptides and Nucleic Acids: DNA Binding Specificity of a Series of Bis Netropsin Analogues Deduced from Footprinting Analysis., *Chem. Res. Toxicol.*, 3(2), (1990), pp. 162-168.
Neamati, Nouri et al., Highly Potent Synthetic Polyamides, Bisdistamycins, and Lexitropsins as Inhibitors and Human Immunodeficiently Virus Type 1 Integrase, *Molecular Pharmacology*, 54, (1998), pp. 280-290.
Wang, Z., et al., Effects of Bifunctional Netropsin-related Minor Groove-binding Ligands on Mammalian Type I DNA Topoisomerase., *Biochem. Pharmacol.*, 53, (1997), pp. 309-316.
Khalaf, Abedawn I., et al., The Synthesis of Some Head to Head Linked DNA Minor Groove Binders, *Tetrahedron*, 56(29), (2000), pp. 5225-5239.
Baraldi, Pier G., et al., Synthesis and antitumor Activity of New Benzoheterocyclic Derivatives of Distamycin A, *J. Med. Chem.*, 43(14), (2000), pp. 2675-2684.
Boger, Dale L., et al., Total Synthesis of Distamycin A and 2640 Analogues: A Solution-Phase Combinatorial Approach to the Discovery of New, Bioactive DNA Binding Agents and Development of a Rapid, High-Throughput Screen for Determining Relative DNA Binding Affinity or DNA Binding Sequence Selectivity, *J. Am. Chem. Soc.*, 122(27), (2000), pp. 6382-6394.
Balzarini, J., et al., Inhibitory Activity of Diarylamidine Derivatives on Murine Leukemia L1210 Cell Growth, *Invest. New Drugs*, 1(2), (1983), pp. 103-115.
Anne, Jozef, et al., Antifungal and Antibacterial Activities of Diarylamidine Derivatives, *Antimicrobial Agents and Chemotherapy*, 18(2), (1980), pp. 231-239.
De Clercq, E. et al., Diaryl Amidine Derivatives as Oncornaviral DNA Polymerase Inhibitors, *J. Med. Chem.*, 23(7), (1980), pp. 787-795.

*Primary Examiner*—Kamal A. Saeed
*Assistant Examiner*—Yong Chu
(74) *Attorney, Agent, or Firm*—Junrui Yang

(57) ABSTRACT

The present invention provides novel compounds possessing antibacterial, and/or antifungal activities. Pharmaceutical compositions containing these compounds, methods of making and methods for using these compounds are also provided.

9 Claims, No Drawings

AROMATIC COMPOUNDS POSSESSING ANTIFUNGAL OR ANTIBACTERIAL ACTIVITY

CROSS-REFERENCE TO RELATED APPLICATIONS

This application claims the benefit under 35 U.S.C. 119(e) of U.S. Provisional Application Ser. No. 60/412,410, which was filed on Sep. 20, 2002, the disclosure of which is incorporated herein in its entirety.

BACKGROUND OF THE INVENTION

1. Field of Invention

The present invention provides novel compounds possessing one or more of the following activities: antibacterial, antifungal, antiviral, anticancer, and antiparasitic activity. Pharmaceutical compositions containing these compounds, methods of making and methods for using these compounds are also provided.

2. State of the Art

Invasive fungal infections are a serious cause of mortality in many patients including an increasing number of immunocompromised patients. Few treatment choices exist and first-line therapies have significant limitations due to safety problem and lack of broad spectrum activity. The growing prevalence of fungal strains resistant to currently available therapies presents an additional clinical challenge. Meanwhile, the rapid emergence of bacterial infections resistant to treatment with standard antibiotics constitutes another serious public health threat. Novel antibacterial and antifungal agents are needed which are less prone to give rise to resistance or are directed towards novel biological targets.

Using small molecule drugs to cause cell death through DNA interaction is a proven approach in treating cancer and microbial infections. Smaller compounds are more likely to have suitable cellular uptake and pharmacokinetic properties compared to higher molecular weight compounds. The binding of the antibacterial netropsin and distamycin to AT-rich sequences in the minor groove of double stranded DNA is a well studied phenomenon. Because such binding can be used to regulate DNA expression, e.g., by blocking and/or displacement of regulatory proteins, or by inhibiting the activity of enzymes acting on DNA, such as reverse transcriptase or topoisomerase, optimization of this binding has been the subject of numerous recent studies.

As described in a review by Bailly and Chaires (*Bioconj. Chem.* 9(5):513–38, 1998), the pyrrolecarboxamide unit in netropsin and distamycin is actually about 20% longer than required to perfectly match the corresponding base pair sequence in the minor groove. Accordingly, in oligomeric analogs having multiple binding moieties, successive binding moieties can become out of phase with the base pairs of the minor groove. Several studies have therefore been directed to dimers of netropsin or distamycin containing different linkers, in order to improve binding to longer target sequences. In these reports, effectiveness of various netropsin or distamycin dimers was determined, for example, in the inhibition of transcription by HIV-1 reverse transcriptase (M. Filipowsky et al, *Biochemistry* 35:15397–410, 1996), inhibition of mammalian DNA topoisomerase I (Z. Wang et al., *Biochem. Pharmacol.* 53:309–16, 1997), or inhibition of HIV 1 integrase (N. Neamati et al., *Mol. Pharmacol.* 54:280–90, 1998). Preferred linkers in these studies included p-phenylene, trans-vinyl, cyclopropyl, 3,5-pyridyl, and six- and eight-carbon aliphatic chains. Several of these linkers restrict rotation around the linking group, thus reducing the extent of purely monodentate binding (e.g. by only one netropsin moiety; see Bailly) which can occur with flexible linkers. However, Kissinger et al. (*Chem. Res. Toxicol.* 3(2): 162–8, 1990) reported that aryl-linked groups had reduced DNA binding affinity compared to alkyl and alkylene linkers, and Neamati et al. (cited above) reported that the trans-vinyl linked compound was many times more potent (in inhibiting HIV-1 integrase) than the "more rigid" cyclobutanyl and norbornyl linkers. It was suggested in Wang and in Bailly that, for certain applications, the more rigid linkers (cyclopropyl and p-phenylene) may not allow for optimal simultaneous (bidentate) binding of the two netropsin moieties flanking the linker. Therefore, it would be desirable to provide linkers which reduce monodentate binding but which provide suitable geometries for bidentate binding. Nevertheless, there is much confusion as to what constitutes linkers of choice such that highly effective antibacterial, antifungal and/or anticancer compounds are formed. In light of the foregoing discussion, there is a need to develop new compounds to treat diseases such as cancer, bacterial, fungal and viral infection. The compounds of the present invention fulfill this need.

SUMMARY OF THE INVENTION

The present invention provides novel compounds possessing one or more of the following activities: antibacterial, antifungal, antiviral, anticancer, and antiparasitic activity. Specifically, the compounds of the present invention are represented in Formula (I) below

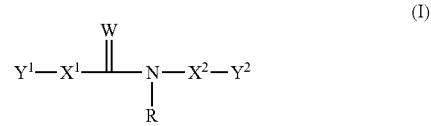

wherein:

$X^1$ and $X^2$ are independently arylene, substituted arylene, heteroarylene, or substituted heteroarylene provided that $X^1$ and $X^2$ are not both pyrrolene;

$Y^1$ is selected from the group consisting of the following moieties:

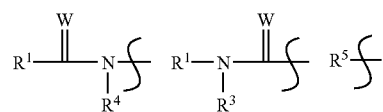

$Y^2$ is selected from the group consisting of the following moieties:

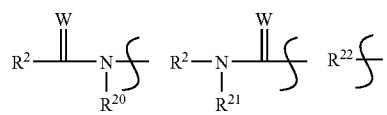

W is O or S;

R is hydrogen or alkyl;

$R^1$, $R^2$, $R^5$ and $R^{22}$ are independently selected from the group consisting of the following moieties:

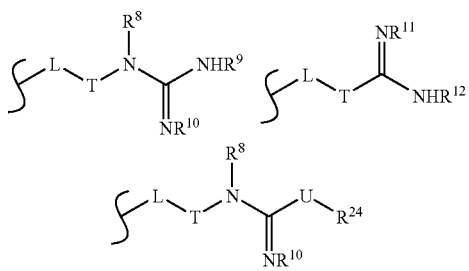

L is selected from the group consisting of a bond, alkylene, cycloalkylene, heterocyclene, alkylene-cycloalkylene-alkylene, alkylene-cycloalkylene, cycloalkylene-alkylene, arylene, alkylene-arylene-alkylene, alkylene-arylene, arylene-alkylene, heteroarylene, alkylene-heteroarylene-alkylene, alkylene-heteroarylene, and heteroarylene-alkylene;

T is O or a bond such that when both T is a bond and L is a bond, T and L together is a bond;

U is O, S or a bond;

$R^3$ is hydrogen or alkyl or $R^3$ and $R^1$ together with the atoms to which they are attached form a heterocyclic or heteroaryl ring;

$R^{21}$ is hydrogen or alkyl or $R^{21}$ and $R^2$ together with the atoms to which they are attached form a heterocyclic or heteroaryl ring;

$R^4$ and $R^{20}$ are independently hydrogen or alkyl;

$R^8$ is hydrogen or alkyl;

$R^9$, $R^{10}$, $R^{11}$ and $R^{12}$ are independently hydrogen, hydroxyl, alkyl, substituted alkyl, alkenyl, substituted alkenyl, cycloalkyl, cycloalkenyl or heterocyclic, or $R^9$ and $R^{10}$ together with the atoms to which they are attached form a heterocyclic or heteroaryl ring, or $R^{11}$ and $R^{12}$ together with the atoms to which they are attached form a heterocyclic or heteroaryl ring; and $R^{24}$ is alkyl, substituted alkyl, or heteroaryl;

and acid addition salts thereof;

provide that the compound of Formula (I) is not one of the following compounds:

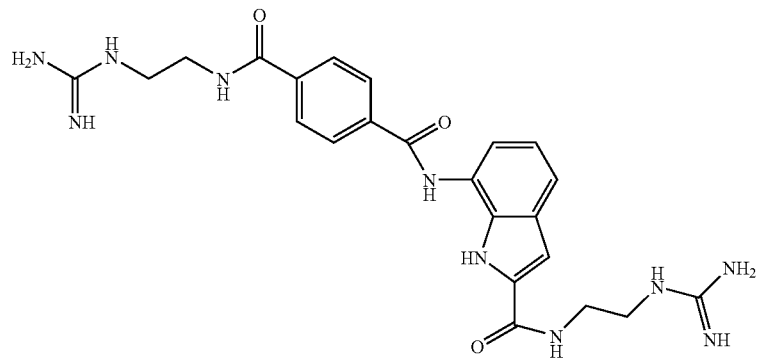

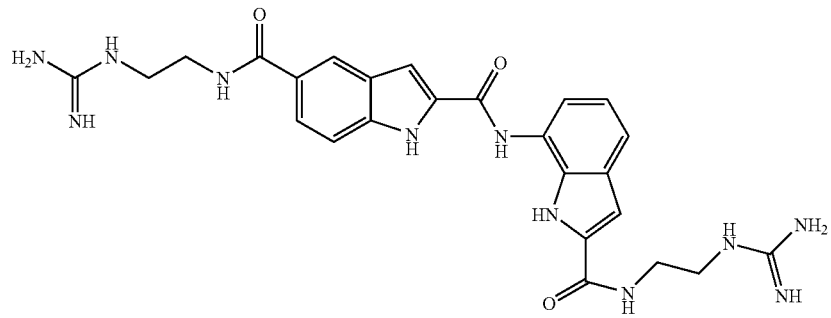

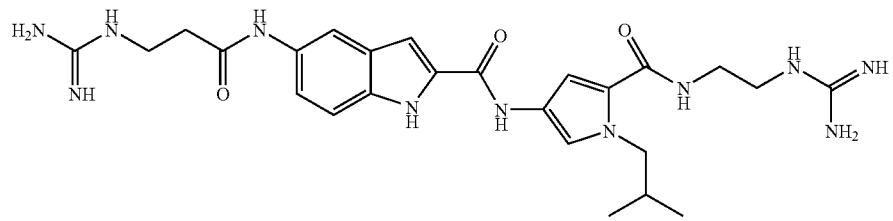

In another aspect, compounds of the present invention are represented by the following structures:

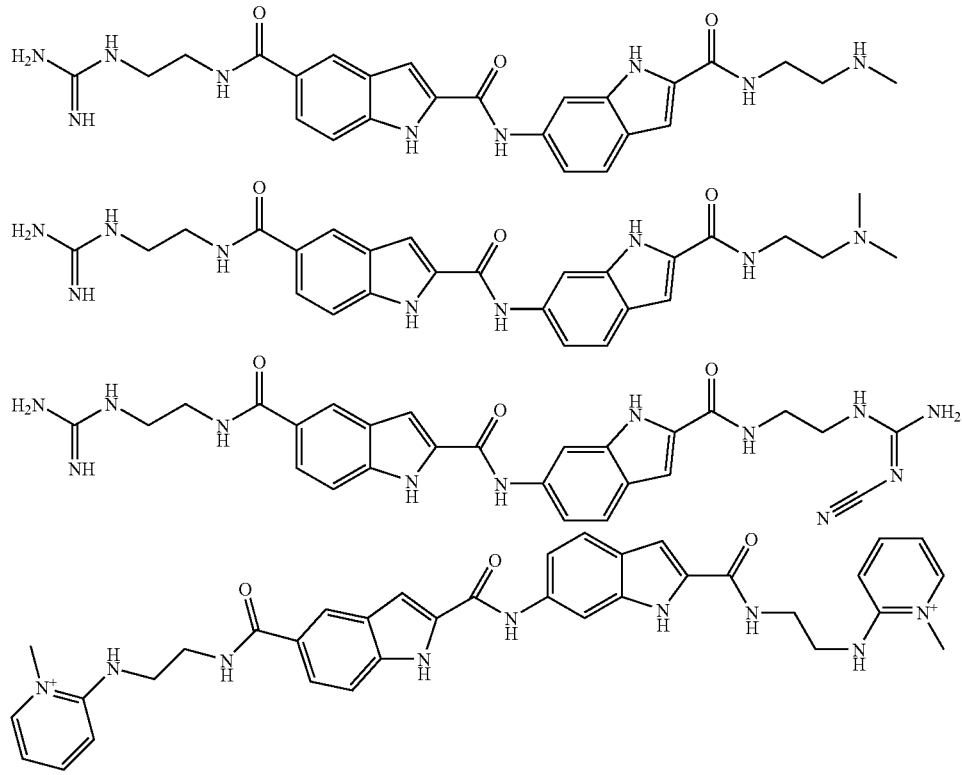

In another aspect, this invention is directed to a method of treating bacterial, fungal, viral, or parasital infection, or cancer, which method comprises administration of a therapeutically effective amount of a compound or mixture of the compounds of Formula (I) and compounds disclosed in the present invention or a pharmaceutically acceptable acid addition salt thereof.

In another aspect, this invention is directed to pharmaceutical compositions containing a therapeutically effective amount of a compound or mixture of the compounds of Formula (I) and compounds disclosed in the present invention or pharmaceutically acceptable acid addition salts thereof and a pharmaceutically acceptable excipient.

DETAILED DESCRIPTION OF THE INVENTION

This invention is directed to novel compounds possessing one or more of the following activities: antibacterial, antifungal, antiviral, anticancer, and antiparasitic activity.

Unless otherwise stated, the following terms used in the specification and claims have the meanings given below:

"Alkyl" means a linear or branched saturated monovalent hydrocarbon radical of one to ten carbon atoms, preferably one to six carbon atoms, e.g., methyl, ethyl, propyl, 2-propyl, n-butyl, iso-butyl, tert-butyl, pentyl, and the like.

"Substituted alkyl" means a linear or branched saturated monovalent hydrocarbon radical of one to ten carbon atoms, preferably one to six carbon atoms, which is substituted with 1 to 5 group(s), preferably 1 or 2 group(s), selected from the group consisting of hydroxy, alkoxy, acyl, acylamino, halo, thio, thioalkyoxy, amido, amino, mono or disubstituted amino, carboxy, amidino, guanidino, amidoxime, sulfonylamino, cycloalkyl, heterocyclic, aryl, substituted aryl, heteroaryl, substituted heteroaryl and —$NRSO_2NR'R''$ (where R is hydrogen or alkyl and R' and R'' are independently hydrogen, alkyl, haloalkyl, aryl, substituted aryl, heteroaryl, and substituted heteroaryl).

"Alkylene" means a linear or branched saturated divalent hydrocarbon radical of one to six carbon atoms, e.g., methylene, ethylene, 2,2-dimethylethylene, propylene, 2-methylpropylene, butylene, pentylene, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Substituted alkenyl" means an alkenyl radical, as defined herein, that is substituted with 1 to 3 group(s), preferably 1 or 2 group(s) selected from the group consisting of hydroxy, alkoxy, acyl, acylamino, halo, amino, mono or disubstituted amino, carboxy, amidino, guanidino, sulfonylamino, heterocyclic, aryl, substituted aryl, heteroaryl, substituted heteroaryl and —$NRSO_2NR'R''$ (where R is hydrogen or alkyl and R' and R'' are independently hydrogen, alkyl, haloalkyl, aryl, substituted aryl, heteroaryl, and substituted heteroaryl).

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Cycloalkyl" means a saturated monovalent cyclic hydrocarbon radical of three to six ring carbons, e.g., cyclopropyl, cyclopentyl, cyclohexyl, and the like.

"Substituted cycloalkyl" means a cycloalkyl radical as defined herein that is substituted independently with one, two or three substituents, preferably one or two substituents, selected from alkyl, alkoxy, substituted alkyl, acyl, acylamino, sulfonylamino, halo, nitro, cyano, amino, monosubstituted or disubstituted amino and —NRSO$_2$NR'R" (where R is hydrogen or alkyl and R' and R" are independently hydrogen, alkyl, haloalkyl, aryl, substituted aryl, heteroaryl, and substituted heteroaryl).

"Cycloalkylene" means a saturated divalent cyclic hydrocarbon radical of three to six ring carbons, e.g., cyclopropylene, cyclopentylene, cyclohexylene, and the like.

"Sulfonylamino" means a radical —NRSO$_2$R' where R is hydrogen or alkyl and R' is alkyl, substituted alkyl, amino, monosubstituted amino, disubstituted amino, aryl, substituted aryl, aralkyl, substituted aralkyl, heteroaryl, substituted heteroaryl, heteroaralkyl, and substituted heteroaralkyl, e.g., methylsulfonylamino, benzylsulfonylamino, N-methylaminosulfonylamino, and the like.

"Alkoxy "means a radical —OR where R is an alkyl as defined above e.g., methoxy, ethoxy, propoxy, butoxy and the like.

"Acyl" means a radical —C(O)R, where R is hydrogen, alkyl, substituted alkyl, aryl, substituted aryl, aralkyl, substituted aralkyl, heteroaryl, substituted heteroaryl, heteroaralkyl, substituted heteroaralkyl, heterocyclic, and heterocyclicalkyl group as defined herein. Representative examples include, but are not limited to formyl, acetyl, benzoyl, benzylcarbonyl, glycyl and the like.

"Acylamino" means a radical —NR'C(O)R, where R' is hydrogen or alkyl, and R is hydrogen, alkyl, substituted alkyl, aryl, substituted aryl, aralkyl, substituted aralkyl, heteroaryl, substituted heteroaryl, heteroaralkyl, substituted heteroaralkyl, heterocyclic, and heterocyclicalkyl group as defined herein. Representative examples include, but are not limited to formylamino, acetylamino, benzoylamino, benzylcarbonylamino, and the like.

"Monosubstituted amino" means a radical —NHR where R represents an alkyl, acyl, aryl, substituted aryl, aralkyl, substituted aralkyl, heteroaryl, substituted heteroaryl, heteroaralkyl, substituted heteroaralkyl, heterocyclic, and heterocyclicalkyl group as defined herein. Representative examples include, but are not limited to methylamino, ethylamino, phenylamino, benzylamino, and the like.

"Disubstituted amino" means a radical —NRR' where R and R' are independently selected from the group consisting of alkyl, acyl, aryl, substituted aryl, aralkyl, substituted aralkyl, heteroaryl, substituted heteroaryl, heteroaralkyl, substituted heteroaralkyl, heterocyclic, and heterocyclicalkyl group as defined herein. Representative examples include, but are not limited to dimethylamino, diethylamino, ethylmethylamino, diphenylamino, dibenzylamino, and the like.

"Halo" means fluoro, chloro, bromo, or iodo, preferably fluoro and chloro.

"Haloalkyl" means alkyl substituted with one or more same or different halo atoms, e.g., —CH$_2$Cl, —CF$_3$, —CH$_2$CF$_3$, —CH$_2$CCl$_3$, and the like.

"Aryl" means a monovalent monocyclic, bicyclic or tricyclic aromatic hydrocarbon radical of 6 to 14 ring atoms e.g., phenyl, naphthyl, anthryl and the like.

"Substituted aryl" means an aryl ring as defined above which is substituted independently with one, two or three substituents, preferably one or two substituents, selected from alkyl, alkoxy, aryloxy, substituted alkyl, acyl, acylamino, sulfonylamino, halo, nitro, cyano, amino, monosubstituted or disubstituted amino and —NRSO$_2$NR'R" (where R is hydrogen or alkyl and R' and R" are independently hydrogen, alkyl, haloalkyl, aryl, substituted aryl, heteroaryl, and substituted heteroaryl).

"Arylene" means a divalent monocyclic, bicyclic or tricyclic aromatic hydrocarbon radical of 6 to 14 ring atoms e.g., phenylene, naphthylene, anthrylene, and the like.

"Heteroaryl" means a monovalent monocyclic, bicyclic or tricyclic radical of 5 to 12 ring atoms having at least one aromatic ring containing one, two, three or four ring heteroatoms selected from N, O, or S, the remaining ring atoms being C, with the understanding that the attachment point of the heteroaryl radical will be on an aromatic ring. More specifically the term heteroaryl includes, but is not limited to, pyridyl, furanyl, thienyl, thiazolyl, tetrazolyl, isothiazolyl, triazolyl, imidazolyl, isoxazolyl, pyrrolyl, pyrazolyl, pyrimidinyl, benzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl.

"Substituted heteroaryl" means a heteroaryl ring as defined above which is substituted independently with one, two or three substituents, preferably one or two substituents, selected from alkyl, alkoxy, aryloxy, substituted alkyl, acyl, acylamino, sulfonylamino, halo, nitro, cyano, amino, monosubstituted or disubstituted amino and —NRSO$_2$NR'R" (where R is hydrogen or alkyl and R' and R" are independently hydrogen, alkyl, haloalkyl, aryl, substituted aryl, heteroaryl, and substituted heteroaryl).

"Heteroarylene" means a divalent monocyclic, bicyclic or tricyclic radical of 5 to 12 ring atoms having at least one aromatic ring containing one, two, three or four ring heteroatoms selected from N, O, or S, the remaining ring atoms being C, with the understanding that the attachment point of the heteroaryl radical will be on an aromatic ring. More specifically the term heteroarylene includes, but is not limited to, pyridylene, furanylene, thienylene, thiazolylene, tetrazolylene, isothiazolylene, triazolylene, imidazolylene, isoxazolylene, pyrrolylene, pyrazolylene, pyrimidinylene, benzofuranylene, isobenzofuranylene, benzothiazolylene, benzoisothiazolylene, benzotriazolylene, indolylene, isoindolylene, benzoxazolylene, quinolylene, tetrahydroquinolinylene, isoquinolylene, benzimidazolylene, benzisoxazolylene or benzothienylene.

"Aralkyl", "heteroaralkyl", "substituted aralkyl", "substituted heteroaralkyl", means a radical —R$^a$R$^b$ where R$^a$'s an alkylene group and R$^b$ is a aryl or substituted aryl, heteroaryl or substituted heteroaryl group as defined herein, e.g., benzyl, pyridin-3-ylmethyl, imidazolylethyl, pyridinylethyl, 3-(benzofuran-2-yl)propyl, and the like.

"Heterocyclic" means a saturated non-aromatic cyclic radical of 5 to 8 ring atoms in which one or two ring atoms are heteroatoms selected from NR (where R is independently hydrogen, alkyl, or heteroalkyl), O, or S(O)$_n$ (where n is an integer from 0 to 2), the remaining ring atoms being C, where one or two C atoms may optionally be replaced by a carbonyl group. The heterocyclic ring may be optionally substituted independently with one, two, or three substituents selected from alkyl, alkoxy, substituted alkyl, acyl, acylamino, sulfonylamino, halo, nitro, cyano, amino, monosubstituted or disubstituted amino and —NRSO$_2$NR'R" (where R is hydrogen or alkyl and R' and R" are independently hydrogen, alkyl, haloalkyl, aryl, substituted aryl, heteroaryl, and substituted heteroaryl). More specifically the term heterocyclic includes, but is not limited to, tetrahydropyranyl, 2,2-dimethyl-1,3-dioxolane, piperidino, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, pyrrolinyl, imidazolinyl, and the derivatives thereof.

"Heterocyclene" means a saturated divalent non-aromatic cyclic radical of 5 to 8 ring atoms in which one or two ring atoms are heteroatoms selected from NR (where R is independently hydrogen, alkyl, or heteroalkyl), O, or $S(O)_n$ (where n is an integer from 0 to 2), the remaining ring atoms being C, where one or two C atoms may optionally be replaced by a carbonyl group.

"Heterocyclicalkyl" means a radical —$R^aR^b$ where $R^a$ is an alkylene group and $R^b$ is a heterocyclic group as defined herein, e.g., tetrahydropyran-2-ylmethyl, 4-methylpiperazin-1-ylethyl, 3-piperidinylmethyl, 2,2-dimethyl-1,3-dioxoxolan-4-ylmethyl, benzyl, and the like.

"Optional" or "optionally" means that the subsequently described event or circumstance may but need not occur, and that the description includes instances where the event or circumstance occurs and instances in which it does not. For example, "heterocyclic group optionally mono- or di-substituted with an alkyl group" means that the alkyl may but need not be present, and the description includes situations where the heterocyclic group is mono- or disubstituted with an alkyl group and situations where the heterocyclic group is not substituted with the alkyl group.

"Hydroxy or amino protecting group" refers to those organic groups intended to protect oxygen and nitrogen atoms against undesirable reactions during synthetic procedures. Suitable oxygen and nitrogen protecting groups are well known in the art e.g., trimethylsilyl, dimethyl-tert-butylsilyl, benzyl, benzyloxy-carbonyl (CBZ), tert-butoxycarbonyl (Boc), trifluoroacetyl, 2-trimethylsilylethanesulfonyl (SES), and the like. Others can be found in the book by T. W. Greene and G. M. Wuts, *Protecting Groups in Organic Synthesis*, Third Edition, Wiley, New York, 1999, and references cited therein.

Amino acid refers to any of the naturally occurring amino acids, as well as synthetic analogs (e.g., the naturally occurring D-stereoisomers of amino acids, such as D-threonine) and derivatives thereof. α-Amino acids comprise a carbon atom to which is bonded an amino group, a carboxyl group, a hydrogen atom, and a distinctive group referred to as a "side chain". The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine and tryptophan), substituted arylalkyl (e.g., as in tyrosine), and heteroarylalkyl (e.g., as in histidine). Unnatural amino acids are also known in the art, as set forth in, for example, Williams (ed.), Synthesis of Optically Active .alpha.-Amino Acids, Pergamon Press (1989); Evans et al., J. Amer. Chem. Soc., 112:4011–4030 (1990); Pu et al., J. Amer. Chem. Soc., 56:1280–1283 (1991); Williams et al., J. Amer. Chem. Soc., 113:9276–9286 (1991); and all references cited therein. The present invention includes the side chains of unnatural amino acids as well.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory (D–) or levorotatory (L–) (i.e., as (+) or (–)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual L- or D-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", $4^{th}$ edition J. March, John Wiley and Sons, New York, 1992).

A "pharmaceutically acceptable excipient" means an excipient that is useful in preparing a pharmaceutical composition that is generally safe, relatively non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

"Pharmaceutically acceptable acid addition salts" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"An acid addition salt" or "acid addition salts" refers to those salts which are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Groups which form pharmaceutically acceptable acid addition salts include amines, hydrazines, amidines, guanidines, substituted aryliheteroaryl and substituted alkyl groups that carry at least a heteroatom bearing substitutent, preferably a nitrogen bearing substituent such as amino, guanidine, amidino and the like.

Amine groups are represented by the formula —NR'R" where R' and R" are independently hydrogen, alkyl, substituted alkyl, alkenyl, substituted alkenyl, aryl, substituted aryl, cycloalkyl, substituted cycloalkyl, heterocyclic, heteroaryl, substituted heteroaryl, and where R' and R", together with the nitrogen to which they are attached, form a heterocyclic or heteroaryl group.

Hydrazines are represented by the formula —NHNR'R" where R' and R" are independently hydrogen, alkyl, substituted alkyl, alkenyl, substituted alkenyl, aryl, substituted aryl, cycloalkyl, substituted cycloalkyl, heterocyclic, heteroaryl, substituted heteroaryl, and where R' and R", together with the nitrogen to which they are attached, form a heterocyclic or heteroaryl group.

Amidino groups are represented by the formula —C(=NR') NHR" where R' and R" are independently hydrogen, alkyl, substituted alkyl, alkenyl, substituted alkenyl, aryl, substituted aryl, cycloalkyl, substituted cycloalkyl, heterocyclic, heteroaryl, substituted heteroaryl, and where R' and R", together with the nitrogen to which they are attached, form a heterocyclic or heteroaryl group.

Guanidino groups is represented by the formula —NHC(=NR')NHR" where R' and R" are independently hydrogen, alkyl, substituted alkyl, alkenyl, substituted alkenyl, aryl, substituted aryl, cycloalkyl, substituted cycloalkyl, heterocyclic, heteroaryl, substituted heteroaryl, and where R' and R", together with the nitrogen to which they are attached form a heterocyclic or heteroaryl group.

Compounds of the present invention may act as a prodrug. Prodrug means any compound which releases an active parent drug according to Formula (I) as a results of conversion by metabolic processes in vivo when such prodrug is administered to a mammalian subject. The prodrug itself may be active. Prodrugs of a compound of Formula (I) are prepared by modifying functional groups present in the compound of Formula (I) in such a way that the modifications may be cleaved in vivo to release the active parent compound. Prodrugs include compounds of Formula (I) wherein a hydroxy, amino, or sulfhydryl group in compound (I) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylamino-carbonyl) of hydroxy functional groups in compounds of Formula (I), and the like.

"Treating" or "treatment" of a disease includes:
(1) preventing the disease, i.e. causing the clinical symptoms of the disease not to develop in a mammal that may be exposed to or predisposed to the disease but does not yet experience or display symptoms of the disease,
(2) inhibiting the disease, i.e., arresting or reducing the development of the disease or its clinical symptoms, or
(3) relieving the disease, i.e., causing regression of the disease or its clinical symptoms.

A "therapeutically effective amount" means the amount of a compound that, when administered to a mammal for treating a disease, is sufficient to effect treatment for the disease. The "therapeutically effective amount" will vary depending on the compound, the disease and its severity and the age, weight, etc., of the mammal to be treated.

"Antifungal", "antibacterial", "antiviral" or "antiparasitic" means that the fungus, bacterial, virus or paracite, respectively, is killed, or its growth is inhibited or stopped.

"Antitumor" means the compound has the property of inhibiting the growth of tumor cells.

"Anticancer" means the compound has the property of inhibiting the growth of cancer cells.

"Bacteriostatic" means the compound has the property of inhibiting bacterial or fungal multiplication, wherein multiplication resumes upon removal of the active compound. For a bacteriostatic compound, its minimum bacteriocidal concentration (MBC) is greater than 4× its minimum inhibitory concentration (MIC).

"Bacteriocidal" or "fungicidal" means that the compound has the property of killing bacteria or fungi. Bacteriocidal/fungicidal action differs from bacteriostasis or fungistasis only in being irreversible. For example, the "killed" organism can no longer reproduce, even after being removed form contact with the active compound. In some cases, the active compound causes lysis of the bacterial or fungal cell; in other cases the bacterial or fungal cell remains intact and may continue to be metabolically active. A bacteriocidal compound exhibits a MBC that is less than 4× its MIC. Similarly, a fungicidal compound exhibits a minimum fungicidal concentration (MFC) that is less than 4× its MIC.

"Minimum inhibitory concentration" or "MIC" refers to the minimum concentration of a compound necessary to completely inhibit growth of the organism tested. Compounds of this invention having an MIC of 1 mM or less are active in the assays described in the examples below. Preferably, compounds have an MIC of 500 μM or less, more preferably an MIC of 50 μM or less, and even more preferably an MIC of 10 μM or less.

"dsDNA" means double stranded DNA.

EMBODIMENTS OF THE INVENTION

While the broad definition of this invention is set forth in the Summary of the Invention, certain compounds of the present invention are preferred.

A preferred group of compounds of Formula (I) is that wherein $X^1$ and $X^2$ are independently selected from a group consisting of the following moieties:

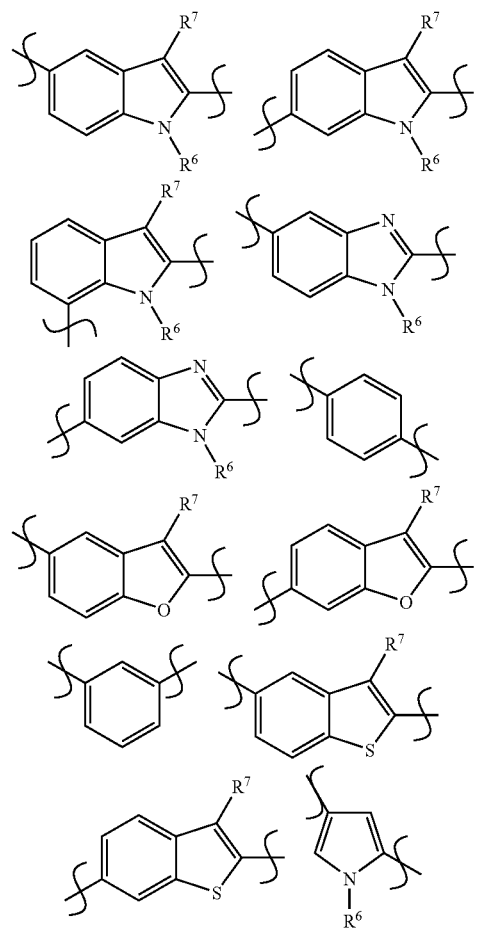

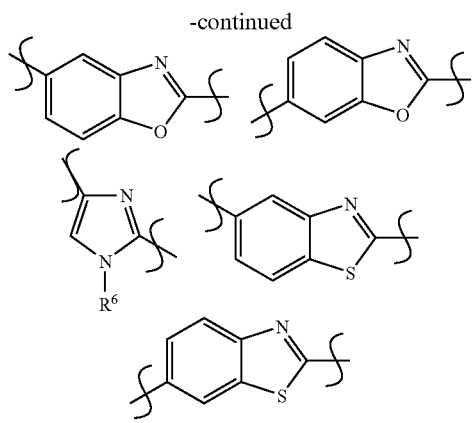

wherein

R[6] is hydrogen, alkyl or substituted alkyl; and

R[7] is hydrogen, halo, alkyl, substituted alkyl, aryl, substituted aryl, heteroaryl, substituted heteroaryl, sulfonyl, hydroxy, alkoxy or acyl.

Another preferred group of compounds of Formula (I) is that wherein W is O;

Another preferred group of compounds is that wherein at least one of X[1] and X[2] is selected from the group consisting of the following moieties:

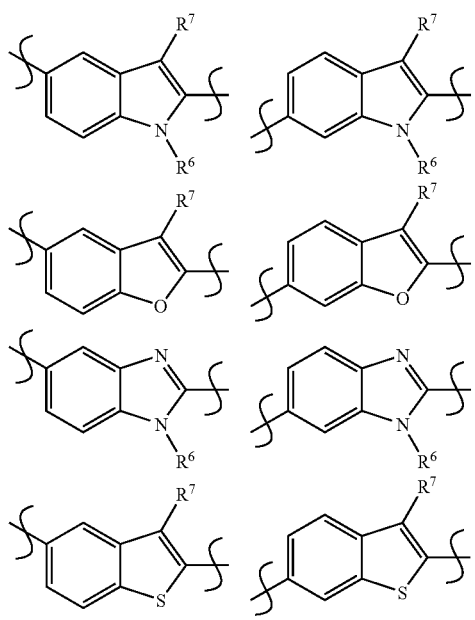

wherein R[6] and R[7] are as defined above.

Another preferred group of compounds is that wherein R[1] and R[2] are independently selected from the group consisting of the following moieties:

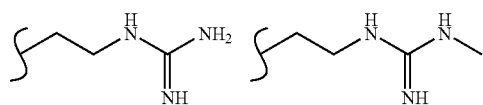

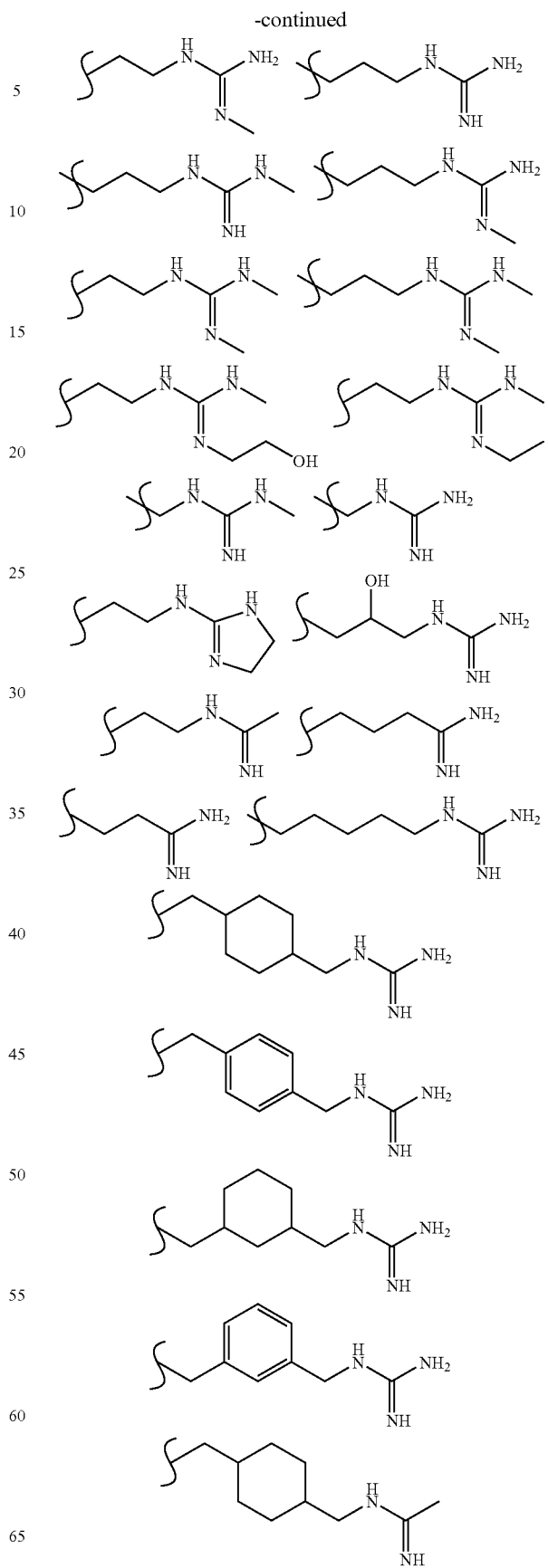

-continued
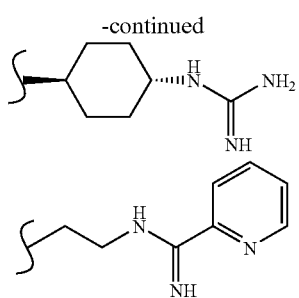
Another preferred group of compounds is that wherein at least one of $X^1$ and $X^2$ is selected from the group consisting of the following moieties:
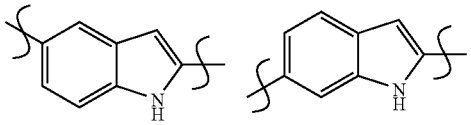
Compounds and acid addition salts thereof included within the scope of this invention include, for example, those set forth below:

| No. | R | Name |
|---|---|---|
| 9 | 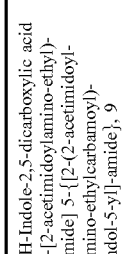 | 1H-Indole-2,5-dicarboxylic acid 2-[2-acetimidoylamino-ethyl)-amide] 5-{[2-(2-acetimidoyl-amino-ethylcarbamoyl)-indol-5-yl]-amide}, 9 |
| 10 | 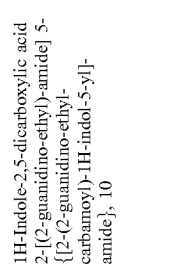 | 1H-Indole-2,5-dicarboxylic acid 2-[(2-guanidino-ethyl)-amide] 5-{[2-(2-guanidino-ethyl-carbamoyl)-1H-indol-5-yl]-amide}, 10 |
| 18 | 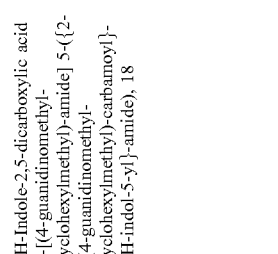 | 1H-Indole-2,5-dicarboxylic acid 2-[(4-guanidinomethyl-cyclohexylmethyl)-amide] 5-({2-[(4-guanidinomethyl-cyclohexylmethyl)-carbamoyl]-1H-indol-5-yl}-amide), 18 |
| 19 | 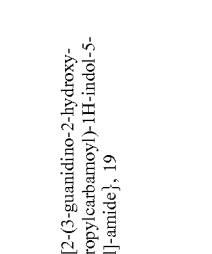 | {[2-(3-guanidino-2-hydroxy-propylcarbamoyl)-1H-indol-5-yl]-amide}, 19 |

| No. | R | Name |
|---|---|---|
| 20 | | 1H-Indole-2,5-dicarboxylic acid 2-[(5-guanidino-pentyl)-amide] 5-{[2-(5-guanidino-pentylcarbamoyl)-1H-indol-5-yl]-amide}, 20 |
| 21 | | 1H-Indole-2,5-dicarboxylic acid 2-[(4-guanidino-cyclohexyl)-amide] 5-{[2-(4-guanidino-cyclohexylcarbamoyl)-1H-indol-5-yl]-amide}, 21 |
| 22 | | 1H-Indole-2,5-dicarboxylic acid 2-(4-guanidinomethyl-benzylamide) 5-{[2-(4-guanidinomethyl-benzylcarbamoyl)-1H-indol-5-yl]-amide}, 22 |
| 23 | | 1H-Indole-2,5-dicarboxylic acid 2-[[4-(acetimidoylamino-methyl)-cyclohexylmethyl]-amide} 5-[(2-{[4-(acetimidoylamino-methyl)-cyclohexylmethyl]-carbamoyl}-1H-indol-5-yl)-amide], 23 |

-continued

| No. | R | Name |
|---|---|---|
| 24 | | 1H-Indole-2,5-dicarboxylic acid 2-[(3-guanidinomethyl-cyclohexylmethyl)-amide] 5-({2-[(3-guanidinomethyl)-cyclohexylmethyl)-carbamoyl]-1H-indol-5-yl}-amide), 24 |
| 25 | | 1H-Indole-2,5-dicarboxylic acid 2-(3-guanidinomethyl-benzylamide) 5-{[2-(3-guanidino-methylbenzylcarbamoyl)-1H-indol-5-yl]-amide} |
| 29 | | 1H-Indole-2,5-dicarboxylic acid 2-[(2-guanidino-ethyl)-amide] 5-{[5-(2-guanidino-ethylcarbamoyl)-1-isobutyl-1H-pyrrol-3-yl]-amide}, 29 |
| 47 | | 1H-Indole-2,5-dicarboxylic acid 5-[(2-guanidino-ethyl)-amide] 2-{[2-(2-guanidino-ethylcarbamoyl)-1H-indol-6-yl]-amide}, 47 |

| No. | R | Name |
|---|---|---|
| 48 | | 1H-Indole-2,5-dicarboxylic acid 5-{[2-(N'-methyl-guanidino)-ethyl]-amide} 2-({2-[2-(N'-methyl-guanidino)-ethylcarbamoyl]-1H-indol-6-yl}-amide), 48 |
| 49 | | 1H-Indole-2,5-dicarboxylic acid 2-{[2-(N',N''-dimethylguanidino)ethyl]amide} 5-({2-[2-(N',N''-dimethylguanidino)ethylcarbamoyl]-1H-indol-6-yl}amide) dihydrochloride, 49 |
| 50 | | 1H-Indole-2,5-dicarboxylic acid 5-{[2-(4,5-dihydro-1H-imidazol-2-yl)amino]ethyl]amide} 2-({2-[2-(4,5-dihydro-1H-imidazol-2-yl)amino)-ethyl]carbamoyl]-1H-indol-6-yl}-amide), 50 |
| 52 | | 1H-Indole-2,5-dicarboxylic acid 2-{[2-(2-guanidinoethylcarbamoyl)-1H-indol-6-yl]amide} 5-[(3-guanidinopropyl)amide] dihydrochloride, 52 |
| 53 | | 1H-Indole-2,5-dicarboxylic acid 2-({2-[(N'-methylguanidino)ethylcarbamoyl]-1H-indol-6-yl}amide) 5-{[3-(N'-methylguanidino)propyl]amide} dihydrochloride, 53 |

| No. | R | Name |
|---|---|---|
| 54 | | 1H-Indole-2,5-dicarboxylic acid 2-({2-[(N',N''-dimethylguanidino)ethylcarbamoyl]-1H-indole-6-yl}amide) 5-{[3-(N',N''-dimethylguanidino)propyl]amide} dihydrochloride, 54 |
| 55 | | 1H-Indole-2,5-dicarboxylic acid 5-{[2-(2-(N'-methylguanidino)ethyl]amide} 2-({2-[(N'-methylguanidino)ethylcarbamoyl]-1H-indole-5-yl}amide) dihydrochloride, 55 |
| 56 | | 1H-Indole-2,5-dicarboxylic acid 2-{[2-(N',N''-dimethylguanidino)ethylcarbamoyl]-5-[(2-(N',N''-dimethylguanidino)ethyl]-1H-indol-5-yl}amide), 56 |
| 57 | | 1H-Indole-2,5-dicarboxylic acid 5-{[2-(4,5-dihydro-1H-imidazol-2-ylamino)ethyl]amide} 2-({2-[2-(4,5-dihydro-1H-imidazol-2-ylamino)ethylcarbamoyl]-1H-indole-5-yl}amide) dihydrochloride, 57 |
| 58 | | 1H-Indole-2,5-dicarboxylic acid 2-[{2-guanidinoethylcarbamoyl}-1H-indol-5-yl]amide} 5-[(3-guanidinopropyl)amide] dihydrochloride, 58 |

| No. | R | Name |
|---|---|---|
| 59 | | 1H-Indole-2,5-dicarboxylic acid 2-({2-[(N'methylguanidino)ethylcarbamoyl]-1H-indol-5-yl}amide) 5-{[3-(N'methylguanidino)propyl]amide hydrochloride, 59 |
| 60 | | 1H-Indole-2,5-dicarboxylic acid 2-{[2-(N', N''-dimethylguanidino)ethylcarbamoyl]-1H-indol-5-yl}amide} 5-{[3-(N',N''-dimethylguanidino)-propyl]amide} hydrochloride, 60 |
| 61 | | 1H-Indole-2,5-dicarboxylic acid 2-{[2-(2-carbamimidoylethylcarbamoyl)-1H-indol-5-yl]amide} 5-{(2-guanidinoethyl)amide} dihydrochloride, 61 |
| 62 | | 1H-Indole-2,5-dicarboxylic acid 5-[(2-guanidino-ethyl)-amide] 2-{[2-(3-guanidino-propylcarbamoyl)-1H-indol-6-yl]-amide}, 62 |

| No. | R | Name |
|---|---|---|
| 63 | | 1H-Indole-2,5-dicarboxylic acid 5-{[2-(N'-methyl-guanidino)-ethyl]-amide} 2-({2-[3-(N'-methyl-guanidino)-propylcarbamoyl]-1H-indol-6-yl}-amide), 63 |
| 64 | | 1H-Indole-2,5-dicarboxylic acid 2-{[2-(N',N''-dimethyl-guanidino)-ethyl]-amide} 5-({2-[3-(N',N''-dimethyl-guanidino)-propylcarbamoyl]-1H-indol-6-yl}-amide), 64 |
| 66 | | 1H-Indole-2,5-dicarboxylic acid 5-{[2-(2-amino-5-guanidino-pentanoylamino)-ethyl]-amide} 2-({2-[3-(2-amino-5-guanidino-pentanoylamino)-propylcarbamoyl]-1H-indol-6-yl}-amide), 66 |
| 67 | | 1H-Indole-2,5-dicarboxylic acid 5-[(2-guanidino-ethyl)-amide] 2-{[2-(3-guanidino-propylcarbamoyl)-1H-indol-5-yl]-amide}, 67 |

| No. | R | Name |
|---|---|---|
| 68 | | 1H-Indole-2,5-dicarboxylic acid 5-{[2-(N'-methyl-guanidino)-ethyl]-amide} 2-({2-[3-(N'-methyl-guanidino)-propylcarbamoyl]-1H-indol-5-yl}-amide), 68 |
| 69 | | 1H-Indole-2,5-dicarboxylic acid 2-{[2-(N',N''-dimethyl-guanidino)-ethyl]-amide} 5-({2-[3-(N',N''-dimethyl-guanidino)-propylcarbamoyl]-1H-indol-5-yl}-amide), 69 |
| 70 | | N-(2-Guanidino-ethyl)-N'-[2-(2-guanidino-ethylcarbamoyl)-1H-indol-5-yl]-terephthalamide, 70 |
| 72 | | 1H-Indole-2,5-dicarboxylic acid 5-[(3-guanidino-propyl)-amide] 2-{[2-(3-guanidino-propylcarbamoyl)-1H-indol-6-yl]-amide}, 72 |
| 73 | | 1H-Indole-2,5-dicarboxylic acid 5-[(3-(N'-methyl-guanidino)-propyl)-amide] 2-{[2-(3-(N'-methyl-guanidino)-propylcarbamoyl)-1H-indol-6-yl]-amide}, 73 |

-continued

| No. | R | Name |
|---|---|---|
| 74 | | 1H-Indole-2,5-dicarboxylic acid 5-[(3-(N',N''-dimethyl-guanidino)-propyl)-amide] 2-{[2-(3-(N'N''-dimethyl-guanidino)-propylcarbamoyl)-1H-indol-6-yl-]-amide}, 74 |
| 75 | | 1H-Indole-2,5-dicarboxylic acid 5-[(3-guanidino-propyl)-amide] 2-{[2-guanidino-propylcarbamoyl-1H-indol-5-yl-]-amide}, 75 |
| 76 | | 1H-Indole-2,5-dicarboxylic acid 5-[(3-(N'-methyl-guanidino)-propyl)-amide] 2-{[2-(3-(N'-methyl-guanidino)-propylcarbanzoyl)-1H-indol-5-yl-]-amide}, 76 |
| 77 | | 1H-Indole-2,5-dicarboxylic acid 5-[(3-(N',N''-dimethyl-guanidino)-propyl)-amide] 2-{[2-(3-(N'N''-dimethyl-guanidino)-propylcarbamoyl)-1H-indol-5-yl-]-amide}, 77 |

-continued-

| No. | R | Name |
|---|---|---|
| 80 | | 1H-Indole-2,5-dicarboxylic acid 5-[(2-guanidino-ethyl)-amide] 2-{[5-(2-guanidino-ethylcarbamoyl)-1-isobutyl-1H-pyrrol-3-yl]-amide}, 80 |
| 81 | | 1H-Indole-2,5-dicarboxylic acid 2-({1-isobutyl-5-[2-(N'-methyl-guanidino)-ethylcarbamoyl]-1-pyrrol-3-yl}-[2-(N'-methyl-guanidino)-ethyl]-amide), 81 |
| 82 | | 1H-Indole-2,5-dicarboxylic acid 5-[(2-guanidino-ethyl)-amide] 2-([2-(2-guanidino-ethylcarbamoyl)-1H-indol-5-yl]-amide), 82 |
| 89 | | 1H-Indole-2,5-dicarboxylic acid 5-[2-acetimidoylaminoethyl)amide] 2-{[2-(2-acetimidoylaminoethylcarbamoyl)-1H-indole-5-yl]amide} dihydrochloride, 89 |

| No. | R | Name |
|---|---|---|
| 90 | 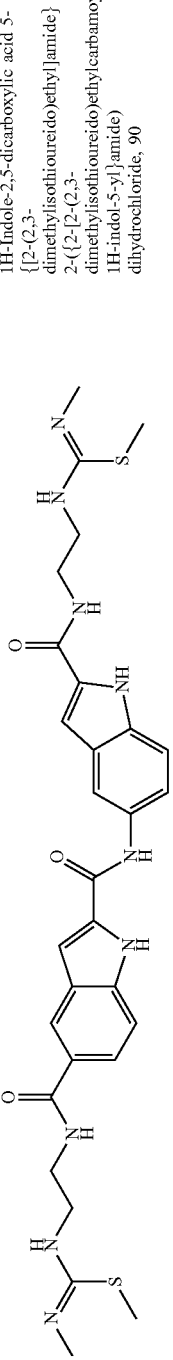 | 1H-Indole-2,5-dicarboxylic acid 5-{[2-(2,3-dimethylisothioureido)ethyl]amide} 2-({2-[2-(2,3-dimethylisothioureido)ethyl]carbamoyl}-1H-indol-5-yl}amide) dihydrochloride, 90 |
| 91 | 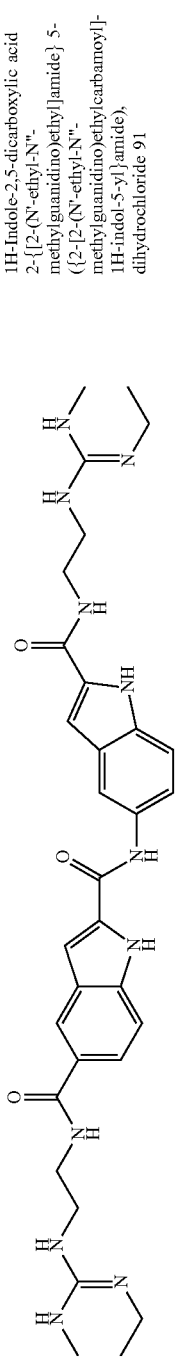 | 1H-Indole-2,5-dicarboxylic acid 2-{[2-(N'-ethyl-N''-methylguanidino)ethyl]amide} 5-({2-[2-(N'-ethyl-N''-methylguanidino)ethyl]carbamoyl}-1H-indol-5-yl}amide), dihydrochloride 91 |
| 92 | 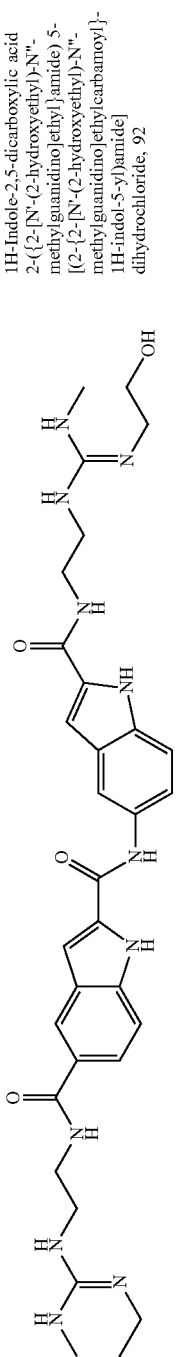 | 1H-Indole-2,5-dicarboxylic acid 2-({2-[N'-(2-hydroxyethyl)-N''-methylguanidino]ethyl]amide} 5-[(2-{2-[N'-(2-hydroxyethyl)-N''-methylguanidino]ethyl]carbamoyl}-1H-indol-5-yl)amide] dihydrochloride, 92 |
| 100 | 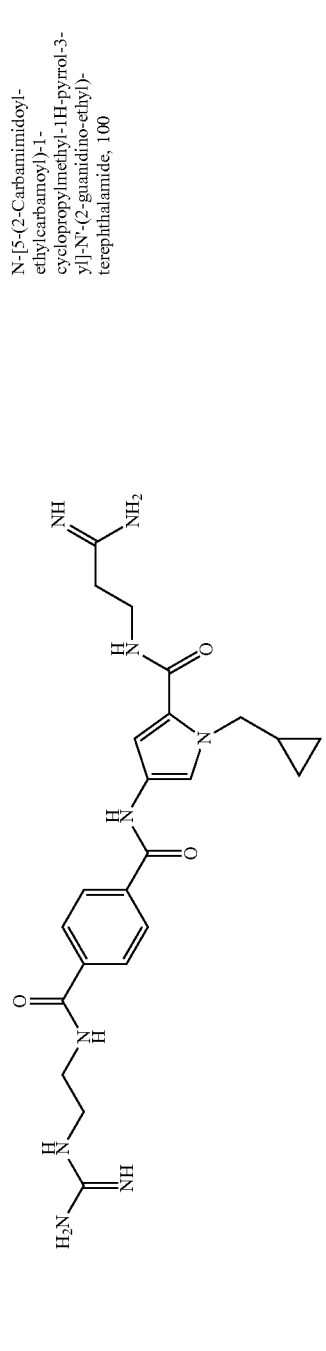 | N-[5-(2-Carbamimidoyl-ethylcarbamoyl)-1-cyclopropylmethyl-1H-pyrrol-3-yl]-N'-(2-guanidino-ethyl)-terephthalamide, 100 |

-continued

| No. | R | Name |
|---|---|---|
| 103 | | 1H-Indole-2,5-dicarboxylic acid 2-{[5-(3-carbamimidoyl-propylcarbamoyl)-1-(3-methyl-butyl)-1H-pyrrol-3-yl]-amide} 5-[(2-guanidino-ethyl)-amide], 103 |
| 108 | | 5-[(5-(N'-methyl-guanidine)-1H-indole-2-carbonyl)-amino]-1H-indole-2-carboxylic acid [2-(N'-methyl-guanidino)ethyl]-amide, 108 |
| 110 | | 5-({[5-[2-(N'-Methyl-guanidino)-acetylamino]-1H-indole-2-carbonyl]-amino}-1H-indole-2-carboxylic acid [2-(N'-methyl-guanidino)ethyl]-amide, 110 |
| 115 | | 5-(3-Guanidino-propionylamino)-1H-indole-2-carboxylic acid [5-(2-carbamimidoyl-ethylcarbamoyl)-1-isobutyl-1H-pyrrol-3-yl]-amide, 115 |

-continued

| No. | R | Name |
|---|---|---|
| 124 | | 6-({4-[2-Guanidino-acetylamino]-1-isobutyl-pyrrole-2-carbonyl]-amino}-1H-indole-2-carboxylic acid (3-guanidinopropyl)-amide, 124 |
| 135 | | 5-{[2-(2-guanidino-acetylamino)-benzofuran-2-carbonyl]-amino}-1H-indole-2-carboxylic acid (2-guanidinoethyl)-amide, 135 |
| 138 | | 5-{[5-(2-guanidino-acetylamino)-1H-indole-2-carbonyl]-amino}-1H-indole-2-carboxylic acid (2-guanidinoethyl)-amide, 138 |
| 154 | | 1H-Indole-2,5-dicarboxylic acid 5-[(2-guanidinooxyethyl)amide] 2-{[2-(2-guanidinooxyethylcarbamoyl)-1H-indole-6-yl]amide}, 154 |
| 155 | | 1H-Indole-2,5-dicarboxylic acid 5-[(2-carbamimidoyloxyethyl)amide] 2-{[2-(2-carbamimidoyloxy-ethylcarbamoyl)-1H-indol-6-yl]amide}, 155 |

| No. | R | Name |
|---|---|---|
| 160 | | 1H-Indole-2,5-dicarboxylic acid 5-[(2-guanidino-ethyl)-amide] 2-{[2-(2-guanidino-ethylthiocarbamoyl)-1H-indol-6-yl[-amide}, 160 |
| 170 | | 1H-Indole-2,5-dicarboxylic acid 5-[(2-(1-methylpyridiniu-2-y)amino-ethyl)-amide] 2-{[2-(2-(1-methylpyridiniu-2-y)amino-ethylcarbamoyl)-1H-indol-6-yl]-amide}, 170 |
| 171 | | 1H-Indole-2,5-dicarboxylic acid 5-[(2-guanidinomethyl-carbamoyl)-1H-indol-6-yl]-carbamoyl}-amide}, 171 |
| 172 | | 1H-Indole-2,5-dicarboxylic acid 2-{[2-guanidino-ethylcarbamoyl)-1H-indol-6-yl]-amide} 5-guanidinomethyl-amide, 172 |
| 173 | | 1H-Indole-2,5-dicarboxylic acid 2-{[2-5-guanidinomethyl-carbamoyl)-1H-indol-6-yl]-amide}, 173 |

| No. | R | Name |
|---|---|---|
| 174 | | 1H-Indole-2,5-dicarboxylic acid 5-[(2-guanidino-ethyl)-amide] 2-{[2-(2-guanidino-ethylcarbamoyl)-benzo[b]thiophen-5-yl]-amide}, 174 |
| 175 | | 1H-Indole-2,5-dicarboxylic acid 5-[(2-guanidino-ethyl)-amide] 2-{[2-(2-guanidino-ethylcarbamoyl)-1H-benzoimidazol-5-yl]-amide}, 175 |
| 176 | | 1H-Indole-2,5-dicarboxylic acid 2-{[2-(2-guanidino-ethylcarbamoyl)-1H-indol-6-yl]-amide}{ 5-[(2-guanidino-ethyl)-methyl-amide], 176 |
| 177 | | Benzo[b]thiophene-2,5-dicarboxylic acid 5-[(2-guanidino-ethyl)-amide] 2-{[2-(2-guanidino-ethylcarbamoyl)-benzo[b]thiophen-5-yl]-amide}, 177 |

-continued

| No. | R | Name |
|---|---|---|
| 178 | | 1H-Indole-2,5-dicarboxylic acid 5-[(2-guanidino-ethyl)-amide] 2-{[2-(2-guanidinoethyl-carbamoyl)-benzo[b]thiophen-6-yl]-amide}, 178 |
| 180 | | 1H-Indole-2,5-dicarboxylic acid 5-[(2-guanidinoethyl)amide] 2-[(2-{2-[(pyridine-2-carboximidoyl)amino]ethylcarbamoyl}-1H-indol-6-yl)amide], 180 |
| 181 | | 1H-Indole-2,5-dicarboxylic acid 2-{[2-(3-carbamimidoylpropyl-carbamoyl)-1H-indol-6-yl]amide} 5-[(2-guanidinoethyl)amide], 181 |

| No. | R | Name |
|---|---|---|
| 182 | | 1H-Indole-2,5-dicarboxylic acid 5-[(2-guanidinoethyl)amide] 2-{[2-(2-methylaminoethyl)-carbamoyl)-1H-indol-6-yl]amide}, 182 |
| 183 | | 1H-Indole-2,5-dicarboxylic acid 2-{[2-(2-dimethylamino-ethylcarbamoyl)-1H-indol-6-yl]amide} 5-[(2-guanidinoethyl)amide], 183 |
| 184 | | 1H-Indole-2,5-dicarboxylic acid 5-[[2-(guanidinoethyl)]amide] 2-({2-[2-(N'-cyanoguanidino)-ethylcarbamoyl]-1H-indol-6-yl]amide}, 184 |

General Synthetic Scheme

Compounds of this invention can be made by the methods depicted in the reaction schemes shown below.

The starting materials and reagents used in preparing these compounds are either available from commercial suppliers such as Aldrich Chemical Co., (Milwaukee, Wis., USA), Bachem (Torrance, Calif., USA), Emka-Chemie, or Sigma (St. Louis, Mo., USA) or are prepared by methods known to those skilled in the art following procedures set forth in references such as Fieser and Fieser's Reagents for Organic Synthesis, Volumes 1–15 (John Wiley and Sons, 1991); Rodd's Chemistry of Carbon Compounds, Volumes 1–5 and Supplementals (Elsevier Science Publishers, 1989), Organic Reactions, Volumes 1–40 (John Wiley and Sons, 1991), March's Advanced Organic Chemistry, (John Wiley and Sons, 5th Edition), and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

General synthetic methods of compounds of the present invention are described in Schemes A–F. Syntheses of specific examples are provided in Schemes 1–12.

Starting materials 201, 202, 206, 207, 215, 220 and 226 are either commercially available from vendors listed above in the General Synthetic Scheme section, or can be prepared by methods well known in the art. For example, Compounds 201 and 202 can be prepared by the procedure illustrated in Scheme 1 and described in detail in Example 1.

Compounds of Formula (I) wherein $Y^1$ is $-C(=W)NR^1R^3$; $Y^2$ is $-C(=W)NR^2R^{21}$; W is O; $R^3$ and $R^{21}$ are hydrogen; $R^1$ and $R^2$ are as defined in the Summary of the Invention and are the same; and $X^1$ and $X^2$ are as defined in the Summary of Invention can be prepared as described in Scheme A.

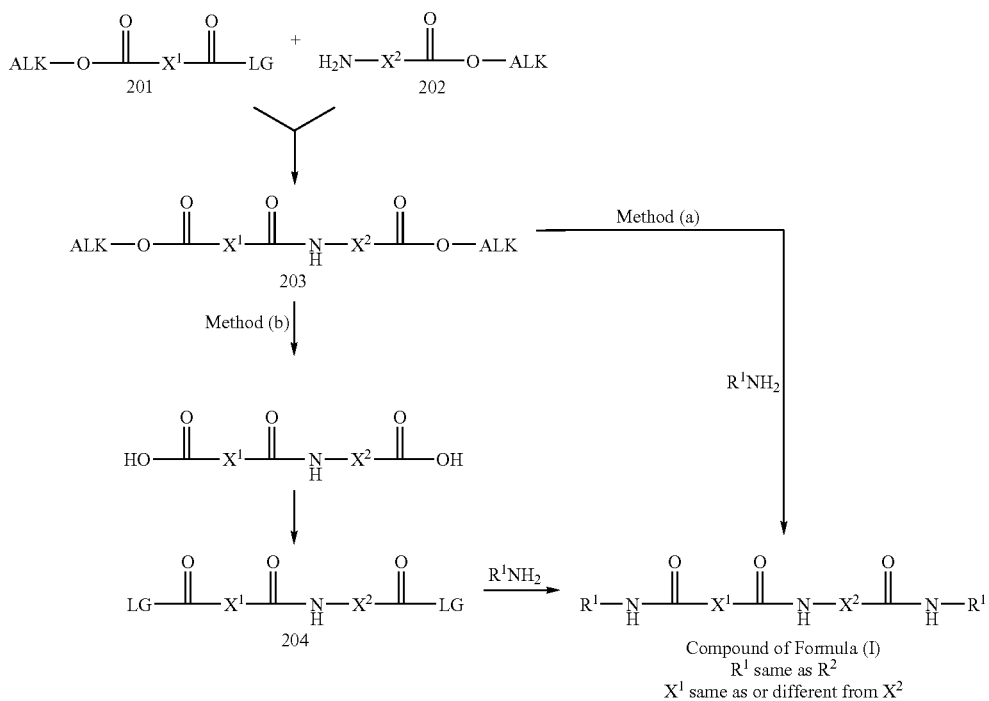

A compound of Formula (I) wherein $Y^1$ is $-C(=W)NR^1R^3$; $Y^2$ is $-C(=W)NR^2R^{2"}$; W is O; $R^3$ and $R^{21}$ are hydrogen; $R^1$ and $R^2$ are as defined in the Summary of the Invention and are the same; and $X^1$ and $X^2$ are as defined in the Summary of Invention can be prepared by reacting a carboxylic acid derivative 201 (wherein LG is a suitable leaving group such as halo, pentafluorophenyloxy, and the like, and ALK is an alkyl group) with an amine 202. The reaction is typically carried out in a polar organic solvent such as dimethylformamide, tetrahydrofuran, and the like. It will be recognized by a person skilled in the art that if the leaving group is halo, pentafluorophenyloxy, and the like, then the reaction will be conducted in the presence of a non-nucleophilic base such as triethylamine, diisopropylethylamine (DIEA), and the like.

The reaction product diester 203 is then converted to a compound of Formula (I) by following the procedures illustrated in method (a) or (b) in Scheme A. In method (a), the diester 203 is treated with an amine of formula $R^1NH_2$ to provide a compound of Formula (I) wherein $R^1$ and $R^2$ are the same; and $X^1$ and $X^2$ can be the same or different. The reaction is carried out in a polar organic solvent such as dimethylformamide, tetrahydrofuran and the like.

In method (b), the diester is first hydrolyzed under basic hydrolysis conditions to provide a diacid, which is then converted to a compound of Formula (I) under the conditions described above.

In some cases, $R^1$ can be further converted to different tails. For example, in Scheme 1, Compound 8 or 14 can further react with ethyl acetamidate hydrochloride to give Compound 9 or 23 respectively. Alternatively, Compound 8 or 14 can further react with pyrazole-1-carboxamidine hydrochloride to give Compound 10 or 18 respectively.

Additionally, it will be apparent to a person skilled in the art that a compound of Formula I wherein $Y^1$ is —C(=W)OR$^1$; $Y^2$ is —C(=W)OR$^2$; W is O can be prepared by following the above procedure but substituting the amino group in compound 202 with a hydroxy group. It will also be apparent to a person skilled in the art that when a properly substituted amine is used in place of $R^1NH_2$ in Scheme A, compounds of Formula (I) wherein $R^3$ and $R^{21}$ are as defined in the Summary of Invention can be obtained.

Alternatively, compounds of Formula (I) wherein $Y^1$ is —C(=W)NR$^1$R$^3$; $Y^2$ is —C(=W)NR$^2$R$^{21}$; W is O; and $R^1$, $R^2$, $R^3$, $R^{21}$, $X^1$ and $X^2$ are as defined in the Summary of the Invention can be prepared as described in Scheme B below.

nucleophilic organic base such as DIEA and the like. The resulting ester 205 can then be converted to a carboxylic acid derivative 206 with a proper leaving group defined above.

A compound of Formula (I) wherein $Y^1$ is —C(=W)NR$^1$R$^3$; $Y^2$ is —C(=W)NR$^2$R$^{21}$; W is O; and $R^1$, $R^2$, $R^3$, $R^{21}$, $X^1$ and $X^2$ are as defined in the Summary of the Invention can be prepared by alternative method c or method d. In method c, a carboxylic acid derivative 206 is allowed to react with an amine 202 under the similar conditions described above for the preparation of 205. The resulting ester 209 can then react with another amine of formula $R^2$—NH—$R^{21}$ followed by removal of the protection group of $R^1$ to give a compounds of Formula (I) wherein $R^1$ and $R^2$, or $X^1$ and $X^2$ can be the same or different. The procedure for deprotection is well known to one skilled in the art. For example, various protecting groups and deprotecting procedures are described in Greene, T. W and Wuts, P. G. M. "*Protecting Groups in Organic Synthesis*", Third Ed., 1999, Wiley-Interscience, New York.

In method d, a carboxylic acid derivative 206 is allowed to react with an amine 210 under the similar conditions described above for the preparation of 205. The resulting compound 212 can then be deprotected under the similar conditions described above to give a compound of Formula (I) wherein $R^1$ and $R^2$, or $X^1$ and $X^2$ can be the same or

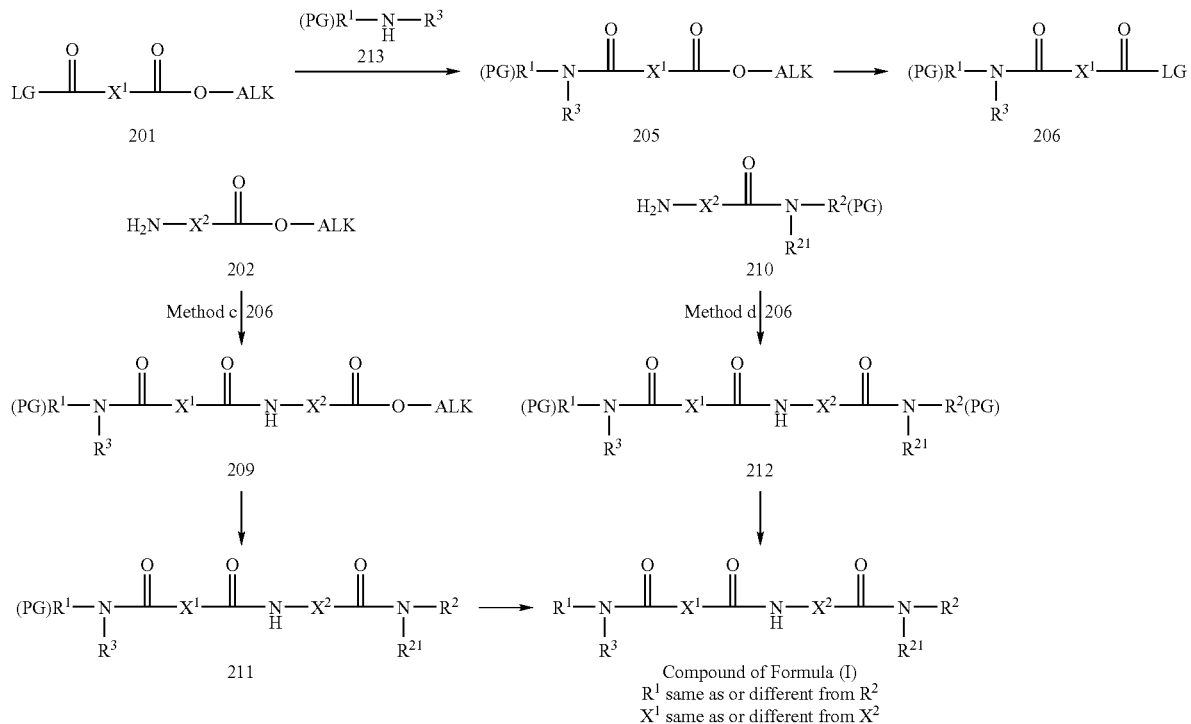

Scheme B

The preparation starting with reacting a carboxylic acid derivative 201 (wherein LG is a suitable leaving group such as halo, pentafluorophenyloxy, and the like, and ALK is an alkaly group) with an amine 213 (wherein (PG) is a suitable protecting group for $R^1$ such as t-butoxycarbonyl (t-Boc), and the like). The reaction of 201 and 213 is typically carried out in a polar organic solvent such as dimethylformamide, tetrahydrofuran, and the like, in the presence of a non different. The starting compound 210 in method d can be prepared by methods well known in the art. One example of preparing compound 210 is illustrated in Scheme 2 and described in detail in Example 33.

Some examples of preparing compounds of Formula (I), following the procedure described in Scheme B, can be found in Examples 30–35 (Scheme 2, Compound Al); and Examples 78–83 (Scheme 4, Compounds 88–29).

Compounds of Formula (I) wherein $Y^1$ is —NHC(=W)$R^1$ or $R^5$; $Y^1$ is —C(=W)NR R"; W is O; and $R^1$, $R^2$, $R^5$, $R^{21}$, $X^1$ and $X^2$ are as defined in the Summary of the Invention can be prepared as described in Scheme C below.

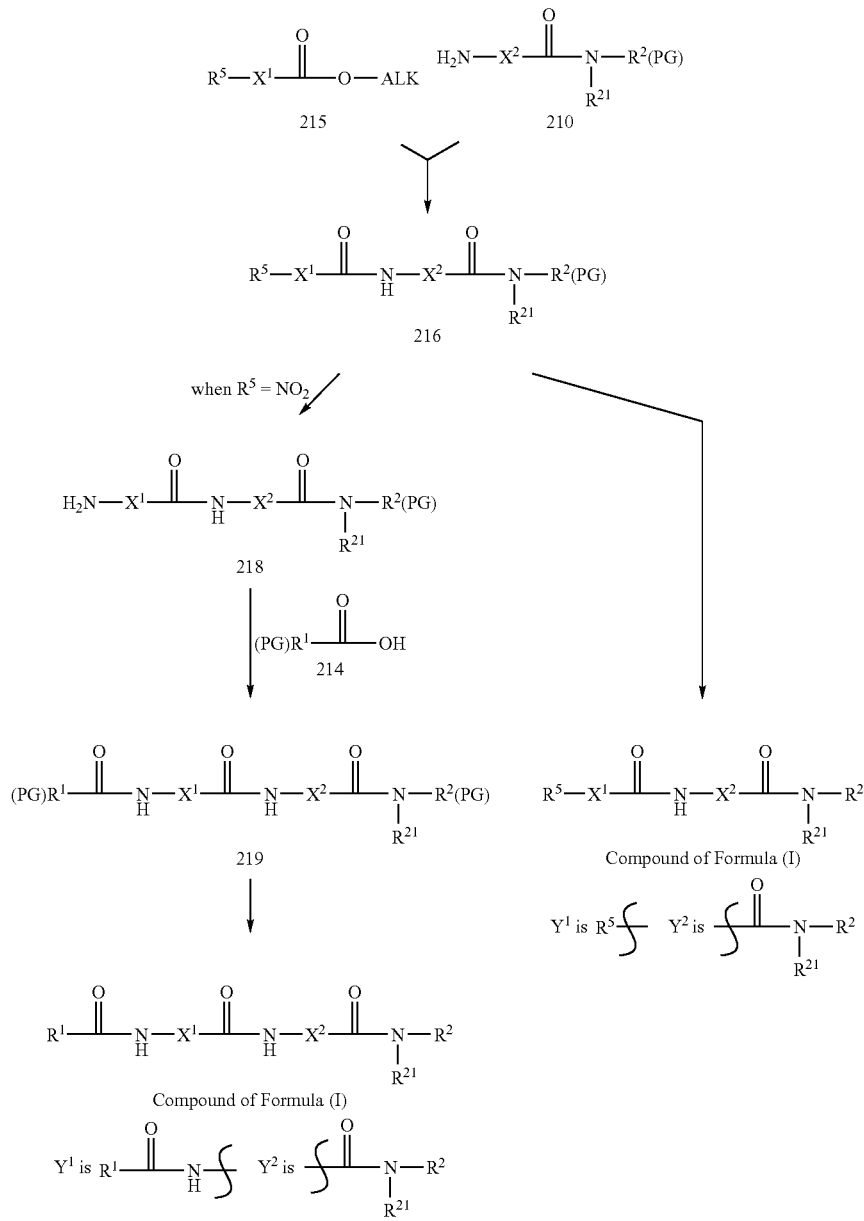

Compounds of Formula (I) wherein $Y^1$ is —NHC(=W)$R^1$; $Y^2$ is —C(=W)NR$^2$R$^{21}$; W is O; and $R^1$, $R^2$, $R^5$, $R^{21}$, $X^1$ and $X^2$ are as defined in the Summary of the Invention can be prepared by reacting a carboxylic acid derivative 215 with an amine 210 under the similar reactions conditions described above for the preparation of 205. The resulting compound 216 (wherein $R^5$ is —NO$_2$) can be reduced to amine 218 using methods well known in the art. For example, hydrogenation over a catalyst such as Pd/C, and the like, and in an organic solvent such as methanol, and the like. Amine 218 is then allowed to react with a carboxylic acid 214. Removal of the protection group in compound 219 give a compound of Formula (I) wherein $Y^1$ is —NHC(=O)$R^1$; $Y^2$ is —C(=O)NR$^2$R$^{21}$; and $R^1$ and $R^2$ are the same or different. Examples of compounds of Formula (I) prepared by the methods illustrated in Scheme C can be found in Scheme 6 and in Examples 97 and 98.

Compounds of Formula (I) wherein $Y^1$ is —$R^5$; $Y^2$ is —C(=W)NR$^2$R$^{21}$; W is O; and $R^2$, $R^5$, $R^{21}$, $X^1$ and $X^2$ are as defined in the Summary of the Invention can be prepared by removing the protection group in compound 216 under the similar conditions described above. In some cases, $R^5$ can be further transformed to compounds of Formula (I) with different $R^5$ substituents. Examples of such transformation can be found in Scheme 6 and in Examples 96, 99 and 100.

Compounds of Formula (I) wherein $Y^1$ is —C(=W)NR$^1$R$^3$; $Y^2$ is —C(=W)NR$^2$R$^{21}$; W is O; R$^3$ and R$^{21}$ are hydrogen; R$^1$ and R$^2$ are as defined in the Summary of Invention wherein L is as defined and T is O; and $X^1$ and $X^2$ are as defined in the Summary of Invention can be prepared as described in Scheme D.

and ALK are defined as in Scheme A above) with a substituted amine 225. The reaction is typically carried out in a polar organic solvent such as dimethylformamide, tetrahydrofuran, and the like. The reaction product can then be converted to compound 222 by base hydrolysis, followed by acetylation. Both procedures are well known in the art.

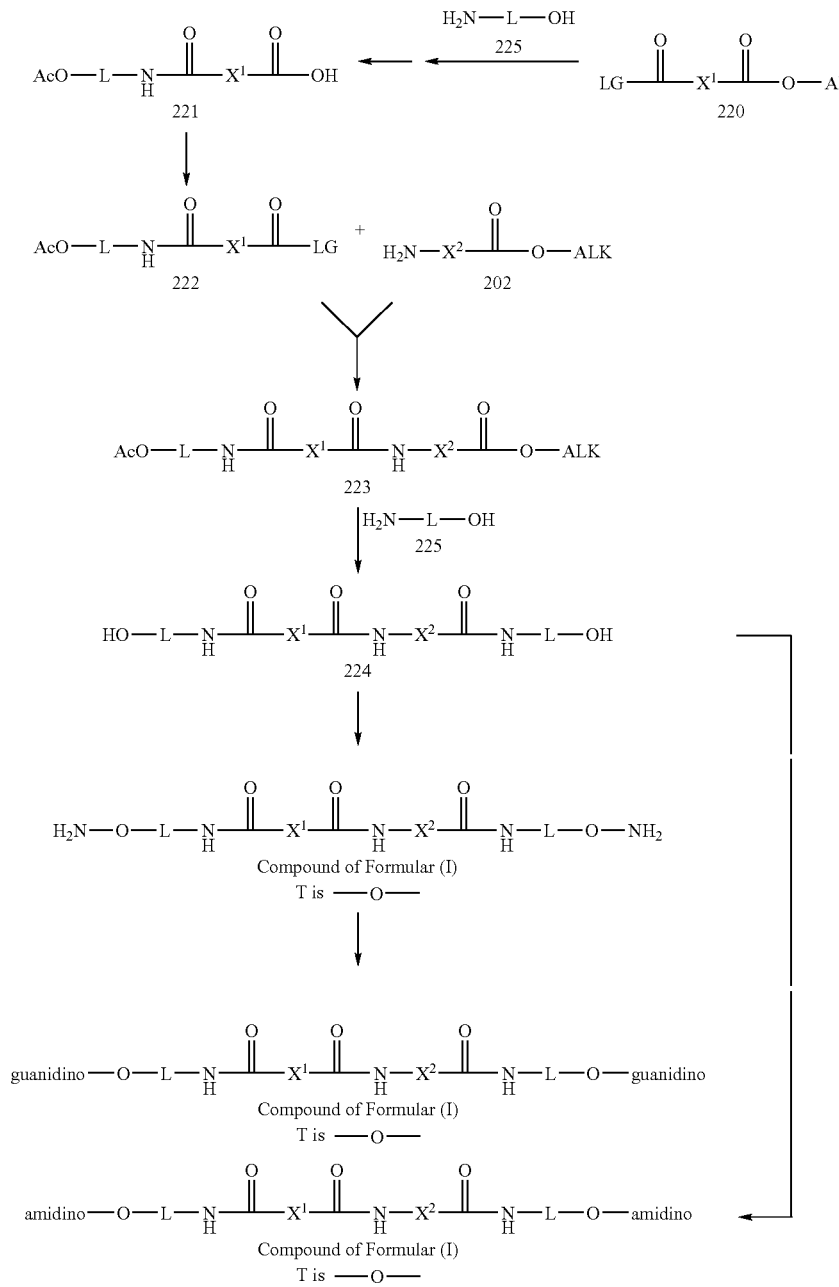

Compounds of Formula (I) wherein $Y^1$ is —C(=W)NR$^1$R$^3$; $Y^2$ is —C(=W)NR$^2$R$^{21}$; W is O; R$^3$ and R$^{21}$ are hydrogen; R$^1$ and R$^2$ are as defined in the Summary of Invention wherein L is as defined and T is O; and $X^1$ and $X^2$ are as defined in the Summary of Invention can be prepared by reacting a carboxylic acid derivative 220 (wherein LG Subsequently, compound 222 can be mixed with an amine 202 under conditions described above for the preparation of 203 in Scheme A. The resulting compound 223 can now be treated with a substituted amine 225 in a polar organic solvent such as dimethylformamide, tetrahydrofuran, and the like, to yield bis-hydroxyl compound 224. The two hydroxyl groups in compound 224 are converted to oxyamino-, oxyguanidino- or oxyamidino-groups, as exemplified by compounds 153, 154 and 155 respectively, in Scheme 8 and in Examples 126–131.

Compounds of Formula (I) wherein $Y^1$ is —C(=W)NR$^1$R$^3$; $Y^2$ is —C(=W)NR$^2$R$^{21}$; W is O or S; and R$^1$, R$^2$, R$^3$, R$^{21}$, X$^1$ and X$^2$ are as defined in the Summary of Invention can be prepared as described in Scheme E below.

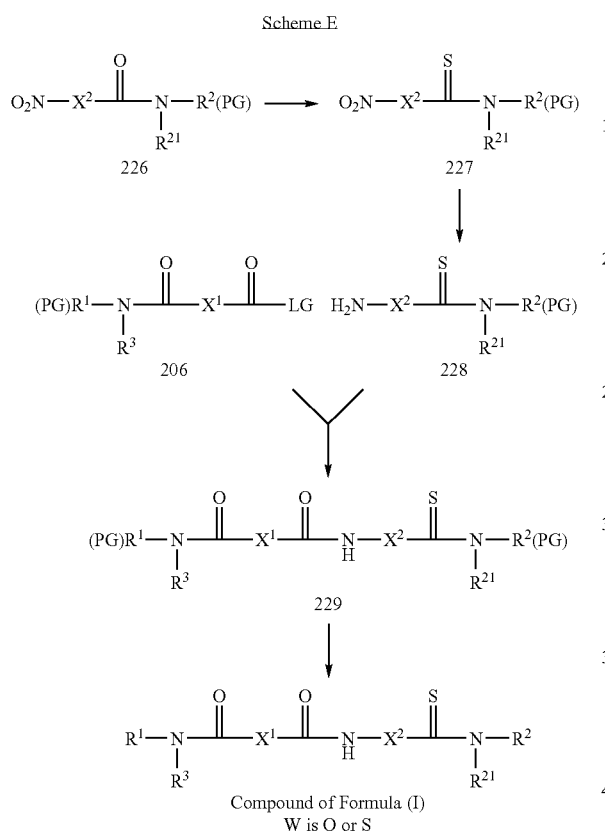

Compounds of Formula (I) wherein $Y^1$ is —C(=W)NR$^1$R$^3$; $Y^2$ is —C(=W)NR$^2$R$^{21}$; W is O or S; and R$^1$, R$^2$, R$^3$, R$^{21}$, X$^1$ and X$^2$ are as defined in the Summary of Invention can be prepared starting with an amide derivative 226. When treated with Lawesson's Reagent, the carbonyl in amide derivative 226 can be converted to a thiocarbonyl to give compound 227. The conversion of a carbonyl group to a thiocarbonyl group using Lawesson's Reagent is well known in the art and is described, for example in Fieser and Fieser's *Reagents for Organic Synthesis, Volunzes 1–15*, John Wiley and Sons, 1991. It is obvious to one skilled in the art that other carbonyl groups in Scheme E can be converted to thiocarbonyl groups to yield compounds of formula (I). Subsequently, the nitro group in compound 227 can be reduced to give an amine derivative 228. The reaction of 228 with a carboxylic acid derivative 206 can be carried out similarly as described in Scheme B for the non-thiocabonyl counterparts. The resulting compound 229 can then undergo deprotection reaction to give compounds of Formula (I) wherein W is O or S. An example of such compounds is compound 159 in Scheme 9. Its preparation is described in Examples 132 and 133. In some cases, R$^1$ and/or R$^2$ can be further converted to different tails as illustrated in Scheme 9 for compound 160, and described in Example 134.

Compounds of Formula (I) wherein $Y^1$ is —C(=W)NR$^1$R$^3$; $Y^2$ is —R$^{22}$; W is O; and R$^1$, R$^1$, R$^{22}$, X$^1$ and X$^2$ are as defined in the Summary of Invention can be prepared as illustrated in Scheme F.

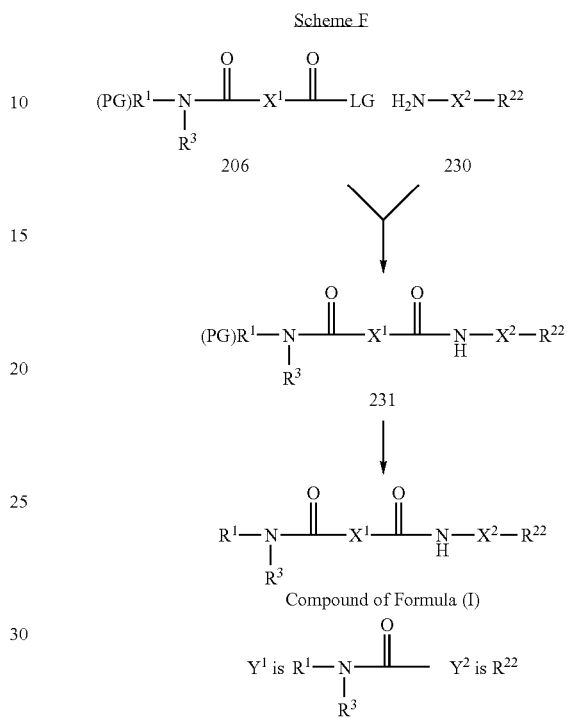

Compounds of Formula (I) wherein $Y^1$ is —C(=W)NR$^1$R$^3$; $Y^2$ is —R$^{22}$; W is O; and R$^1$, R$^3$, R$^{22}$, X$^1$ and X$^2$ are as defined in the Summary of Invention can be prepared by reacting an carboxylic acid derivative 206 with an amine 230 under similar reaction conditions as described in Scheme A for the preparation of 203. The protecting group in compound 231 can then be removed to give compounds of Formula (I). The starting amine 230 can be prepared by procedures well known in the art. Examples of such preparation can be found in Scheme 9 and in Examples 135 and 136.

The present invention provides novel compounds possessing one or more of the following activities: antibacterial, antifungal, antiviral, anticancer, and antiparasitic activity. The compounds and compositions containing them are therefore useful in the treatment of one or more of the following diseases: bacterial, fungal, viral and parasital infections, and cancer Compounds of Formula (I) are also useful as ultraviolet (UV) light absorbers. Accordingly, they are suitable for use in compositions requiring a UV light absorbing additive, such as plastic compositions. In this regard, it is known that prolonged exposure to UV light can have a deleterious effect on the physical properties and compositional stability of certain plastics. It is therefore conventional to include a UV light absorbing additive in such plastic compositions, and the compounds of Formula (I) can be employed in this manner.

Compounds of the present invention are further useful in that they bind to the minor groove of dsDNA thereby inducing DNA duplex formation. This property is beneficial in biological assays or diagnostic tests that measure the formation or stability of DNA duplexes. For instance, where one is attempting to measure the formation of a DNA duplex with a low $T_m$, one can increase the duplex population by adding a compound of Formula (I). Such an increase in population ensures that the binding event will be more easily measured. A compound of Formula (I) can also be used where one is detecting a single nucleotide polymorphism (SNP) through duplex formation. The compound will preferentially increase the $T_m$ of a perfectly matched duplex over a single mutated duplex, therein allowing one to more easily distinguish the two.

Administration and Pharmaceutical Composition

In general, the compounds of this invention will be administered in a therapeutically effective amount by any of the accepted modes of administration for agents that serve similar utilities. The actual amount of the compounds of this invention, i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day.

Therapeutically effective amounts of compounds of Formula (I) may range from approximately 0.005 to 50 mg per kilogram body weight of the recipient per day; preferably about 0.01–25 mg/kg/day, more preferably from about 0.5 to 10 mg/kg/day. Thus, for administration to a 70 kg person, the dosage range would most preferably be about 35–70 mg per day.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen which can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of this invention is inhalation. This is an effective method for delivering a therapeutic agent directly to the respiratory tract for the treatment of diseases such as asthma and similar or related respiratory tract disorders (see U.S. Pat. No. 5,607,915).

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist which is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula (I) in combination with at least one pharmaceutically acceptable excipient. Acceptable excipients are non-toxic, aid administration, and do not adversely affect the therapeutic benefit of the compound of Formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the compound in a formulation can vary within the full range employed by those skilled in the art. Typically, the formulation will contain, on a weight percent (wt %) basis, from about 0.01–99.99 wt % of a compound of Formula (I) based on the total formulation, with the balance being one or more suitable pharmaceutical excipients. Preferably, the compound is present at a level of about 1–80 wt %. Representative pharmaceutical formulations containing a compound of Formula (I) are described below.

SYNTHETIC EXAMPLES

The following preparations, schemes and examples are given to enable those skilled in the art to more clearly understand and to practice the present invention. They should not be considered as limiting the scope of the invention, but merely as being illustrative and representative thereof.

The following abbreviations are employed:
Ac for acetyl;
AcOEt for ethyl acetate;
Arg for a arginine amino acid residue;
Boc or t-Boc for a tert-butoxycarbonyl protecting group;
Boc Py for N-Boc-4-amino-1-methyl pyrrole-2-carboxylic acid;

Boc-5-Ain for N-Boc-5-Amino-Indole-2-Carboxylic Acid;
Boc-5-Ain-HBA-AMPS for N-Boc-5-Amino-Indole-2-Carboxylic Acid (p-Hydroxy benzamide methyl polystyrene)ester;
Boc-Py-HBA-AMPS for N-Boc-4-Amino-1-Methyl Pyrrole-2-Carboxylic Acid (p-Hydroxy benzamide methyl polystyrene)ester;
BOP for Benzotriazol-1-yloxy-tris(dimethylamino)phosphonium hexafluorophosphate;
Bzl for a benzyl protecting group;
DCC for N,N'-dicyclohexylcarbodiimide;
DCE for 1,2-dichloroethane;
DCM for dichloromethane;
DCU for N,N'-dicyclohexylurea;
DE for 2-(Dimethylamino)ethylamine;
DIC for N,N' diisopropyl carbodiimide;
DIEA for diisopropylethylamine;
DMAP for 4-Dimethylaminopyridine;
DMF for dimethyl formamide;
DMF for dimethylformamide;
DMSO for dimethylsulfoxide;
DP for 3-(Dimethylamino)propylamine;
Et for an ethyl radical;
EtOH for ethanol;
Fmoc for a fluorenylmethoxycarbonyl protecting group;
Gly for a glycine amino acid residue;
HBA-AMPS for p-hydroxybenzamide-methylpolystyrene;
HBTU for O-Benzotriazol-1 yl-N,N,N',N'-tetramethyluronium hexafluorophosphate;
HCl for hydrochloric acid;
HPLC for high pressure liquid chromatography;
Lys for a lysine amino acid residue;
MBHA for methylbenzhydrylamine;
MBHA resin for methylbenzhydrylamine polystyrene resin Me for a methyl radical;
MeOH for methanol;
MMT for a monomethoxytrytil (p-anisyldiphenylmethyl) protecting group;
mp d for melting point with decomposition;
mp for melting point;
MS for mass spectrum;
NMR for nuclear magnetic resonance spectrum;
Np for a 4-nitrophenyl radical;
Npc(Et) for a 4-nitro-1-ethyl-1H-pyrrole-2-carboxylic acid residue;
Npc(Me) for a 4-nitro-1-methyl-1H-pyrrole-2-carboxylic acid residue;
Npc(Pr) for a 4-nitro-1-propyl-1H-pyrrole-2-carboxylic acid residue;
Pfp for a pentafluorophenyl radical;
Phe for a phenyl radical;
Py for a 4-amino-1-methyl-1H-pyrrole-2-carboxylic acid residue;
Pyr for pyridine;
Pzl-Gu-(Boc)$_2$ for N,N '-Bis(tert-butoxycarbonyl)-1H-pyrazole-1-carboxamidine;
t-Bu for a tert-butyl protecting group;
TFA for trifluoroacetic acid;
THF for tetrahydrofuran;
TLC for thin layer chromatography on silica gel;
Trt for a triphenylmethyl radical; and
Z for a benzyloxycarbonyl protecting group.

In reporting NMR data, chemical shifts are given in ppm and coupling constants (J) given in Hertz (Hz). All melting points are uncorrected.

Schemes 1–12 illustrate specific synthetic routes to various compounds of the present invention.

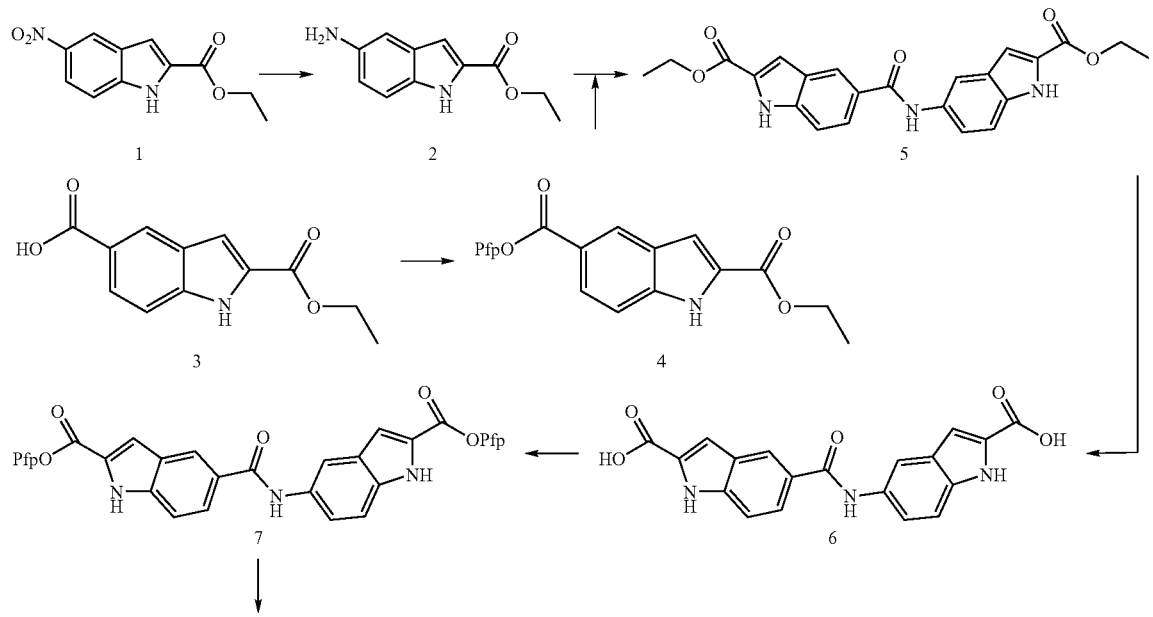

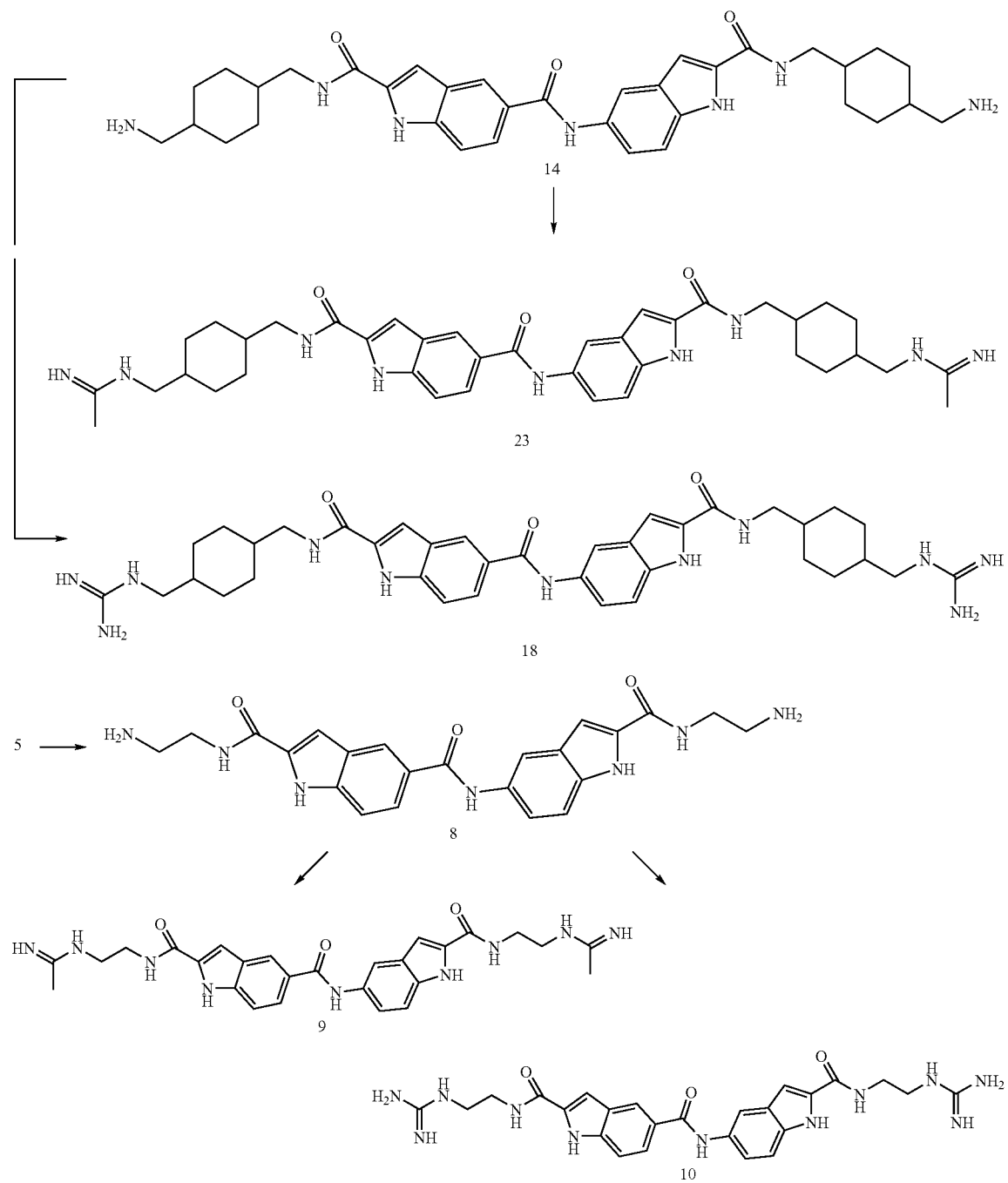
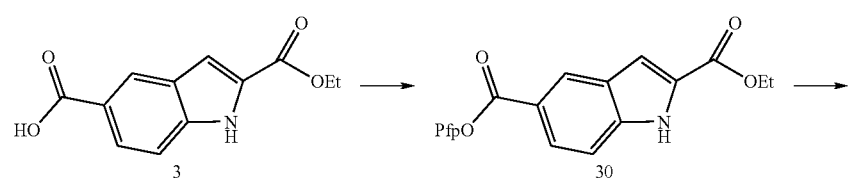

-continued
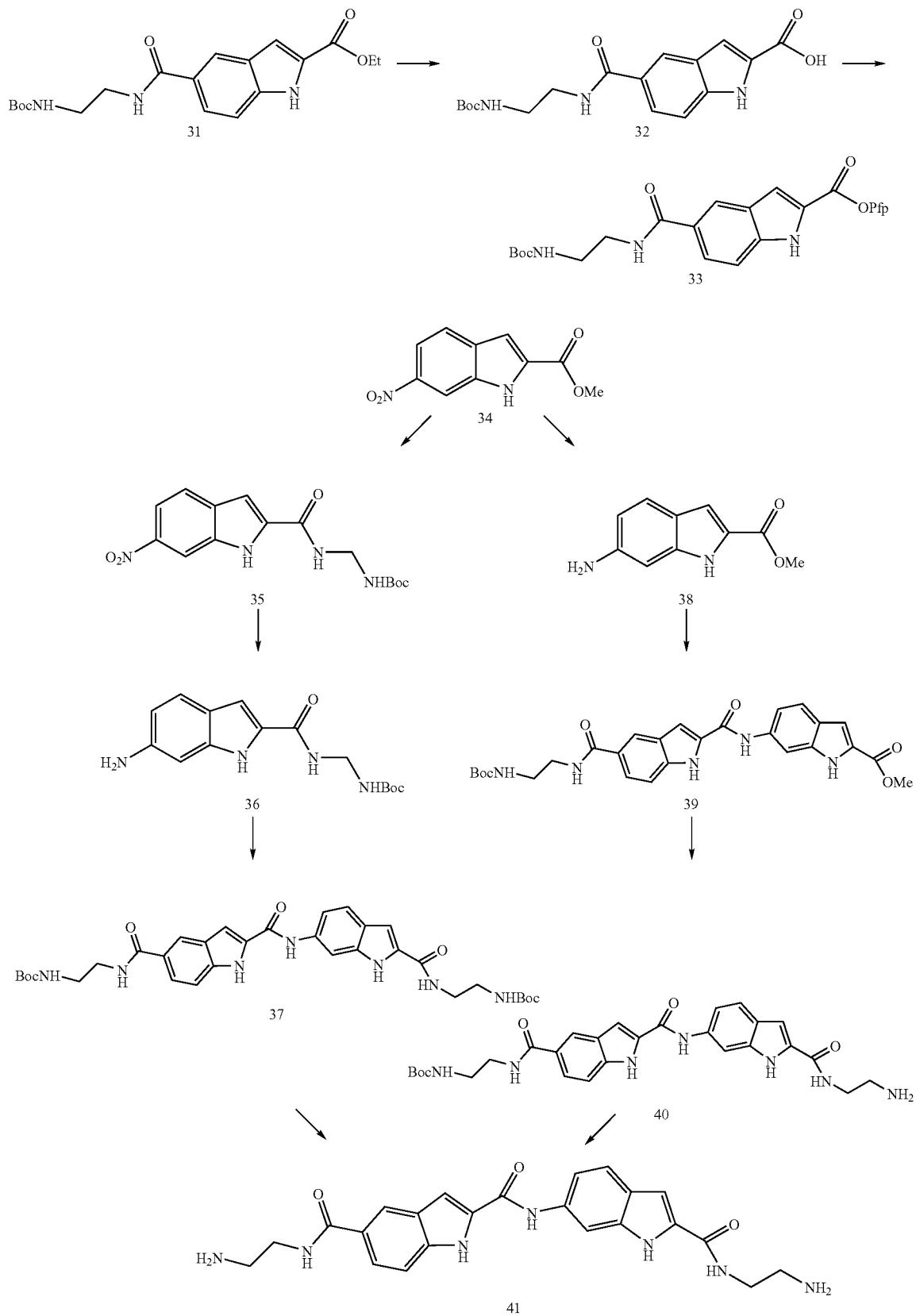

Scheme 3
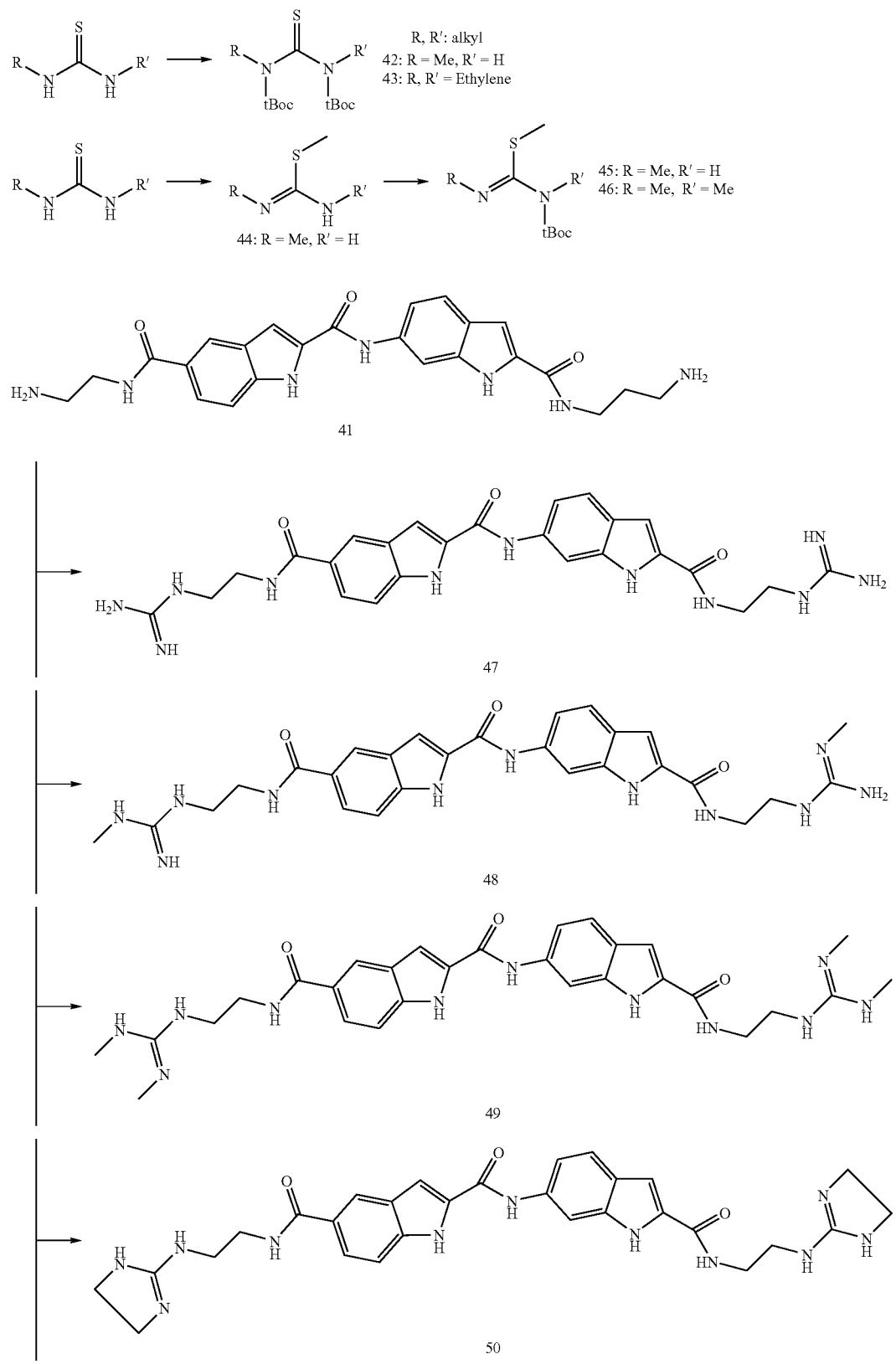

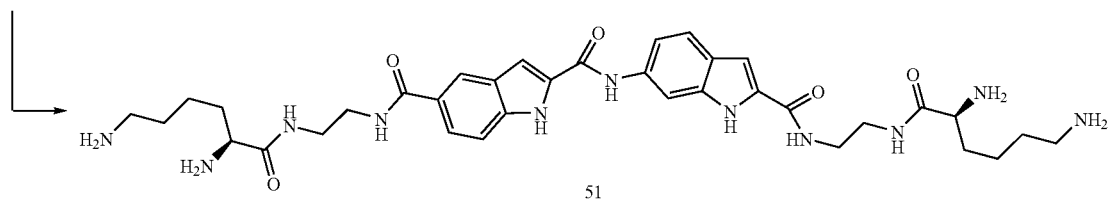
Scheme 4
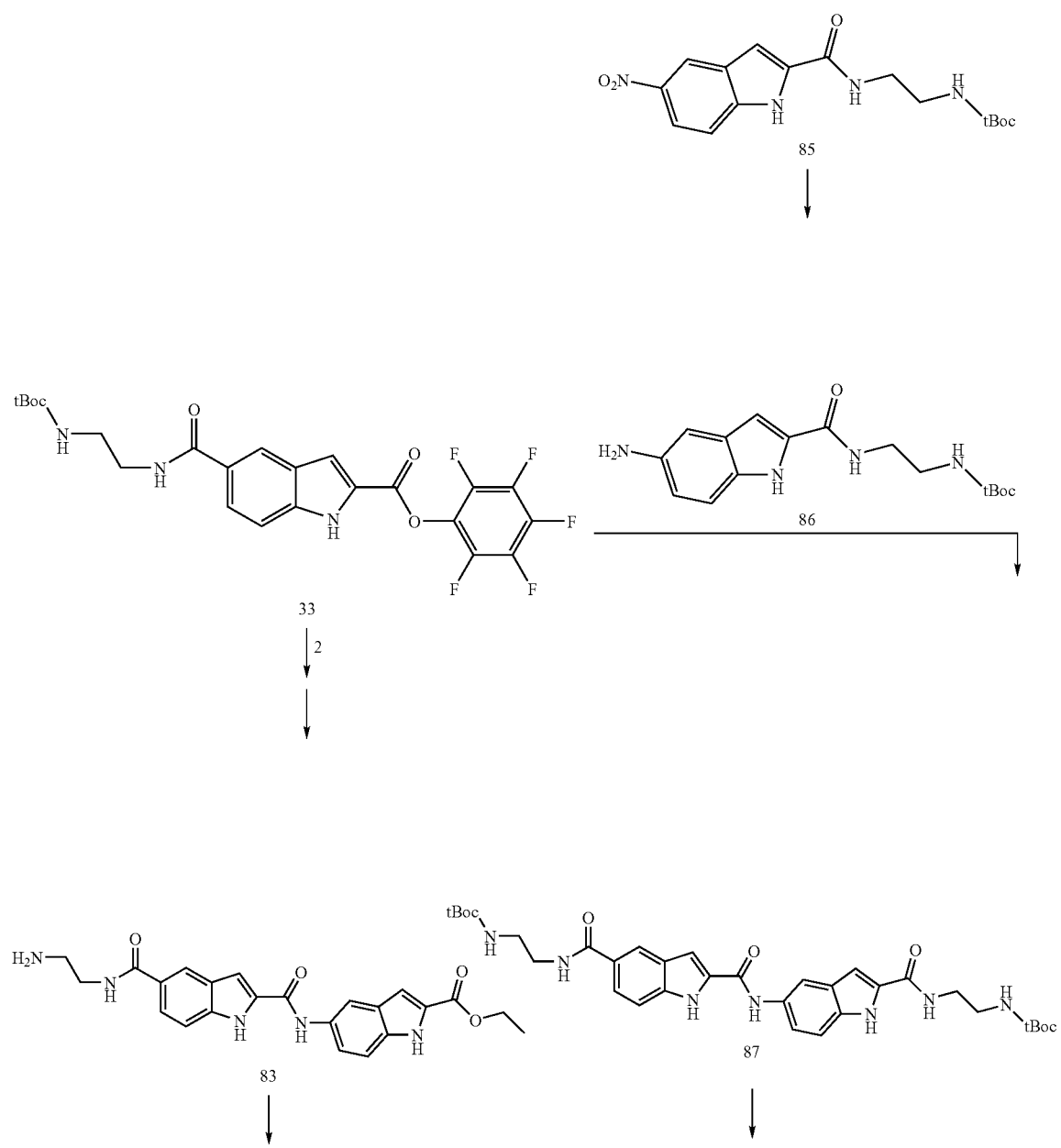

73 74
-continued
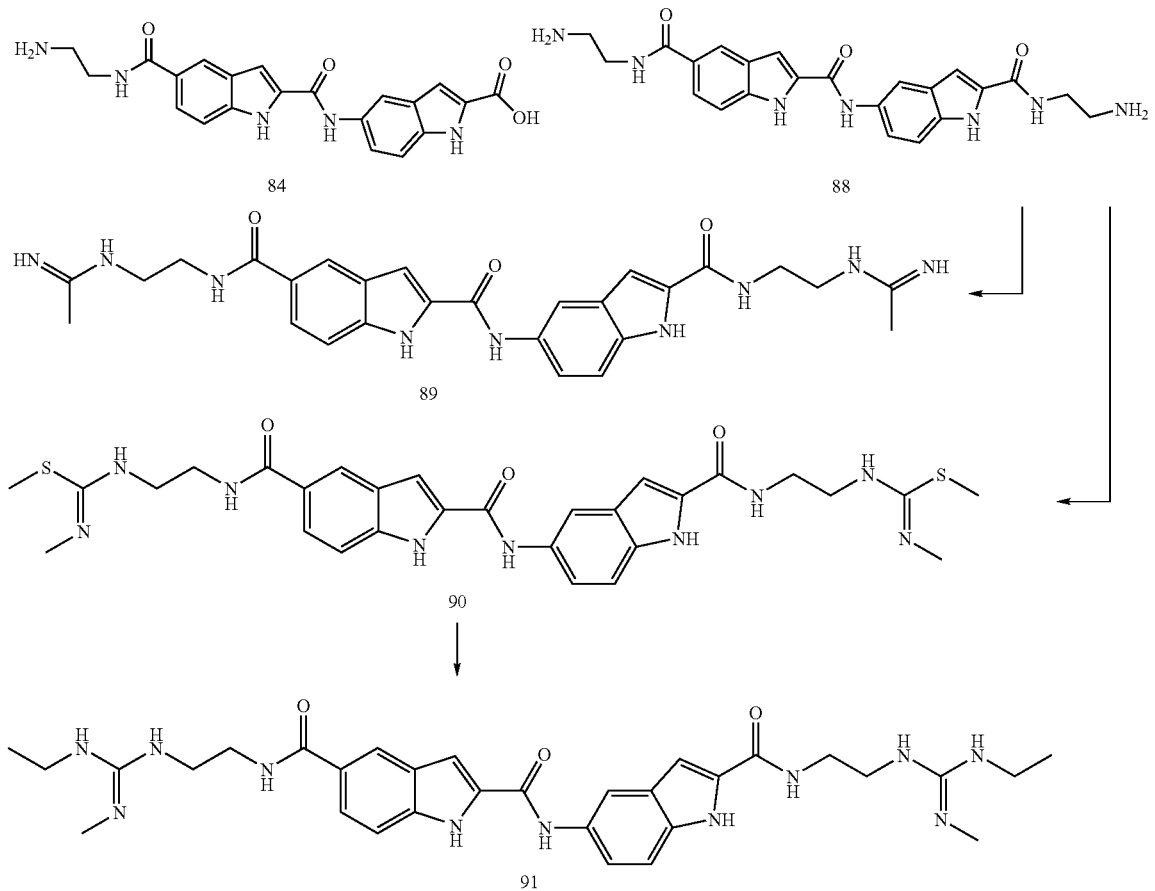
Scheme 5
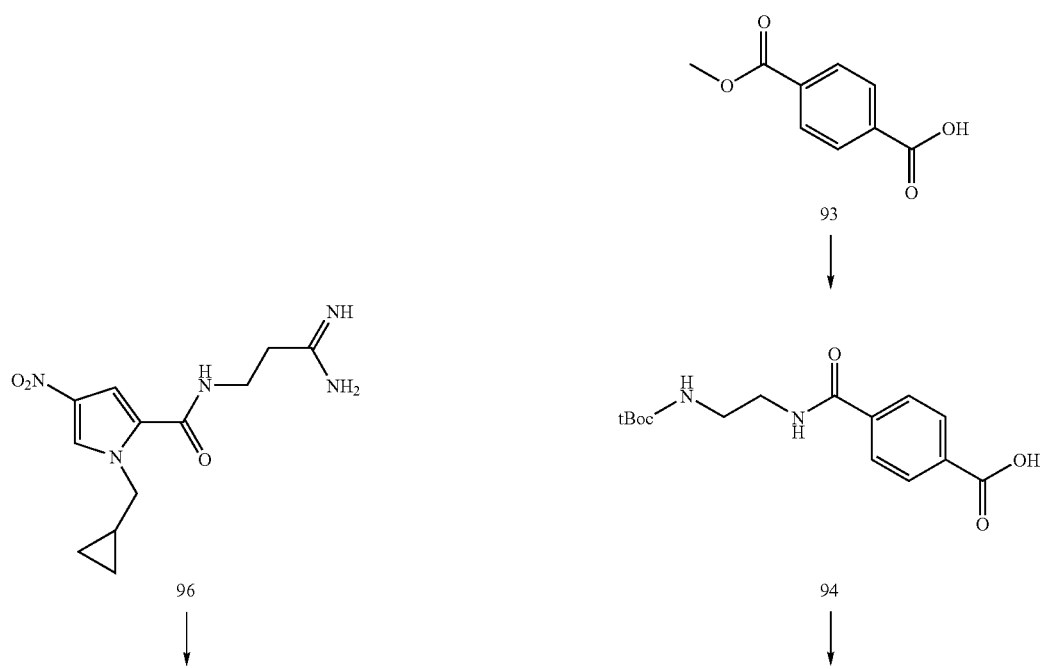

-continued
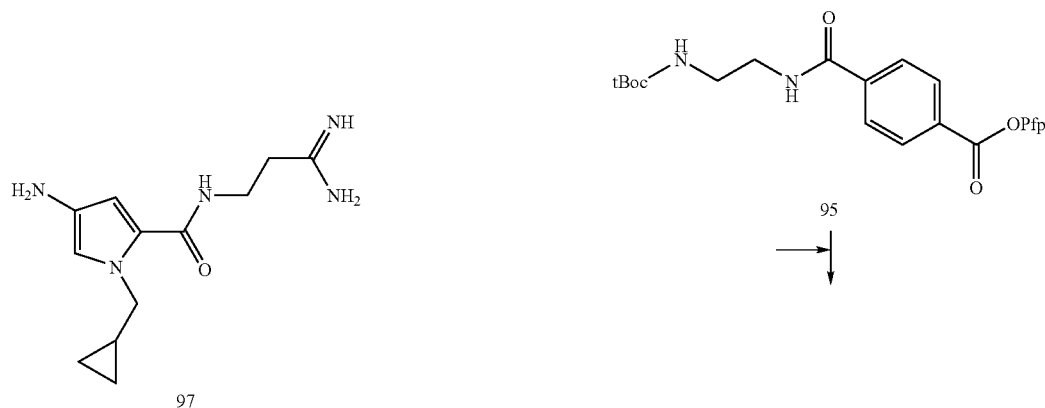
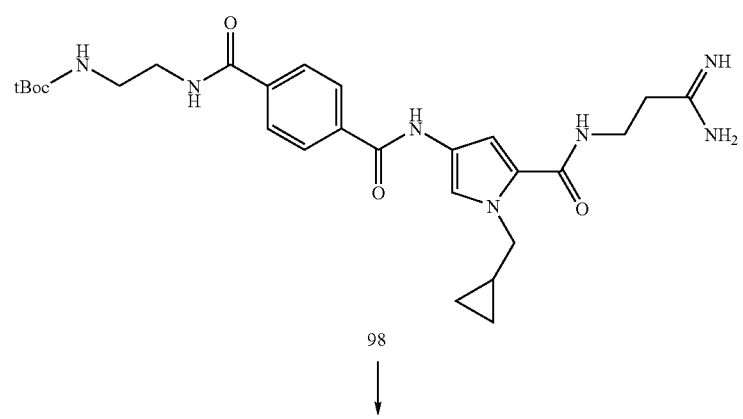
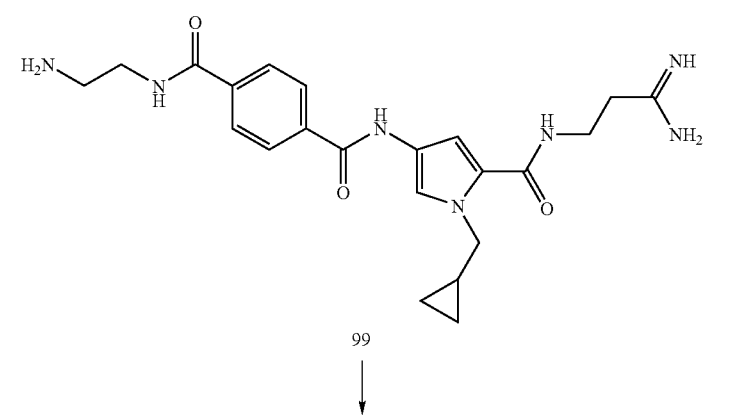
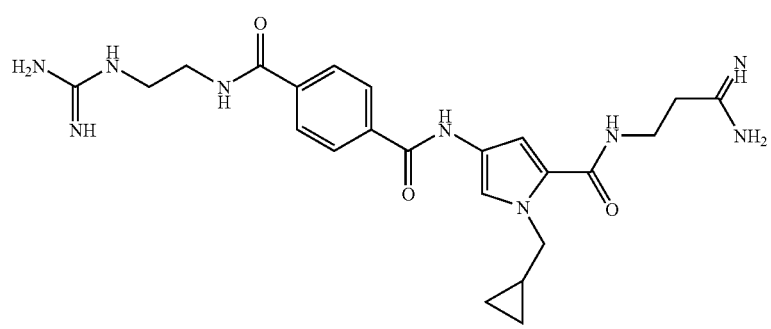

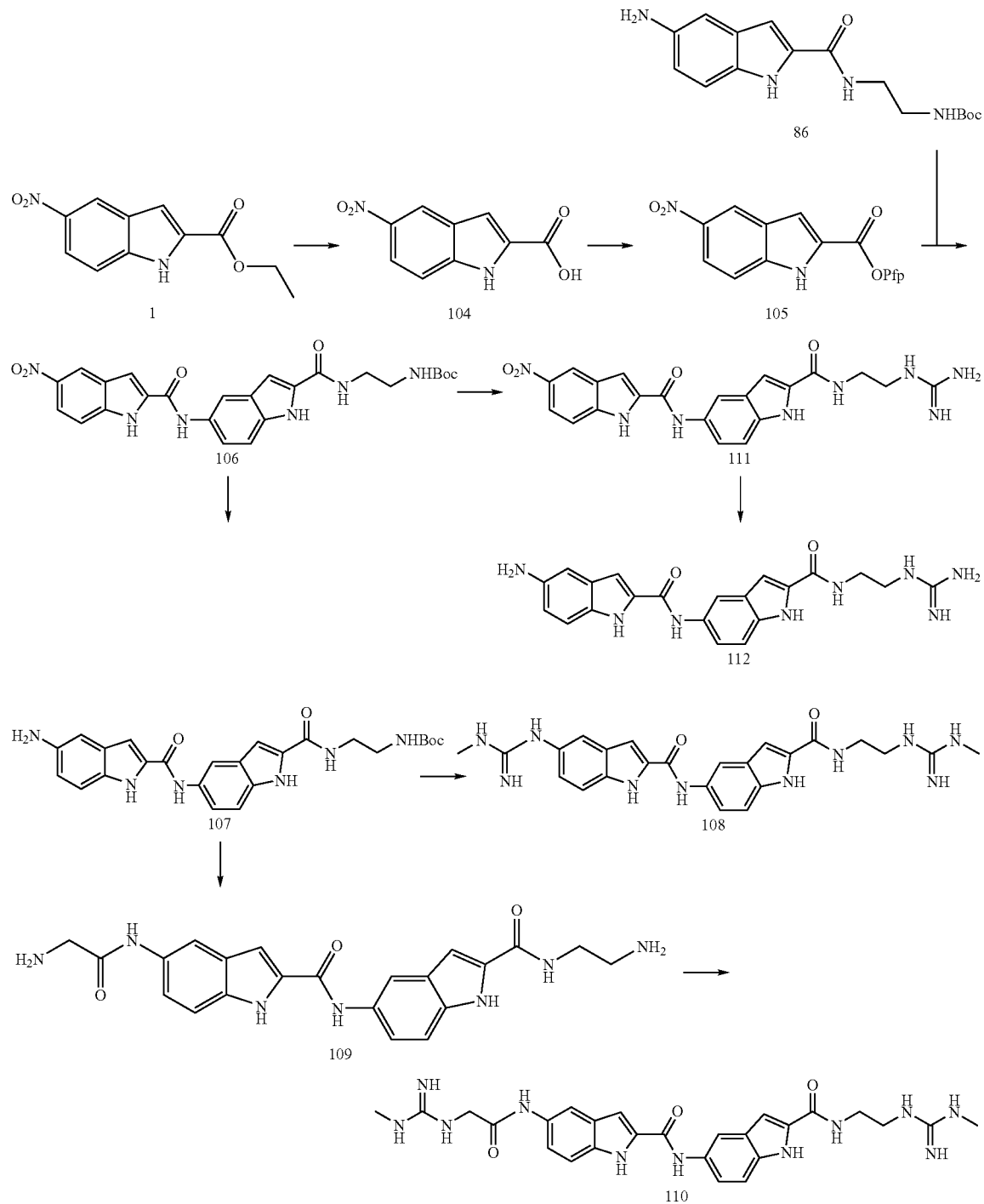
Scheme 6
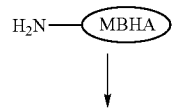
Scheme 7

-continued
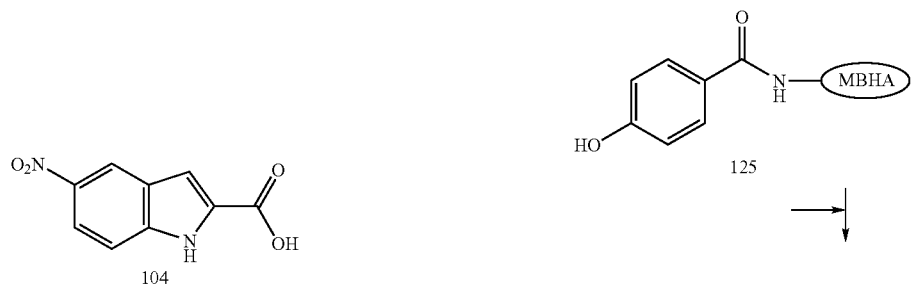
125
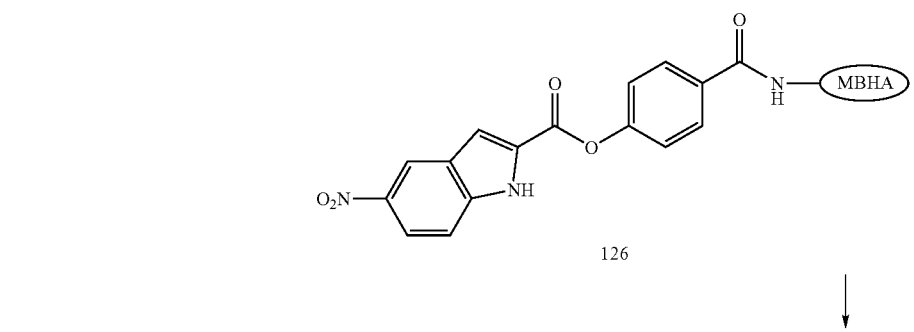
104
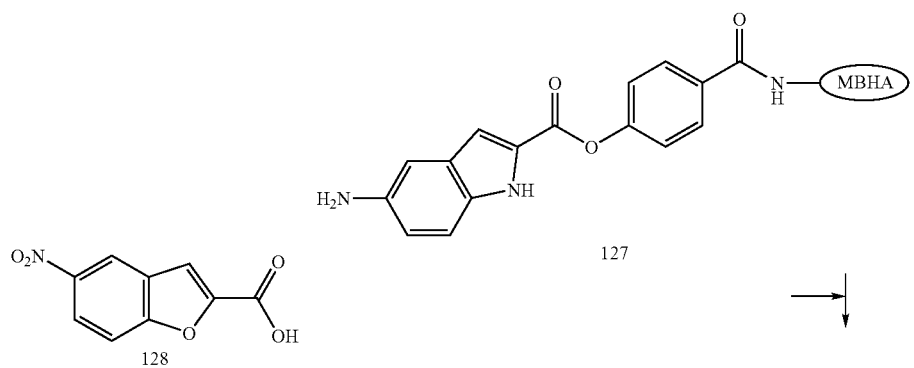
126
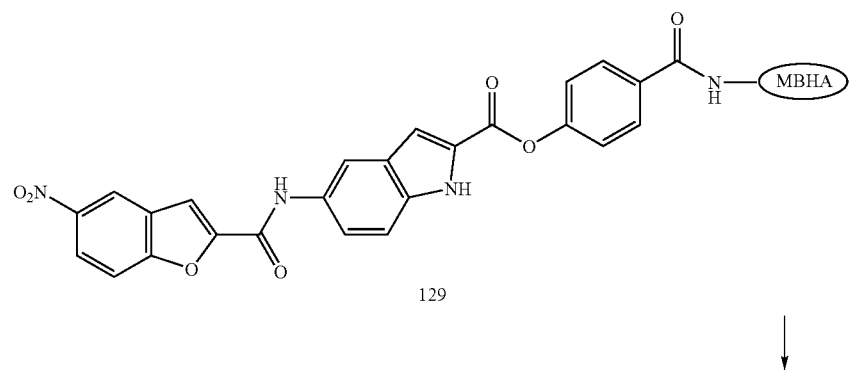
128
127
129

-continued
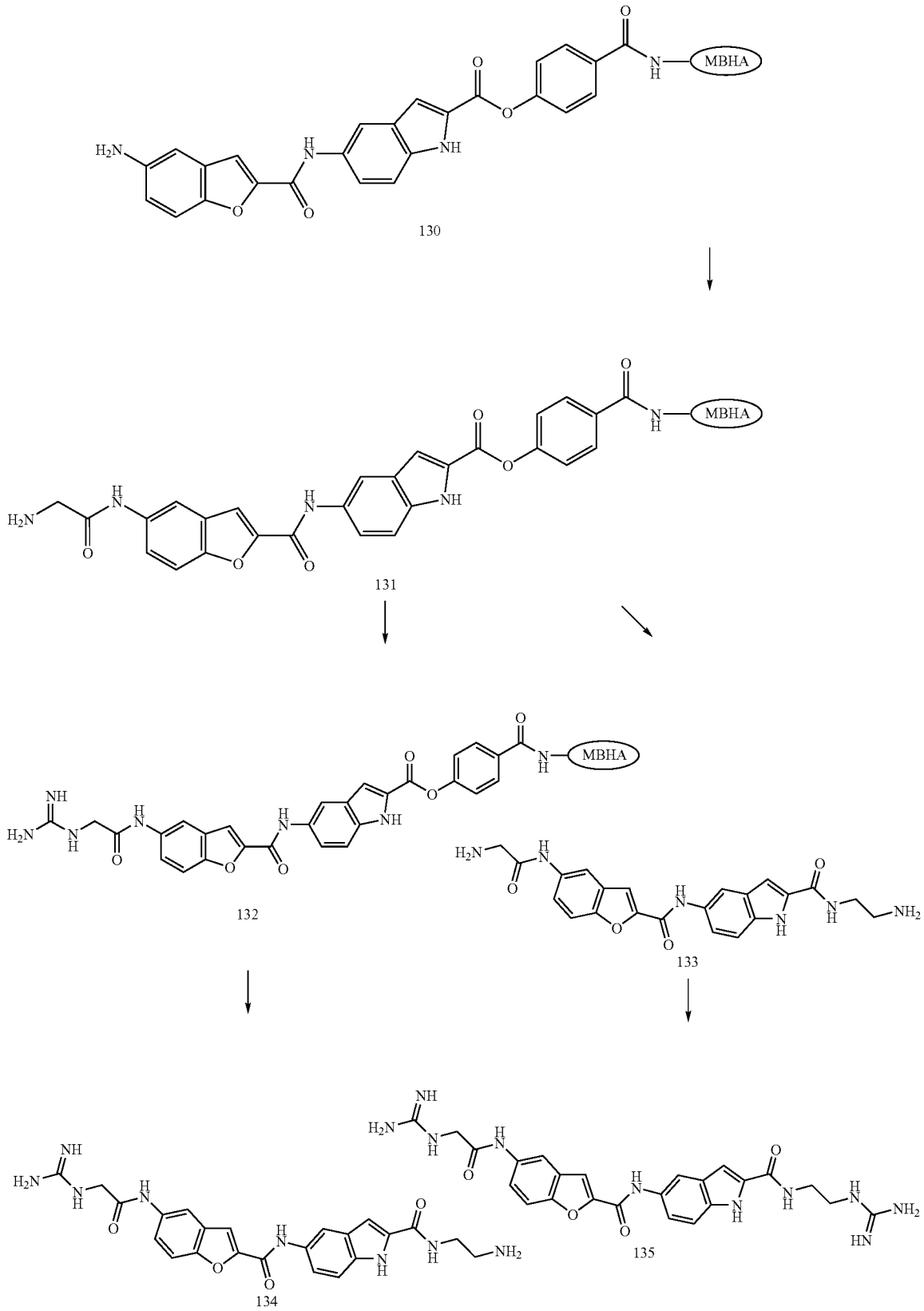

Scheme 8
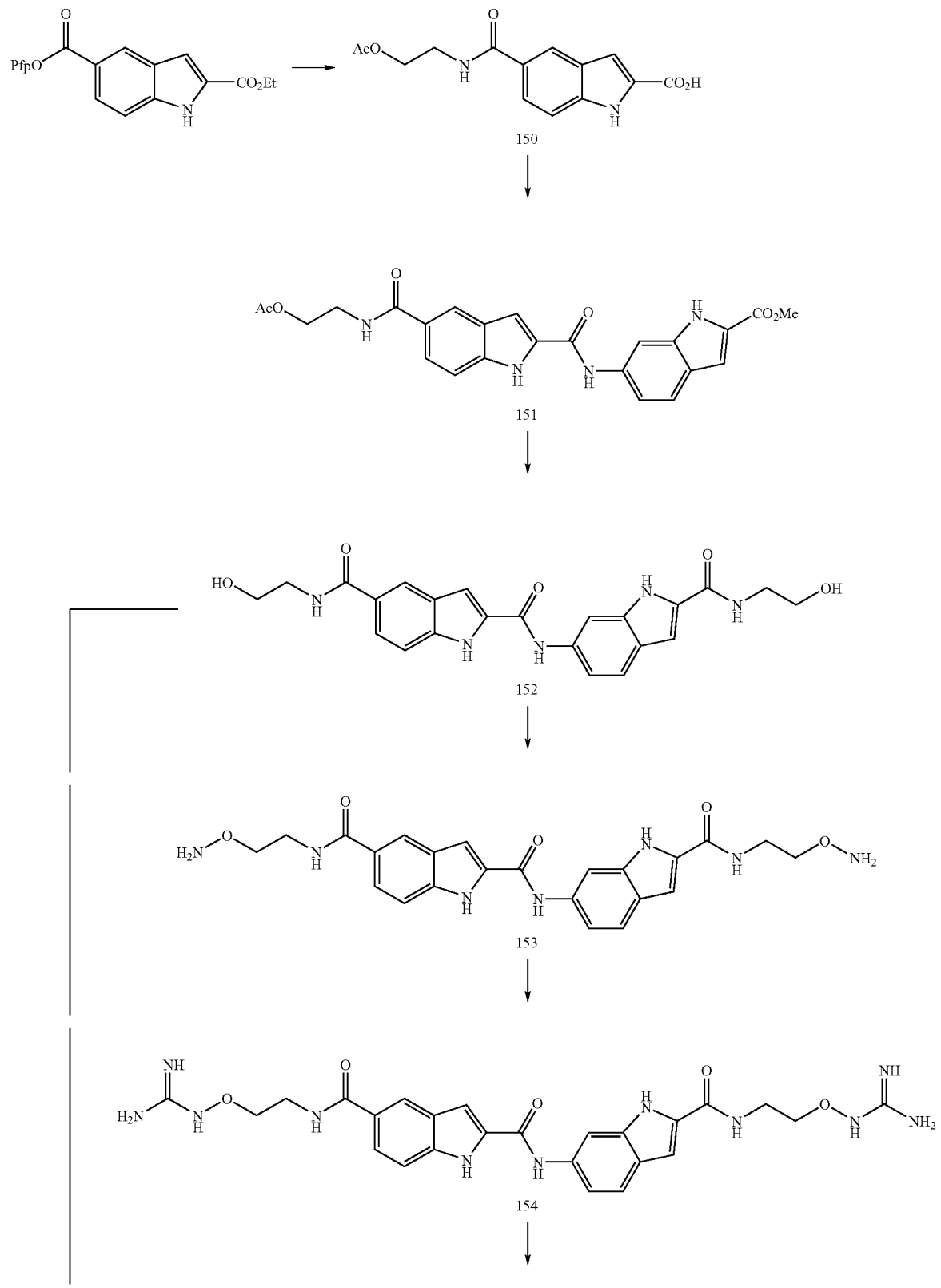

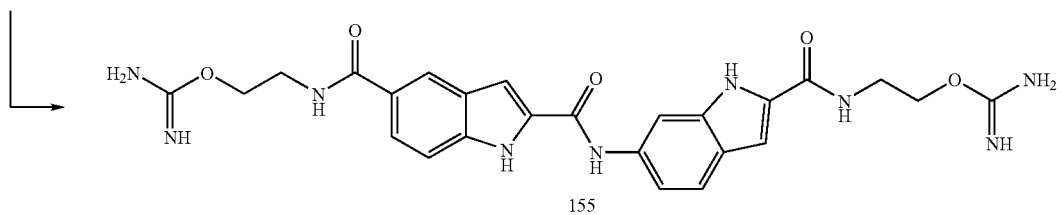
Scheme 9
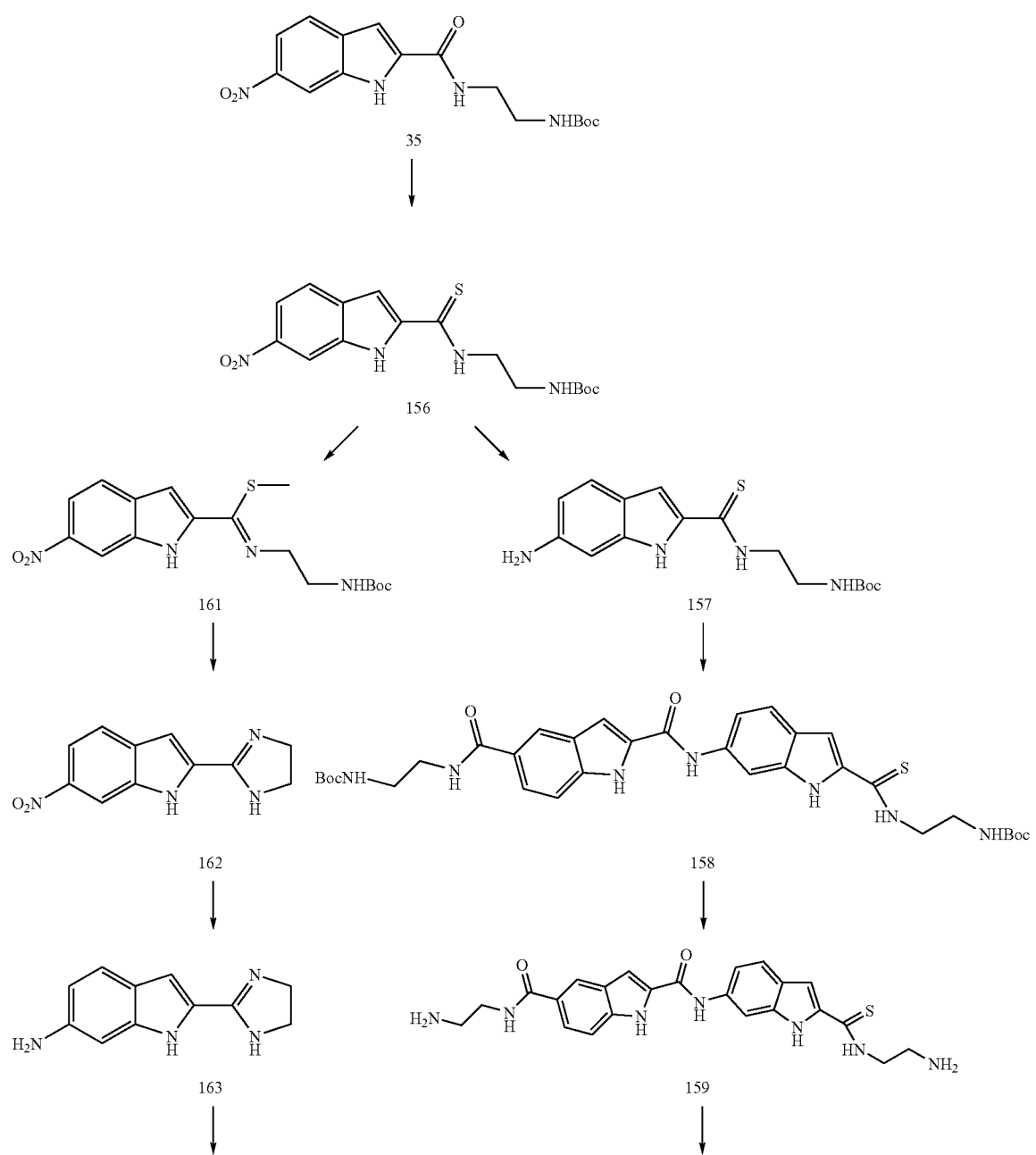

-continued
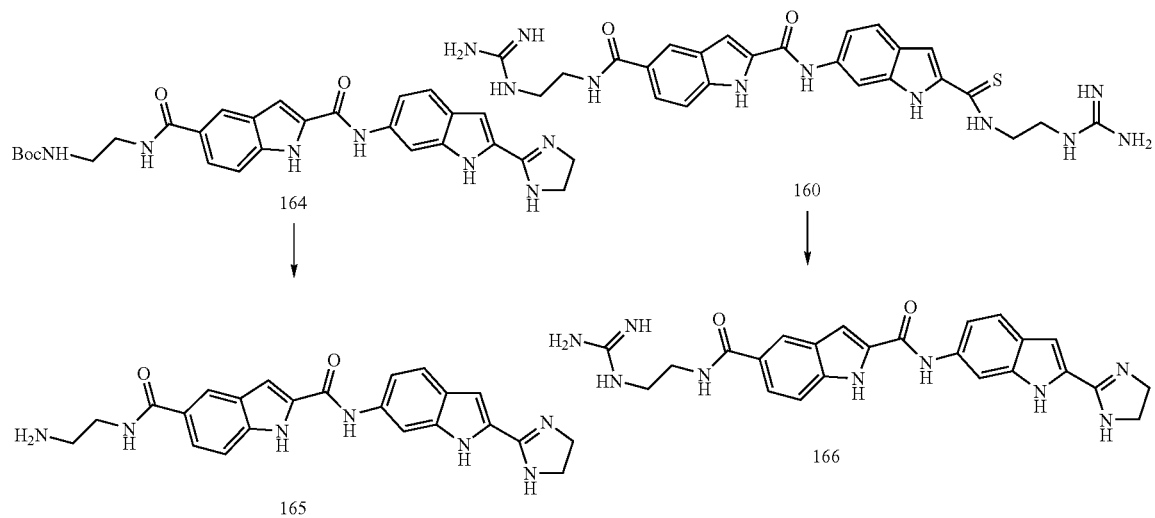
Scheme 10
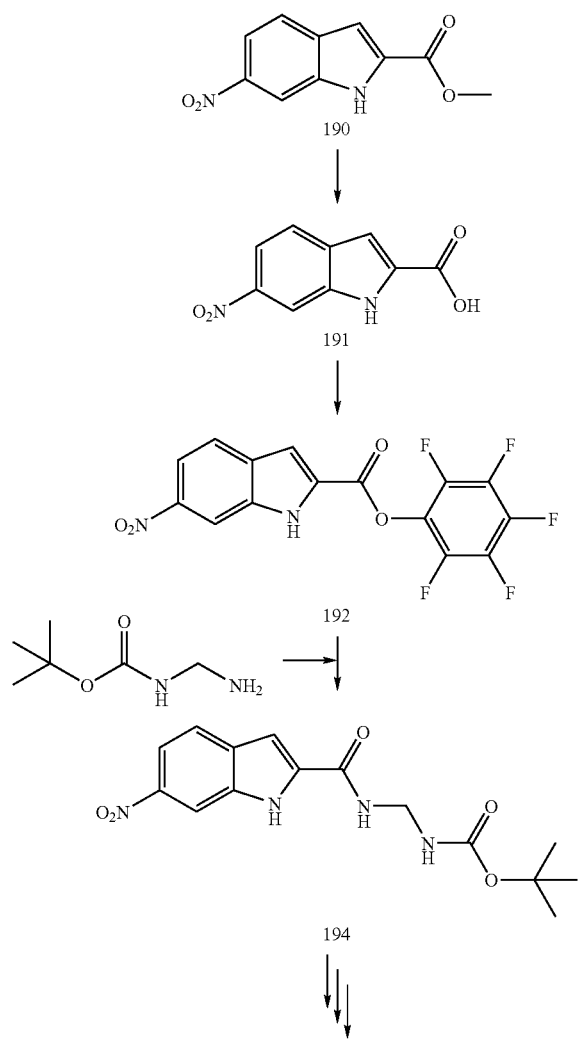

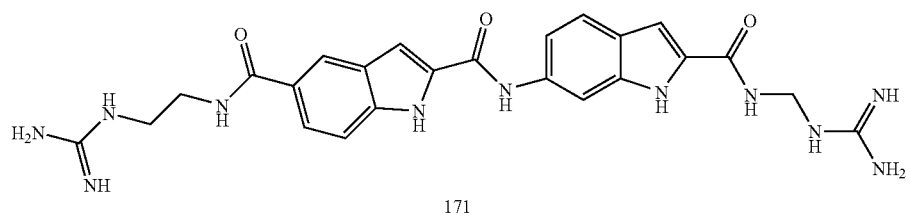
171
Scheme 11
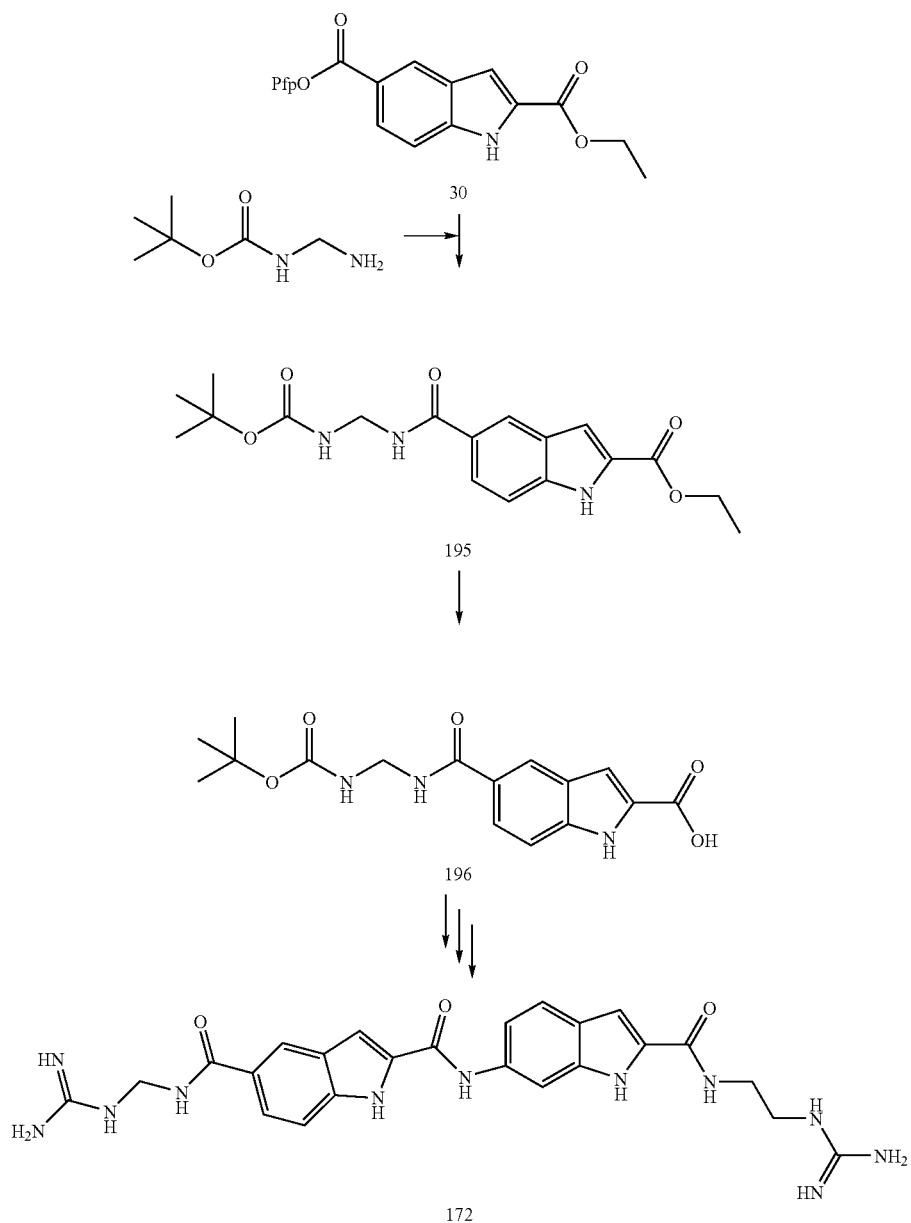
172

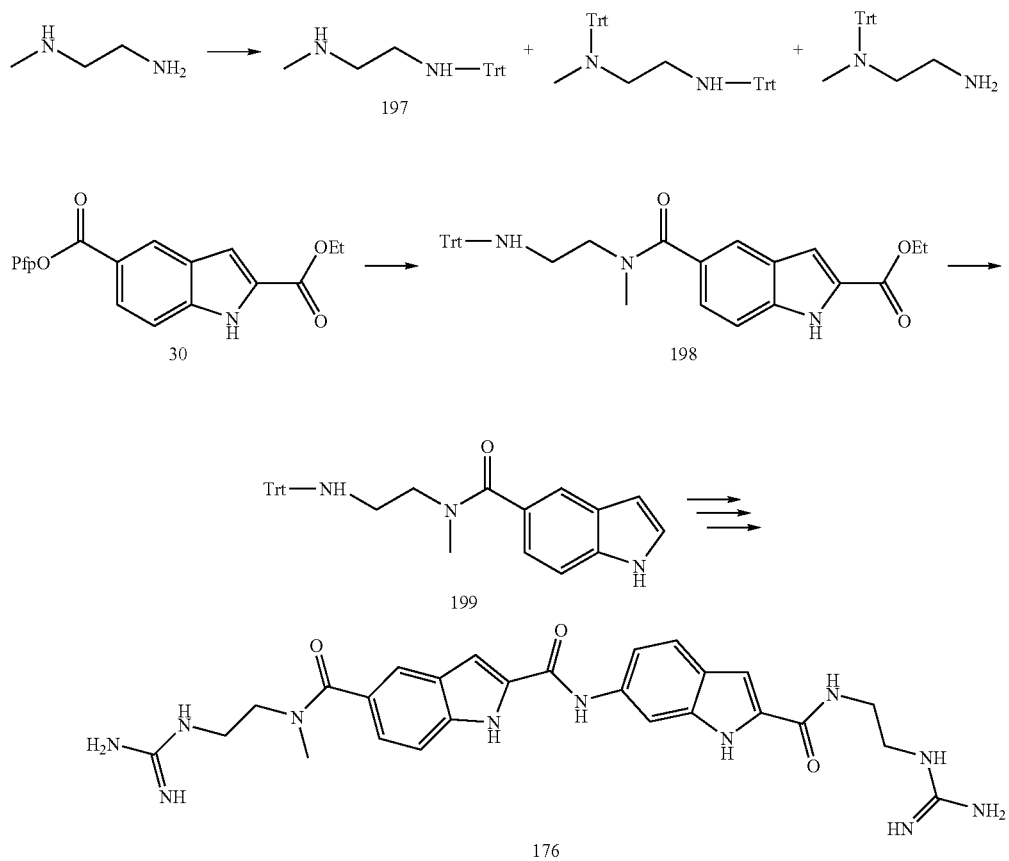

Scheme 12

Example 1

Synthesis of 1-H-Indole-2,5-dicarboxylic acid 2-ethyl ester 5-{[2-(ethoxycarbonyl)-1H-indol-5-yl]-amide}, 5

To a solution of 1 (7.02 g, 30.0 mmol, see Scheme 1) in EtOAc (60 mL) was added 10% Pd over activated carbon (2.0 g). The mixture was hydrogenated at 3540 psi for 30 min. The crude product was filtered through a bed of Celite, the Celite washed with EtOAc (100 ml) and the solvents removed in vacuo to give a 2 as a yellow solid, which was used without further purification in the coupling reaction. The activated acid 4 was prepared by slowly adding pentafluorophenyl trifluoroacetate (3.78 mL, 22.0 mmol) to a stirring solution of 3 (4.66 g, 20.0 mmol) in DMF (45 mL). The mixture was stirred at rt for 45 min. The crude product 4 was used without additional purification. The product of the reduction, 2, dissolved in DMF (25 mL) and diisopropylethylamine (3.84 mL, 22.0 mmol) were then added to the solution containing 4. The reaction mixture was heated at 55° C. for 6 h. The reaction mixture was then concentrated in vacuo, taken up in EtOAc (200 mL) and washed with water (100 mL), 0.1 N HCl (100 mL), and water (100 mL). The organic layer was dried over $Na_2SO_4$, filtered, and concentrated in vacuo to give 8.86 g of the crude product 5 as dense brown oil. The product was used without additional purification.

Example 2

Synthesis of 1H-Indole-2,5-dicarboxylic acid 5-{[2-carboxyl-1H-indol-5-yl]-amide}, 6

5 (1.80 g, 4.29 mmol) was dissolved in a solution of MeOH (80 mL) and aq. 2M NaOH (43 mL, 85.8 mmol) and heated at 65° C. for 45 min. MeOH was removed in vacuo, the mixture diluted with water (300 mL), cooled over ice, and brought to pH 1 with conc. HCl. The resulting precipitate was filtered, washed with water (100 mL), and dried with $P_2O_5$ to give 1.47 g (94%) of 6 as a light yellow solid. MS: 180.54 ([M-2H$^+$]/2).

Example 3

Synthesis of 1H-Indole-2,5-dicarboxylic acid 2-[2-amino-ethyl)-amide] 5-{[2-(2-amino-ethylcarbanzoyl)-1H-indol-5-yl]-amide), 8

5 (210 mg, 0.5 mmol) was dissolved in neat 1,2-ethylenediamine (2 mL) and heated at 55° C. overnight. Ethylenediamine was removed in vacuo and the residue co-evaporated 1× with DMF. The residue was taken up in MeOH (5 mL) and precipitated with ether (45 mL). The precipitate was washed 1× with ether (50 mL), dried, and the residue purified on a reverse-phase HPLC column to give 8 as its bis-TFA salt. The product was taken up in MeOH (4 mL) and treated with 1 mL 4.0M HCl in dioxane, precipitated with ether, washed 1× with ether, and dried to 8 as its bis-HCl salt. Yield: 33% of Compound 8. MS: 224.59 ([M+2H$^+$]/2). $^1$H-NMR (DMSO-d$_6$) 11.93 (s, 1H), 11.59 (s, 1H), 10.05 (s, 1H), 8.91 (t, 1H), 8.34 (s, 1H), 8.09 (s, 1H), 8.02 (br s, 6H), 7.81 (d, 1H), 7.48 (d, 2H), 7.36 (d, 2H), 7.13 (s, 1H), 3.53 (t, 4H), 2.99 (m, 4H).

Example 4

Synthesis of 1H-Indole-2,5-dicarboxylic acid 2-[2-acetimidoylamino-ethyl)-amide] 5-{[2-(2-acetimidoylamino-ethylcarbamoyl)-1H-indol-5-yl]-amide}, 9

To a solution of 8 (30 mg, 0.058 mmol) in DMF (2 mL) was added ethyl acetimidate hydrochloride (140 mg, 1.15 mmol) and diisopropylethylamine (300 μL, 1.74 mmol). The reaction mixture was stirred at rt under Ar for 48 h. The reaction mixture was then concentrated in vacuo, taken up in MeOH (5 mL), and the product precipitated with ether (45 mL). The precipitate was washed 1× with ether (50 mL), dried, and the residue purified on a reverse-phase HPLC column to give 9 as its bis-TFA salt. The product was taken up in MeOH (4 mL) and treated with 1 mL 4.0M HCl in dioxane, precipitated with ether, washed 1× with ether, and dried to give 9 as its bis-HCl salt. Yield: 23% of Compound 9. MS: 265.69 ([M+2H$^{30}$ ]/2). $^1$H-NMR (DMSO-d$_6$) 11.98 (s, 1H), 11.6 (s, 1H), 10.07 (s, 1H), 9.7 (br s, 2H), 9.21 (s 2H), 9.0 (t, 1H), 8.6–8.4 (m, 3H), 8.36 (s, 1H), 8.11 (s, 1H), 7.85 (D, 1H), 7.51 (m, 2H), 7.38 (s, 1H), 7.36 (s, 1H), 7.15 (s, 1H), 3.55–3.4 (m, 8H), 2.15 (s, 6H).

Example 5

Synthesis of 1H-Indole-2,5-dicarboxylic acid 2-[(2-gutanidino-ethyl)-amide] 5-{[2-(2-guanidino-ethyl-carbamoyl)-1H-indol-5-yl]-amide}, 10

To a solution of 8 (35 mg, 0.067 mmol) in DMF (2 mL) was added pyrazole-1-carboxamidine hydrochloride (150 mg, 1.34 mmol) and diisopropylethylamine (250 μL, 1.34 mmol). The reaction mixture was stirred at rt under Ar for 24 h. The reaction mixture was then concentrated in vacuo, taken up in MeOH (5 mL), and the product precipitated with ether (45 mL). The precipitate was washed 1× with ether (50 mL), dried, and the residue purified on a reverse-phase HPLC column to give 10 as its bis-TFA salt. The product was taken up in MeOH (4 mL) and treated with 1 mL 4.0M HCl in dioxane, precipitated with ether, washed 1× with ether, and dried to give 10 as its bis-HCl salt. Yield: 25% of Compound 10. MS: 266.69 ([M+2H$^+$]/2). $^1$H-NMR (DMSO-d$_6$) 11.95 (s, 1H), 11.4 (s, 1H), 10.11 (s, 1H), 8.91 (t, 1H), 8.75 (t, 1H), 8.36 (s, 1H), 8.1 (s, 1H), 7.86–7.74 (m, 3H), 7.54–7.47 (m, 3H), 7.14 (s, 2H).

Example 6

Synthesis of 1H-Indole-2,5-dicarboxylic acid 2-[3-amino-2-hydroxy-propyl)-amide] 5-{[2-(3-amino-2-hydroxy-propylcarbamoyl)-1H-indol-5-yl]-amide}, 11

Compound 11 was synthesized as described for Compound 8 in Example 1 through Example 3, except instead of 1,2-ethylenediamine, 1,3-diamino-2-hydroxypropane was used. Yield: 29% of Compound 11. MS: 254.59 (M+2H$^+$).

Example 7

Synthesis of 1H-Indole-2,5-dicarboxylic acid 2-[(5-amino-pentyl)-amide] 5-{[2-(5-amino-pentylcarbamoyl)-1H-indol-5-yl]-amide}, 12

Compound 12 was synthesized as described for Compound 8 in Example 1 through Example 3, except instead of 1,2-ethylenediamine, 1,5-diaminopentane was used. Yield: 25% of Compound 12. MS: 266.62 ([M+2H$^+$]/2). $^1$H-NMR (DMSO d$_6$) 11.88 (s, 1H), 11.52 (s, 1H), 10.04, (s, 1H), 8.65 (t, 1H), 8.49 (t, 1H), 8.32 (s, 1H), 8.08 (s, 1H), 8.00–7.70 (m, 7H), 7.47 (d, 2H), 7.35 (d, 1H), 7.27 (s, 1H), 7.08 (s, 1H), 3.40–3.10 (m, 4H), 2.85–2.60 (m, 4H), 1.70–1.50 (m, 8H), 1.45–1.30 (m, 4H).

Example 8

Synthesis of 1H-Indole-2,5-dicarboxylic acid 2-{[2-(2-amino-ethylamino)-ethyl]-amide} 5-{[2-2-(2-amino-ethylamino)-ethylcarbamoyl]-1H-indol-5-yl}-amide), 13

Compound 13 was synthesized as described for Compound 8 in Example 1 through Example 3, except instead of 1,2-ethylenediamine, diethylenetriamine was used. Yield: 25% of Compound 13. MS: 267.62 ([M+2H$^+$]/2). $^1$H-NMR (DMSO d$_6$) 11.94 (s, 1H), 11.60 (s, 1H), 10.06 (s, 1H), 9.49 (bs, 4H), 8.98 (t, 1H), 8.82 (t, 1H), 8.36 (s, 1H), 8.28 (bs, 6H), 8.11 (d, 1H), 7.82 (dd, 1H), 7.55–7.45 (m, 2H), 7.42–7.35 (m, 2H), 7.19 (dd, 1H), 3.70–3.55 (m, 4H), 3.30–3.10 (m, 12H).

Example 9

Synthesis of 1H-Indole-2,5-dicarboxylic acid 2-[(4-aminomethyl-cyclohexylmethyl)-amide] 5-{42-[(4-aminomethyl-cyclohexylmethyl)-carbamoyl]-1H-indol-5-yl}-amide), 14

The activated acid 7 was prepared by slowly adding pentafluorophenyl trifluoroacetate (378 μL, 2.20 mmol) to a stirring solution of 6 (363 mg, 1.00 mmol) in DMF (10 mL). The mixture was stirred at rt for 45 min. To this solution was added 1,4-cyclohexanebis(methylamine) (755 μL, 5.00 mmol). The mixture was stirred for 5 min. The reaction mixture was then concentrated in vacuo, taken up in MeOH (5 mL), and the product precipitated with ether (45 mL). The precipitate was washed 1× with ether (50 mL), dried, and the residue purified on a reverse-phase HPLC column to give 14 as its bis-TFA salt. The product was taken up in MeOH (4 mL) and treated with 1 mL 4.0M HCl in dioxane, precipitated with ether, washed 1× with ether, and dried to give 14 as its bis-HCl salt. Yield: 25% of Compound 14. MS: 306.67 ([M+2H$^+$]/2). $^1$H-NMR (DMSO d$_6$) 11.87 (s, 1H), 11.52 (s, 1H), 10.05 (s, 1H), 8.61 (t, 1H), 8.46 (t, 1H), 8.33 (s, 1H), 8.08 (s, 1H), 8.02–7.95 (m, 7H), 7.48 (d, 2H), 7.36 (d, 1H), 7.28 (s, 1H), 7.10 (s, 1H), 3.30–3.20 (m, 3H), 3.19–3.09 (1H), 2.85–2.70 (m, 3H), 2.68–2.58 (m, 1H), 1.90–1.65 (m, 6H), 1.60–1.30 (m, 12H), 1.00–0.80 (m, 2H).

Example 10

Synthesis of 1H-Indole-2,5-dicarboxylic acid 2-[(4-amino-cyclohexyl)-amide] 5-{[2-(4-amino-cyclo-hexylcarbomyl)-1H-indol-5-yl]-amide}, 15

Compound 15 was synthesized as described for Compound 14 in Example 1 through Example 9, except instead of 1,4-cyclohexanebis(methylamine), trans-1,4-diaminocyclohexane was used. Yield: 17% of Compound 15. MS: 278.62 ([M+2H$^+$]/2). $^1$H-NMR (DMSO d$_6$) 11.86 (s, 1H), 11.52 (s, 1H), 10.04 (s, 1H), 8.44 (s, 1H), 8.35–8.25 (m, 2H), 8.07 (s, 1H), 7.97 (bs, 6H), 7.81 (d, 1H), 7.48 (d, 2H), 7.36 (d, 1H), 7.29 (s, 1H), 7.11 (s, 1H), 3.85–3.65 (m, 2H), 3.10–2.90 (m, 3H), 2.05–1.85 (m, 8H), 1.55–1.35 (m, 7H).

Example 11

Synthesis of 1H-Indole-2,5-dicarboxylic acid 2-[(3-aminomethyl-cyclohexylmethyl)-amide] 5-({2-[(3-aminomethyl-cyclohexylmethyl)-carbamoyl]-1H-indol-5-yl}-amide), 16

Compound 16 was synthesized as described for Compound 14 in Example 1 through Example 9, except instead of 1,4-cyclohexanebis(methylamine), 1,3-cyclohexanebis(methylamine) was used. Yield: 17% of Compound 16. MS: 306.67 ([M+2H$^+$]/2). $^1$H-NMR (DMSO d$_6$) 11.89 (s, 1H), 11.53 (s, 1H), 10.51 (s, 1H), 8.63 (t, 1H), 8.48 (t, 1H), 8.33 (s, 1H), 8.08 (s, 1H), 8.02–7.70 (m, 6H), 7.82 (d, 1H), 7.48 (d, 2H), 7.36 (d, 1H), 7.29 (s, 1H), 7.10 (s, 1H), 3.25–3.10 (m, 4H), 2.80–2.55 (m, 4H), 1.90–1.70 (m, 6H), 1.68–1.36 (m, 6H), 1.34–1.16 (m, 3H), 0.98–0.76 (m, 3H), 0.74–0.56 (m, 2H).

Example 12

Synthesis of 1H-Indole-2,5-dicarboxylic acid 2-[3-morpholin-4-yl-propyl)-amide] 5-{[2-(3-morpholin-4-yl-propylcarbamoyl)-1H-indol-5-yl]-amide}, 17

Compound 17 was synthesized as described for Compound 14 in Example 1 through Example 9, except instead of 1,4-cyclohexanebis(methylamine), 3-morpholinopropylamine was used. Yield: 41% of Compound 17. MS: 308.63 ([M+2H$^+$]/2). $^1$H-NMR (DMSO d$_6$) 11.94 (s, 1H), 11.58 (s, 1H), 10.78 (bs, 2H), 10.06 (s, 1H), 8.87 (t, 1H), 8.72 (t, 1H), 8.35 (s, 1H), 8.10 (s, 1H), 7.82 (dd, 1H), 7.56–7.44 (m, 2H), 7.36 (d, 1H), 7.30 (d, 1H), 7.10 (d, 1H), 4.00–3.88 (m, 4H), 3.84–3.70 (m, 4H), 3.50–3.38 (m, 8H), 3.20–3.08 (m, 8H), 2.05–1.90 (m, 4H).

Example 13

Synthesis of 1H-Indole-2,5-dicarboxylic acid 2-[(4-guanidinomethyl-cyclohexylmethyl)-amide] 5-({2-[(4-guanidinomethyl-cyclohexylmethyl)-carbamoyl}-1H-indol-5-yl}-amide), 18

18 was prepared from 14 as described for Compound 10 in Example 5. Yield: 19% of Compound 18. MS: 348.78 ([M+2H$^+$]/2). $^1$H-NMR (DMSO d$_6$) 11.87 (s, 1H), 11.52 (s, 1H), 10.05 (s, 1H), 8.60 (t, 1H), 8.46 (t, 1H), 8.33 (s, 1H), 8.08 (s, 1H), 7.82 (dd, 1H), 7.78–7.62 (m, 2H), 7.60–6.70 (m, 13H), 3.40–2.90 (m, 12H), 1.90–1.30 (m, 16H).

Example 14

Synthesis of 1H-Indole-2,5-dicarboxylic acid 2-[(3-guanidino-2-hydroxy-propyl)-amide] 5-{[2-(3-guanidino-2-hydroxy-propylcarbamoyl)-1H-indol-5-yl]-amide}, 19

Compound 19 was synthesized as described for Compound 18 in Example 1 through Example 13, except instead of 1,4-cyclohexanebis(methylamine), 1,3-diamino-2-hydroxypropane was used. Yield: 26% of Compound 19. MS: 296.70 ([M+2H$^+$]/2). $^1$H-NMR (DMSO d$_6$) 11.91 (s, 1H), 11.56 (s, 1H), 10.06 (s, 1H), 8.74 (t, 1H), 8.57 (t, 1H), 8.34 (s, 1H), 8.10 (s, 1H), 7.82 (dd, 1H), 7.60–6.60 (m, 15H), 5.56 (bs, 2H), 3.90–3.75 (m, 2H), 3.34–3.22 (m, 6H), 3.20–3.15 (m, 2H).

Example 15

Synthesis of 1H-Indole-2,5-dicarboxylic acid 2-[(5-guanidino-pentyl)-amide] 5-{[2-(5-guanidino-pentylcarbanzoyl)-1H-indol-5-yl]-amide}, 20

Compound 20 was synthesized as described for Compound 18 in Example 1 through Example 13, except instead of 1,4-cyclohexanebis(methylamine), diaminopentane was used. Yield: 34% of Compound 20. MS: 308.66 ([M+2H$^+$]/2). $^1$H-NMR (DMSO d$_6$) 11.92 (s, 1H), 11.56 (s, 1H), 10.07 (s, 1H), 8.73 (t, 1H), 8.57 (t, 1H), 8.34 (s, 1H), 8.24–7.94 (m, 3H), 7.90–7.76 (m, 3H), 7.70–6.74 (m, 1H), 3.34–3.22 (m, 4H), 3.16–3.03 (m, 4H), 1.68–1.26 (m, 12H).

Example 16

Synthesis of 1H-Indole-2,5-dicarboxylic acid 2-[(4-guanidino-cyclohexyl)-amide] 5-{[2-(4-guaizidino-cyclohexylcarbamoyl)-1H-indol-5-yl]-amide}, 21

Compound 21 was synthesized as described for Compound 18 in Example 1 through Example 13, except instead of 1,4-cyclohexanebis(methylamine), trans-1,4-diaminocyclohexane was used. Yield: 20% of Compound 21. MS: 320.66 ([M+2H$^+$]/2). $^1$H-NMR (DMSO d$_6$) 11.87 (s, 1H), 11.52 (s, 1H), 10.04 (s, 1H), 8.44 (t, 1H), 8.36–8.26 (m, 2H), 8.07 (s, 1H), 7.81 (dd, 1H), 7.70–6.50 (m, 15H), 3.87–3.69 (m, 2H), 3.35–3.30 (m, 2H), 2.00–1.80 (m, 8H), 1.60–1.20 (m, 8H).

Example 17

Synthesis of 1H-Indole-2,5-dicarboxylic acid 2-(4-guanidinomethyl-benzylamide) 5-{[2-(4-guanidinomethyl-benzylcarbamoyl)-1H-indol-5-yl]-amide}, 22

Compound 22 was synthesized as described for Compound 18 in Example 1 through Example 13, except instead of 1,4-cyclohexanebis(methylamine), p-xylenediamine was used. Yield: 19% of Compound 22. MS: 342.65 ([M+2H$^+$]/2). $^1$H-NMR (DMSO d$_6$) 11.93 (s, 1H), 11.58 (s, 1H), 10.07 (s, 1H), 9.24 (t, 1H), 9.09 (t, 1H), 8.35 (s, 1H), 8.16–8.04 (m, 3H), 7.83 (dd, 1H), 7.60–6.90 (m, 21H), 4.56–4.44 (m, 4H), 4.40–4.30 (m, 4H).

Example 18

Synthesis of 1H-Indole-2,5-dicarboxylic acid 2-{[4-(acetimidoylamino-methyl)-cyclohexylmethyl]-amide} 5-[(2-{[4-(acetimidoylamino-methyl)-cyclohexylmethyl]-carbamoyl}-1H-indol-5-yl)-amide], 23

23 was prepared from 14 as described for Compound 9 in Example 4. Yield: 18% of Compound 23. MS: 347.81 ([M+2H$^+$]/2). $^1$H-NMR (DMSO d$_6$) 11.89 (s, 1H), 11.53 (s, 1H), 10.05 (s, 1H), 9.65–9.40 (m, 2H), 9.20–9.05 (m, 2H), 8.80–8.40 (m, 4H), 8.33 (s, 1H), 8.08 (s, 1H), 7.82 (d, 1H), 7.60–7.44 (m, 2H), 7.36 (d, 1H), 7.29 (s, 1H), 7.10 (s, 1H), 3.30–3.00 (m, 8H), 2.15 (s, 6H), 1.90–1.65 (6H), 1.60–1.30 (m, 12H), 1.15–0.85 (m, 2H).

Example 19

Synthesis of 1H-Indole-2,5-dicarboxylic acid 2-[(3-guanidinomethyl-cyclohexylmethyl)-amide] 5-({2-[(3-guanidinomethyl-cyclohexylmethyl)-carbamoyl}-1H-indol-5-yl}-amide), 24

Compound 24 was synthesized as described for Compound 18 in Example 1 through Example 13, except instead of 1,4-cyclohexanebis(methylamine), 1,3-cyclohexanebis (methylamine) was used. Yield: 37% of Compound 24. MS: 348.78 ([M+2H$^+$]/2). $^1$H-NMR (DMSO d$_6$) 11.89 (s, 1H), 11.53 (s, 1H), 10.05 (s, 1H), 8.66 (t, 1H), 8.51 (t, 1H), 8.34 (s, 1H), 8.08 (s, 1H), 7.82 (dd, 1H), 7.76–7.64 (m, 2H), 7.60–6.60 (m, 13H), 3.30–2.70 (m, 8H), 2.00–1.10 (m, 16H), 1.00–0.50 (m, 4H).

Example 20

Synthesis of 1H-Indole-2,5-dicarboxylic acid 2-(3-guanidinomethyl-benzylamide) 5-{[2-(3-guanidinomethyl-benzylcarbamoyl)-1H-indol-5-yl]-amide}, 25

Compound 25 was synthesized as described for Compound 18 in Example 1 through Example 13, except instead of 1,4-cyclohexanebis(methylamine), m-xylenediamine was used. Yield: 39% of Compound 25. MS: 342.66 ([M+2H$^+$]/2). $^1$H-NMR (DMSO d$_6$) 11.95 (s, 1H), 11.59 (s, 1H), 10.07 (s, 1H), 9.26 (t, 1H), 9.11 (t, 1H), 8.36 (s, 1H), 8.20–8.04 (m, 3H), 7.83 (dd, 1H), 7.80–6.60 (m, 211H), 4.60–4.46 (m, 4H), 4.42–4.32 (m, 4H).

Example 21

Synthesis of {2-[(1-Isobutyl-4-nitro-1H-pyrrole-2-carbonyl)-amino]-ethyl}-carbamic acid tert-butyl ester, 26

1-Isobutyl-4-nitro-1H-pyrrole-2-carboxylic acid ethyl ester (Dyatkina et al., *J. Med. Chem.*, 45(4):805–817, 2002) was reacted with ethylenediamine, followed by Boc-protection according to the procedure for Compound 35 in Example 30 to give compound 26 in quantitative yield. $^1$H-NMR (DMSO-d$_6$): 8.35 (t, 1H), 8.15 (s, 1H), 7.40 (s, 1H), 6.88 (t, 1H), 4.20 (d, 2H), 3.20 (q, 2H), 3.05 (q, 2H), 1.98 (m, 1H), 1.19 (s, 9H), 0.77 (d, 6H).

Example 22

Synthesis of 5-[5-(2-tert-Butoxycarbonylamino-ethylcarbamoyl)-1-isobutyl-1H-pyrrol-3-yl-carbamoyl]-1H-indole-2-carboxylic acid ethyl ester, 27

Compound 27 was synthesized as described for Compound 5 in Example 1, except instead of Compound I, Compound 26 was used. Yield: 86%.

Example 23

Synthesis of {2-[(4-{[2-(2-Amino-ethylcarbamoyl)-1H-indole-5-carbonyl]-amino}-1-isobutyl-1H-pyrrole-2-carbonyl)-amino]-ethyl}-carbamic acid tert-butyl ester, 28

Compound 28 was synthesized from 27 as described for Compound 8 in Example 3. Yield: 89%.

Example 24

Synthesis of 1H-indole-2,5-dicarboxylic acid 2-[(2-guanidino-ethyl)-amide] 5-{[5-(2-guanidino-ethyl-carbamoyl)-1-isobutyl-1H-pyrrol-3-yl]-amide}, 29

Compound 28 was treated with TFA/anisole to give its bis-amine, followed by guanidylation with 1H-pyrazole-1-carboxamidine hydrochloride as described for Compound 10 in Example 5 to give Compound 29. Yield: 26%. MS: 269.67 ([M+2H$^+$]/2). $^1$H-NMR (DMSO-d$_6$): 11.91 (s, 1H), 10.24 (s, 1H), 8.91 (t, 1H), 8.30 (s, 1H), 8.17 (t, 1H), 7.80 (d, 1H), 7.66 (m, 2H), 7.45 (d, 1H), 7.34 (s, 1H), 7.29 (s, 1H), 6.97 (d, 1H), 4.10 (d, 2H), 3.42–3.25 (m, 8H), 1.95 (m, 1H), 0.80 (d, 6H).

Example 25

Synthesis of 1H-Indole-2,5-dicarboxylic acid 2-ethyl ester 5-pentafluorophenyl ester, 30

To a solution of compound 3 (1.8 g, 7.72 mmol) in DMF (50 ml) in the presence of triethylamine (1.18 ml, 8.49 mmol) was added pentafluorophenyl trifluoroacetate (1.46 ml, 8.49 mmol) dropwise in 5 min at 0° C. The reaction mixture was then stirred at room temperature overnight. After evaporation of solvent, the residue was dissolved in EtOAc and the organic phase was washed with water (50 ml×3) and dried over Na$_2$SO$_4$. The compound was purified by chromatography using toluene-EtOAc (35:1) as eluent to give a powder (1.68 g, 55%). MS: 422.04 (M+Na$^+$). $^1$H NMR (DMSO-d$_6$) 8.66 (s, 1H), 8.00 (d, 1H), 7.64 (d, 1H), 7.40 (s, 1H), 4.36 (q, 2H), 1.34 (t, 3H).

Example 26

Synthesis of 5-(2-tert-Butoxycarbonylamino-ethylcarbamoyl)-1H-indole-2-carboxylic acid ethyl ester, 31

A mixture of compound 30 (0.2 g, 0.5 mmol), (2-aminoethyl)-carbamic acid tert-butyl ester (84.3 mg, 0.53 mmol) and DIEA (0.1 ml, 0.6 mmol) in DMF (10 ml) was stirred at room temperature for 2 h. Analytical HPLC showed the reaction was completed. After evaporation of solvent, the crude compound 31 was obtained and used with no further purification. MS: 376.15 ((M+H$^+$).

Example 27

Synthesis of 5-(2-tert-Butoxycarbonylamino-ethylcarbamoyl)-1H-indole-2-carboxylic acid, 32

Compound 31 was dissolved in MeOH (20 ml) and 2 M aqueous NaOH (10 ml) was added. The reaction mixture was stirred at room temperature for 2 h until no compound 31 was detected by TLC. The reaction solution was evaporated to about 8 ml and adjusted to pH 3 with 2 M HCl. The precipitates formed were collected by filtration or centrifugation, washed with water and dried under high vacuum to give a white powder (0.158 g) in total yield of 91%. MS 346.23 (M−H$^+$). $^1$H NMR (DMSO-d$_6$) 11.95 (s, 1H), 8.36 (t, 1H), 8.18 (s, 1H), 7.72 (d, 1H), 7.41 (d, 1H), 7.15 (s, 1H), 6.91 (t, 1H), 3.29 (q, 2H), 3.10 (q, 2H), 1.37 (s, 9H).

Example 28

Synthesis of 5-(2-tert-Butoxycarbonylamino-ethylcarbamoyl)-1H-indole-2-carboxylic acid pentafluorophenyl ester, 33

To a solution of compound 32 (0.154 g, 0.44 µmol) in DMF (5 mL) in the presence of DIEA (93 ml, 0.53 mmol) was added dropwise pentafluorophenyl trifluoroacetate (92 µl, 0.53 mmol) at 0° C. The resulting reaction mixture was stirred at room temperature overnight. HPLC showed that the reaction was completed. The solvent was then evaporated to dryness, and the residue was carefully washed with ether to give compound 33 in quantitative yield.

Example 29

Synthesis of 6-Nitro-1H-indole-2-carboxylic acid methyl ester, 34

Compound 34 was prepared from indoline-2-carboxlic acid by nitration with nitric acid in sulfuric acid, methylation using methanol and p-toluenesulfonic acid, followed by reaction with dichlorodicyanobenzoquinone in ethyl acetate and benzene. Total yield: 58%. MS: 219.13 (M−H$^+$).

Example 30

Synthesis of {2-[(6-Nitro-1H-indole-2-carbonyl)-amino]-ethyl}-carbamic acid tert-butyl ester, 35

To compound 34 (0.6 g, 2.72 mmol) was added 2 ml of ethylenediamine and the reaction mixture was stirred under Ar at 55° C. for 16 h. After removal of ethylenediamine by evaporation and co-evaporation with DMF, the residue was suspended in MeOH (1.5 ml) and ether (50 ml) was added. The compound was collected by centrifuge to give a pale yellow powder 35a (0.655 g, 97%).

The above compound 35a (98% pure by HPLC) was dissolved in 20 ml of anhydrous DMF and 1 M solution of di-tert-butyldicarbonate in THF (2.9 ml) was added. The reaction mixture was stirred at room temperature for 2 h. After evaporation of solvent, the residue was crystalized from MeOH—H$_2$O and dried to afford a pale yellow powder 35 (0.785 g, 85%). $^1$H NMR (DMSO-d$_6$) 12.38 (s, 1H), 8.78 (t, 1H), 8.30 (s, 1H), 7.89 (d, 1H), 7.83 (d, 1H), 7.25 (s, 1H), 6.94 (s, 1H), 3.11 (q, 2H), 1.36 (s, 9H).

Example 31

Synthesis of {2-[(6-Amino-1H-indole-2-carbonyl)-amino]-ethyl}-carbamic acid tert-butyl ester, 36

Compound 35 (0.184 g, 0.528 mmol) was dissolved in 15 ml of MeOH and hydrogenated over 5% Pd/C under 40 psi of H$_2$ for 30 min. TLC showed that reaction was completed. After filtration through celite, the filtrate was evaporated and the residue was dried under high vacuum to give compound 36.

Example 32

Synthesis of [2-({2-[2-(2-tert-Butoxycarbonylamino-ethylcarbamoyl)-1H-indol-6-ylcarbamoyl]-1H-indole-5-carbonyl}-amino)-ethyl]-carbamic acid tert-butyl ester, 37

A mixture of above amine 36 and compound 33 (0.226 g, 0.44 mmol) in dry DMF (6 ml) in the presence of DIEA (77 µl, 0.44 mmol) was stirred at 55° C. for 2 days. After removal of solvent, the residue was recrystalized from MeOH-ether to give compound 37 in a quantitative yield.

Example 33

Synthesis of 6-{[5-(2-tert-Butoxycarbonylamino-ethylcarbamoyl)-1H-indole-2-carbonyl]-amino}-1H-indole-2-carboxylic acid methyl ester, 39

A solution of 198 mg (0.9 mmol) 34 in 40 mL methanol was hydrogenated in the presence of 50 mg 10% Pd/C catalyst for 30 minutes at 30 psi. The catalyst was filtered off and the filtrate was evaporated to dryness to give 38 which was dissolved in 3 mL DMF. Meanwhile, 208.4 mg (0.6 mmol) 32 was activated in 2 mL DMF as described for Compound 33 in Example 28 to give 33. 33 and 38 solutions were combined and were heated overnight at 55° C. under Ar atmosphere. Next morning the DMF was evaporated, the oily residue was triturated with ether, the solidified product filtered off, washed with ether and dried to give 310 mg (100%) 39 which was pure enough to be used without further purification.

Example 34

Synthesis of [2-({2-[2-(2-Amino-ethylcarbamoyl)-1H-indol-6-ylcarbamoyl]-1H-indole-5-carbonyl}-amino)-ethyl]-carbamic acid tert-butyl ester, 40

310 mg (0.6 mmol) 39 was dissolved in 10 mL neat ethylenediamine and was heated overnight at 55° C. The ethylenediamine excess was evaporated in vacuo. The oily residue was dissolved in 2 mL methanol and was precipitated by addition of 45 mL ether. The precipitate was spun down, the ether was discarded and the pellet was dried to yield 300 mg (91%) 40.

Example 35

Synthesis of 1H-Indole-2,5-dicarboxylic acid 5-[(2-amino-ethyl)-amide] 2-{[2-(2-amino-ethylcarbamoyl)-1H-indol-6-yl]-amide}, 41

Method A. To compound 37 (0.285 g, 0.44 mmol) was added TFA-anisole (4:1, 5 ml) and the mixture was stirred at room temperature for 2 h. After evaporation of solvent under high vacuum, the residue was washed with ether to give compound 41 as a gray powder in quantitative yield.

Method B. 300 mg (0.55 mmol) 40 was dissolved in a mixture of 1 mL anisol and 4 mL trifluoroacetic acid and was agitated occasionally by swirling for 30 minutes at ambient temperature. 40 mL of cold ether was added, the precipitate was centrifuged, the ether phase was discarded, and the precipitate washed with ether (1×) then it was re-precipitated from 5 mL methanol with 40 mL ether and was dried to give 325 mg (88%) 41 as bis-TFA salt. MS: 224.60 (M/2+H$^+$). $^1$H NMR (DMSO-d$_6$): 11.98 (s, 1H), 11.62 (s, 1H), 10.27 (s, 1H), 8.55 (m, 2H), 8.25 (s, 1H), 8.07 (s, 1H), 7.75 (d, 1H), 7.59 (d, 1H), 7.53 (s, 1H), 7.49 (d, 1H), 7.41 (d, 1H), 7.07 (s, 1H), 3.51 (q, 4H), 2.99 (br, 4H).

Example 36

Synthesis of 1-Methyl-2-thiourea-1,3-dicarboxylic acid di-tert-butyl ester, 42

To a solution of 1-Methyl-2-thiourea (1.5 g, 16.64 mmol) in anhydrous THF (250 ml) was added sodium hydride (1.89 g, 74.88 mmol) in several portions under Ar at 0° C. The reaction mixture was stirred at 0° C. for 5 min and at room temperature for 15 min. The reaction mixture was cooled down to 0° C. and di-tert-butyldicarbonate (8 g, 36.6 mmol) was added. The reaction mixture was stirred at 0° C. for 30 min and at room temperature for a further 4 h. The reaction mixture was then quenched carefully with a saturated $NaHCO_3$ solution at 0° C., and poured into water (150 ml). The organic phase was separated and the water phase was extracted with ethyl acetate (80 ml×3). The combined organic phases were washed with brine, dried over $Na_2SO_4$ and evaporated. The residue was purified by chromatography eluted with EtOAc-toluene (1:22) to give compound 42 as semi-crystals (2.73 g, 57%). $^1$H-NMR (CDCl$_3$) 12.14 (s, 1H), 3.59 (s, 3H), 1.56 (s, 9H), 1.52 (s, 9H).

Example 37

2-Thioxo-imidazolidine-1,3-dicarboxylic acid di-tert-butyl ester, 43

Compound 43 was prepared from 2-imidazolidinethione (1.55 g, 15.2 mmol) with NaH (1.64 g, 68.4 mmol) and di-tert-butyldicarbonate (7.28 g, 33.44 mmol) according to the procedure described for compound 42 in 93% yield. MS: 325.13 (M+Na$^+$), 303.16 (M+H$^+$); mp 117.0–118.5° C.

Example 38

Synthesis of 1,2-Dimethyl-isothiourea, 44

To a cold (0° C.) solution of 1-methyl-2-thiourea (0.902 g, 10 mmol) in DMF (5 mL) was added MeI (1.25 mL, 20 mmol). The reaction instantaneously gave the desired S—Me-isothiorea. The reaction mixture was concentrated, evaporated 1× with DMF and used without further purification. MS: 105.04 (M+H$^+$).

Example 39

Synthesis of N-Methyl-N'-(tert.-butyloxycarbonyl)-methyl-isothiourea, 45

44 (1.04 g, 10.0 mmol) and BOC$_2$O (2.18 g, 10.0 mmol) were dissolved in a biphasic solution of CH$_2$Cl$_2$ (40 mL) and sat. NaHCO$_3$ (40 mL) and the two layers stirred vigorously. After 24 h, the reaction mixture was diluted with CH$_2$Cl$_2$ (60 mL), water (60 mL) and the organic layer separated. The organic layer was washed with water (2×100 mL), dried (Na$_2$SO$_4$) and concentrated. The product oil was purified over silica gel (20% EtOAc/Hexane) to give a mixture of isomers of the product mono-BOC protected S—Me-isothiourea as a sticky oil (1.85 g, 90%). $^1$H-NMR (DMSO-d$_6$) 9.45 (s, 0.4H), 8.97 (s, 1H), 3.17 (s, 3H), 3.06 (s, 1.2H), 2.33 (s, 1.2H), 2.23 (s, 3H), 1.45 (s, 9H), 1.39 (s, 3.6H).

Example 40

Synthesis of N,N'-Dimethyl-N'-(tert.-butyloxycarbonyl)-methyl-isothiourea, 46

Compound 46 was synthesized as a mixture of E and Z isomers as described for Compound 45, except instead of 1-methyl-2-thiourea, 1,3-dimethyl-thiourea was used. Yield: 88% of Compound 46. $^1$H-NMR (DMSO-d$_6$) 3.02 (s, 1.5H), 2.99 (s, 3H), 2.94 (s, 1.5H), 2.87 (s, 3H), 2.28 (s, 1.5H), 2.25 (s, 3H), 1.40 (s, 4.5H), 1.38 (s, 9H).

Example 41

General Guanidylation Methods

Method A: To a solution of amine (0.5 mmol) in anhydrous DMF (10 ml) under Ar was carefully added 2 equiv. of the non-, mono-, or bis-N-alkylated bis-Boc-thiourea and 2 equiv. of HgCl$_2$, followed by 7 equiv. of Et$_3$N at 0° C. The reaction mixture was stirred under Ar at 0° C. for 1.5 h, and at room temperature for 1–2 days. The solution was then diluted with EtOAc (3 ml), filtered through celite, and washed with DMF and CHCl$_3$—MeOH (3:1). The combined filtrations were evaporated to give the crude bis-Boc protected guanidine, respectively. The crude bis-Boc protected guanidine was either purified by chromatography eluted with EtOAc-MeOH (3:1), followed by de-Boc protection with TFA/anisole as described in compound 41 or directly de-Boc protected with TFA/anisole and then purified by reverse phase HPLC.

Method B: To a solution of diamine (0.2 mmol) in pyridine (3 mL) was added the mono-BOC protected S—Me-isothiourea (0.8 mmol). The reaction was run under Ar in a 55° C. oven. When the reaction was complete, pyridine was removed in vacuo and the crude product taken up in MeOH (<5 mL), precipitated with ether (45 mL), spun down, washed 1× with ether, spun down and dried via speed vac. The worked-up product was dissolved in a 4:1 solution of TFA and anisole and reacted at rt for 2 h. The crude deprotected product was precipitated with ether (~45 mL), spun down, washed once with diethyl ether, spun down and dried via speed vac. The crude product was purified on a reverse-phase HPLC column to give its bis-TFA salt. The pure product was then taken up in MeOH (4 mL), treated with 1 mL 4.0 M HCl in dioxane, precipitated with ether, washed 1× with ether, and dried to give its bis-HCl salt.

Example 42

Synthesis of 1H-Indole-2,5-dicarboxylic acid 5-[(2-guanidino-ethyl)-amide] 2-{[2-(2-guanidino-ethyl-carbamoyl)-1H-indol-6-yl]-amide}, 47

To a solution of 41 (100 mg, 0.23 mmol) in dry DMF (5 ml) was added 1H-pyrazole-1-carboxamidine hydrochloride (88 mg, 0.60 mmol) and DIEA (105 µl, 0.60 mmol). The mixture was flushed with Ar and stirred at room temperature for 16 h. The solvent was removed under vacuum and the mixture then purified by reverse phase HPLC to give compound 47 (56 mg, 46%). MS: 266.61 ([M+2H$^+$]/2). $^1$H-NMR (DMSO-d$_6$) 12.06 (s, 1H), 11.62 (s, 1H), 10.35 (s, 1H), 8.67 (t, 1H), 8.63 (t, 1H), 8.28 (s, 1H), 8.09 (s, 1H), 7.77 (d, 1H), 7.66 (m, 2H), 7.59 (d, 1H), 7.57 (s, 1H), 7.49 (d, 1H), 7.45 (d, 1H), 7.12 (s, 1H), 3.42 (br, 4H), 3.36 (br, 4H).

Example 43

Synthesis of 1H-Indole-2,5-dicarboxylic acid 5-{[2-(N'-methyl-guanidino)-ethyl]-amide} 2-({2-[2-(N'methyl-guanidino)-ethylcarbamoyl]-1H-indol-6-yl}-amide), 48

Compound 48 was prepared from compound 41 with 42 according to the general procedure for guanidylation method A. Yield: 36%. MS: 280.64 ([M+2H$^+$]/2). $^1$H-NMR (DMSO-d$_6$) 12.05 (s, 1H), 11.63 (s, 1H), 10.37 (s, 1H), 8.71 (t, 1H), 8.67 (t, 1H), 8.29 (s, 1H), 8.09 (s, 1H), 7.77 (d, 1H), 7.62 (m, 2H), 7.57 (d, 1H), 7.57 (s, 1H), 7.47 (d, 1H), 7.44 (d, 1H), 7.13 (s, 1H), 3.43 (br, 4H), 3.37 (br, 4H), 2.75 (d, 6H).

Example 44

Synthesis of 1H-Indole-2,5-dicarboxylic acid 2-{[2-(N',N"-dimethylguanidino)ethyl]amide} 5-({2-[2-(N',N"-dimethylguanidino)ethylcarbamoyl]-1H-indol-6-yl}amide)dihydrochloride, 49

Compound 49 was synthesized from Compound 41 as described in General Guanidylation Method B using Reagent 46. Yield: 26 mg (22%). MS: 589.34 (M+H$^+$), $^1$H-NMR (DMSO-d$_6$): 12.07 (s, 1H), 11.70 (s, 1H), 10.36 (s, 1H), 8.77 (m, 2H), 8.30 (s, 1H), 8.13 (s, 1H), 7.79 (d, 1H), 7.61 (m, 4H), 7.15 (d, 1H), 3.52–3.25 (m, 8H overlapping with water), 2.79 (m, 12H).

Example 45

Synthesis of 1H-Indole-2,5-dicarboxylic acid 5-{[2-(4,5-dihydro-1H-imidazol-2-ylamino)-ethyl]amide} 2-({2-[2-(4,5-dihydro-1H-imidazol-2-ylamino)-ethylcarbamoyl]-1H-indol-6-yl}-amide), 50

Compound 50 was prepared from compound 41 with 43 according to the general procedure for guanidylation method A. Yield: 45%. MS: 292.65 ([M+2H$^+$]/2). $^1$H-NMR (DMSO-d$_6$) 12.05 (s, 1H), 11.64 (s, 1H), 10.36 (s, 1H), 8.72 (t, 1H), 8.64 (t, 1H), 8.40–8.29 (m, 4H), 8.08 (s, 1H), 7.78–7.75 (m, 2H), 7.59–7.56 (m, 2H), 7.49–7.43 (2H), 7.15 (s, 1H), 3.57 (br s, 8H), 3.44 (t, 4H), 3.39 (t, 4H).

Example 46

Synthesis of 1H-Indole-2,5-dicarboxylic acid 5-{[2-(2,6-diamino-hexanoylamino)-ethyl]-amide} 2-({2-[3-(2,6-diamino-hexanoylamino)-propylcarbamoyl]-1H-indol-6-yl}-amide), 51

The precursor diamine was synthesized as described for Compound 41 in Example 26 through Example 35, except instead of 1,2-ethylenediamine, 1,3-diaminopropane was used. To a solution of 0.2 mmol of this diamine in 2 mL DMF 532 mg (1.2 mmol) Boc-Lys(Boc)-OSu was added followed by 310 µL (1.8 mmol) DIEA. The mixture was stirred overnight at ambient temperature. Next day the solvent was evaporated, the remaining oil was taken up in 3 mL methanol and was precipitated with 40 mL ether. The pellet was centrifuged, washed twice with ether and dried. The protected compound was dissolved in 5 mL TFA-anisol 4:1 mixture and was stirred for 30 minutes at room. The crude product was precipitated with 40 mL cold ether, the precipitate was spun down, washed twice with ether and dried. The solid material was dissolved in 5 mL aqueous 0.1% TFA solution and was purified on a preparative reverse phase HPLC column using acetonitrile gradient. The fractions containing the pure product were pooled, evaporated to dryness dissolved in 3 mL methanol and treated with 1 mL 4.0M HCl in dioxane. 51 was precipitated with ether as bis-HCl salt, filtered off and dried to yield 52 mg (30%). MS: 359.73 (M+H$^+$); $^1$H-NMR (DMSO d$_6$) 12.02 (s, 1H); 11.60 (s, 1H); 10.40 (s, 1H); 8.86–8.76 (m, 2H); 8.61–7.60 (d, 2H); 8.2 (s, br); 8.10–8.03 (m); 7.79–7.76 (m); 7.61–7.44 (m); 7.12 (s, 1H); 3.74 (m); 3.36–3.12 (m); 2.74 (m); 1.74–1.72 (m); 1.59–1.51 (m); 1.42–1.32 (m).

Example 47

Synthesis of 1H-Indole-2,5-dicarboxylic acid 2-{[2-(2-guanidinoethylcarbamoyl)-1H-indol-6-yl]amide} 5-[(3-guanidinopropyl)amide]dihydrochloride, 52

Compound 52 was synthesized as described for Compound 47 in Example 26 to Example 42, except instead of BOC-ethylenediamine, BOC-1,3-diaminopropane was used. Yield: 52%. MS: 547.34 (M+H$^+$), $^1$H-NMR (DMSO-d$_6$): 12.07 (s, 1H), 11.69 (s, 1H), 10.40 (s, 1H), 8.76 (t, 1H), 8.55 (t, 1H), 8.30 (s, 1H), 8.13 (s, 1H), 7.80 (d, 1H), 7.62 (d, 1H), 7.50 (m, 3H), 7.18 (s, 1H), 3.47 (m, 4H, overlapping with water), 3.23 (m, 4H), 1.80 (m, 2H).

Example 48

Synthesis of 1H-Indole-2,5-dicarboxylic acid 2-({2-[2-(N'-methylguanidino)ethylcarbamoyl]-1H-indole-6-yl}amide) 5-{[3-(N'-methylguanidino)propyl]amide}dihydrochloride, 53

Compound 53 was synthesized as described for Compound 48 in Example 26 to Example 43, except instead of BOC-ethylenediamine, BOC-1,3-diaminopropane was used. Yield: 24%. MS: 575.34 (M+H$^+$), $^1$H-NMR (DMSO-d$_6$): 12.03 (s, 1H), 11.68 (s, 1H), 10.35 (s, 1H), 8.69 (t, 1H), 8.52 (t, 1H), 8.28 (s, 1H), 8.12 (s, 1H), 7.80 (d, 1H), 7.50 (m, 4H), 7.15 (s, 1H), 3.46 (m, 4H, overlapping with water), 3.38 (m, 4H, overlapping with water), 2.78 (d, 6H), 1.80 (m, 2H).

Example 49

Synthesis of 1H-Indole-2,5-dicarboxylic acid 2-({2-[2-(N',N"-dimethylguanidino)ethylcarbamoyl]-1H-indole-6-yl}amide) 5-{[3-(N',N"-dimethylguanidino)propyl]amide}dihydrochloride, 54

Compound 54 was synthesized as described for Compound 49 in Example 26 to Example 44, except instead of BOC-ethylenediamine, BOC-1,3-diaminopropane was used. Yield: 35%. MS: 603.36 (M+H$^+$), $^1$H-NMR (DMSO-d$_6$): 12.04 (s, 1H), 11.70 (s, 1H), 10.36 (s, 1H) 8.72 (t, 1H), 8.54 (t, 1H), 8.29 (s, 1H), 8.12 (s, 1H), 7.78 (d, 1H), 7.55 (m, 4H), 7.15 (s, H), 3.52–3.25 (m, 8H, overlapping with water), 2.80 (m, 12H), 1.82 (m, 2H).

Example 50

Synthesis of 1H-Indole-2,5-dicarboxylic acid 5-{[2-(2-(N'-methylguanidino)ethyl]amide} 2-({2-[2-(N'-methylguanidino)ethylcarbamoyl]-1H-indole-5-yl}amide)dihydrochloride, 55

Compound 55 was synthesized from Compound 88 as described in Example 41, General Guanidylation Method A using N,N'-diBOC-N-methylthiourea as the reagent. Yield: 17%. MS: 561.24 (M+H$^+$), $^1$H-NMR (DMSO-d$_6$): 12.03 (s, 1H), 11.67 (s, 1H), 10.28 (s, 1H), 8.74 (t, 1H), 8.66 (t, 1H), 8.30 (s, 1H), 8.15 (s, 1H), 7.79 (dd, 1H), 7.53 (m, 4H), 7.17 (s, 1H), 3.47 (m, 8H, overlapping with water), 2.78 (d, 6H).

Example 51

Synthesis of 1H-Indole-2,5-dicarboxylic acid 2-{[2-(N',N"-dimethylguanidino)ethyl]amide} 5-({2-[2-(N',N"-dimetlhylguanidino)ethylcarbamoyl]-1H-indol-5-yl}amide), 56

Compound 56 was synthesized as described for Compound 49 in Example 26 to Example 44 except instead of Compound 4, Compound 88 was used. Yield: 49%. MS: 589.32 (M+H$^+$), $^1$H-NMR (DMSO-d$_6$): 12.07 (s, 1H), 11.69 (s, 1H), 10.32 (s, 1H), 8.90 (t, 1H), 8.78 (t, 1H), 8.32 (s, 1H), 8.16 (d, 1H), 7.80 (dd, 1H), 7.58 (m, 4H), 7.21 (d, 1H), 3.50(m, 8H, overlapping with water), 2.80 (d, 12H).

Example 52

Synthesis of 1H-In dole-2,5-dicarboxylic acid 5-{[2-(4,5-dihydro-1H-imidazol-2-ylamino)ethyl]amide} 2-({2-[2-(4,5-dihydro-1H-imidazol-2-ylamino)ethylcarbamoyl]-1H-indole-5-yl}amide)dihydrochloride, 57

Compound 57 was synthesized as described for Compound 50 in Example 26 to Example 45, except instead of Compound 41, Compound 88 was used. Yield: 21%. MS: 585.30 (M+H$^+$), $^1$H-NMR (DMSO-d$_6$): 12.00 (s, 1H), 11.65 (s, 1H), 10.26 (s, 1H), 8.64 (t, 1H), 8.58 (t, 1H), 8.41 (q, 2H), 8.27 (s, 1H), 8.13 (d, 1H), 7.78 (dd, 1H), 7.56–7.44 (m, 4H), 7.15 (d, 1H), 3.63 (m, 8H), 3.41 (m, 8H).

Example 53

Synthesis of 1H-Indole-2,5-dicarboxylic acid 2-{[2-(2-guanidinoethylcarbamoyl)-1H-indol-5-yl]amide} 5-[(3-guanidinopropyl)amide]dihydrochloride, 58

Compound 58 was synthesized as described for Compound 47 in Example 26 to Example 42, except instead of BOC-ethylenediamine, BOC-1,3-diaminopropane and instead of Compound 41, Compound 88 were used. Yield: 46%. MS: 547.30 (M+H$^+$), $^1$H-NMR (DMSO-d$_6$): 12.00 (s, 1H), 11.67 (s, 1H), 10.28 (s, 1H), 8.76 (t, 1H), 8.55 (t, 1H), 8.28 (s, 1H), 8.14 (s, 1H), 7.76 (d, 1H), 7.63 (m, 2H), 7.50 (m, 3H), 7.17 (s, 1H), 3.47 (m, 4H), 3.24 (m, 4H), 1.79 (m, 2H).

Example 54

Synthesis of 1H-Indole-2,5-dicarboxylic acid 2-({2-[2-(N'methylguanidino)ethylcarbamoyl]-1H-indol-5-yl}amide) 5-{[3-(N'methylguanidino)propyl]amide}hydrochloride, 59

Compound 59 was synthesized as described for Compound 48 in Example 26 to Example 43, except instead of BOC-ethylenediamine, BOC-1,3-diaminopropane and instead of Compound 4, Compound 88 were used. Yield: 16%. MS: 575.34 (M+H$^+$), $^1$H-NMR (DMSO-d$_6$): 12.02 (s, 1H), 11.67 (s, 1H), 10.28 (s, 1H), 8.75 (t, 1H), 8.54 (t, 1H), 8.28 (s, 1H), 8.15 (s, 1H), 7.77 (d, 1H), 7.50 (m, 4H), 7.18 (s, 1H), 3.52 (m, 8H, overlapping with water), 2.80 (d, 6H), 1.79 (m, 2H).

Example 55

Synthesis of 1H-Indole-2,5-dicarboxylic acid 2-({2-[2-(N',N"-dimethylguanidino)ethylcarbamoyl]-1H-indol-5-yl}amide) 5-{[3-(N',N"-dimethylguanidino)propyl]amide}hydrochloride, 60

Compound 60 was synthesized as described for Compound 49 in Example 26 to Example 44, except instead of BOC-ethylenediamine, BOC-1,3-diaminopropane and instead of Compound 4, Compound 88 was used. Yield: 20%. MS: 603.36 (M+H$^+$), $^1$H-NMR (DMSO-d$_6$): 12.05 (s, 1H), 11.70 (s, 1H), 10.33 (s, 1H), 8.91 (t, 1H), 8.64 (t, 1H), 8.32 (s, 1H), 8.16 (d, 1H), 7.80 (dd, 1H), 7.57 (m, 4H), 7.21 (d, 1H), 3.50 (m, 4H, overlapping with water), 3.29 (m, 4H), 2.80 (d, 12H), 1.82 (m, 2H).

Example 56

Synthesis of 1H-Indole-2,5-dicarboxylic acid 2-{[2-(2-carbamimidoylethylcarbamoyl)-1H-indol-5-yl]amide} 5-[(2-guanidinoethyl)amide]dihydrochloride, 61

Compound 61 was synthesized as described for Compound 47 in Example 26 to Example 42, except instead of Compound 38, Compound 1 was used and the procedure described in Example 34 was skipped. Yield: 37%. MS: 518.26 (M+H$^+$), $^1$H-NMR (DMSO-d$_6$): 12.06 (s, 1H), 11.68 (s, 1H), 10.35 (s, 1H), 9.13 (s, 2H), 8.83 (t, 1H), 8.71 (s, 2H), 8.33 (s, 1H), 8.15 (s, 1H), 7.80 (m, 2H), 7.54 (m, 3H), 7.23 (s, 1H), 3.70 (m, 4H), 2.75 (m, 4H).

Example 57

Synthesis of 1H-Indole-2,5-dicarboxylic acid 5-[(2-guanidino-ethyl)-amide] 2-{[2-(3-guanidino-propyl-carbamoyl)-1H-indol-6-yl]-amide}, 62

Compound 62 was synthesized as described for Compound 47 in Example 27 through Example 42, except in Example 34 instead of 1,2-ethylenediamine, 1,3-diaminopropane was used. Yield: 46% of compound 62. MS: 273.66 ([M+2H$^+$]/2). $^1$H-NMR (DMSO d$_6$) 12.03 (s, 1H); 11.60 (s, 1H); 10.34 (s, 1H); 8.64–8.62 (t, 1H); 8.58–8.57 (t, 1H); 8.29 (s, 1H); 8.07 (s, 1H); 7.77–7.74 (m, 2H); 7.56–7.41 (m, 3H); 7.10 (d, 1H);3.42–3.34 (m, 6H); 3.23–3.1 (m, 2H); 1.77–1.72 (m, 2H).

Example 58

Synthesis of 1H-Indole-2,5-dicarboxylic acid 5-{[2-(N'-methyl-guanidino)-ethyl]-amide} 2-({2-[3-(N'-methyl-guanidino)-propylcarbamoyl]-1H-indol-6-yl}-amide), 63

Compound 63 was synthesized as described for Compound 48 in Example 27 through Example 43, except instead of 1,2-ethylenediamine, 1,3-diaminopropane was used. Yield: 30% of compound 63. MS: 287.68 ([M+2H$^+$]/2). $^1$H-NMR (DMSO d$_6$) 12.02 (s, 1H); 11.60 (s, 1H); 10.34 (s, 1H); 8.66–8.59 (m, 2H); 8.28 (s, 1H); 8.06 (d, 1H); 7.77–7.40 (m, 13H); 7.12 (d, 1H); 3.43–3.18 (m, 8H, overlapping with water); 2.74–2.72 (d, 6H); 1.77–1.73 (m, 2H).

Example 59

Synthesis of 1H-Indole-2,5-dicarboxylic acid 2-{[2-(N',N''-dimethyl-guanidino)-ethyl]-amide} 5-({2-[3-(N', N''-dimethyl-guanidino)-propylcarbamoyl]-1H-indol-6-yl}-amide)), 64

Compound 64 was synthesized as described for Compound 49 in Example 27 through Example 44, except instead of 1,2-ethylenediamine, 1,3-diaminopropane was used. Yield: 33% of compound 64. MS: 301.69 ([M+2H$^+$]/2). $^1$H-NMR (DMSO d$_6$) 12.02 (s, 1H); 11.60 (s, 1H); 10.33 (s, 1H); 8.75–8.67 (m, 2H); 8.28 (s, 1H); 8.06 (d, 1H); 7.77–7.74 (dd, 1H); 7.62–7.41 (m, 13H), 7.14 (d, 1H); 3.46–3.24 (m, 8H, overlapping with water); 2.76–2.73 (m, 12H); 1.79–1.74 (m, 2H).

Example 60

Synthesis of 1H-Indole-2,5-dicarboxylic acid 5-{[2-(2,5-diamino-pentanoylamino)-ethyl]-amide} 2-({2-[3-(2,5-diamino-pentanoylamino)-propylcarbamoyl]-1H-indol-6-yl}-amide), 65

Compound 65 was synthesized as described for Compound 51 in Example 46, except instead of Boc-Lys(Boc)-OSu, Fmoc-Orn(Boc)-OPfp was used and after the TFA treatment the Fmoc protecting group was removed by a 20 minutes treatment with 5 mL 20% piperidine in DMF. The piperidine/DMF was evaporated; the oil was taken up in 3 mL methanol and was precipitated with 40 mL ether. The pallet was spun down, washed twice with ether and dried. The solid crude product was HPLC purified using the same conditions. Yield: 66.5 mg (39%) of compound 65. MS: 345.71 ([M+2H$^+$]/2). $^1$H-NMR (DMSO d$_6$) 12.04 (s, 1H); 11.63 (s, 1H); 10.40 (s, 1H); 8.94–8.90 (m, 2H); 8.70–8.66 (m, 2H); 8.44–8.3 (m, 7H); 8.14–8.02 (m, 7H); 7.81–7.78 (dd, 1H); 7.60–7.44 (m, 4H); 7.14 (d, 1H); 3.81 (m, 2H); 3.39–3.16 (m); 2.80 (m, 4H); 1.86–1.60 (m, 10H).

Example 61

Synthesis of 1H-Indole-2,5-dicarboxylic acid 5-{[2-(2-amino-5-guanidino-pentanoylamino)-ethyl]-amide} 2-({2-[3-(2-amino-5-guanidino-pentanoylamino)-propylcarbamoyl]-1H-indol-6-yl}-amide), 66

Compound 66 was synthesized as described for Compound 51 in Example 46, except instead of Boc-Lys(Boc)-OSu, Boc-Arg(Mts)-OPfp was used and after the TFA treatment the Mts protecting group was removed by a 2 hr treatment with a cocktail composed of 5 mL TFA 500 µL TFMSA, 500 µL thioanisole and 250 µL EDT. The crude product was precipitated with 40 mL cold ether. The precipitate was spun down, washed twice with ether and dried. The solid crude material was HPLC purified using the same conditions. Yield: 56.9 mg (31%) of compound 66. MS: 387.73 ([M+2H$^+$]/2). $^1$H-NMR (DMSO d$_6$) 12.02 (s, 1H); 11.61 (s, 1H); 10.37 (s, 1H); 8.89–8.83 (m, 2H); 8.65–8.63 (m, 2H); 8.40–8.26 (m, 6H); 8.09 (s, 1H); 7.98 (m, 1H); 7.90–7.82 (m, 1H); 7.82–7.78 (dd, 1H); 7.57–7.43 (m, 4H); 7.13–7.11 (m, 2H); 3.79 (m, 2H); 3.4–3.26 (m); 3.20–3.10 (m, 4H); 1.75 (m, 6H); 1.51 (m, 4H).

Example 62

Synthesis of 1H-Indole-2,5-dicarboxylic acid 5-[(2-guanidino-ethyl)-amide] 2-{[2-(3-guanidino-propylcarbamoyl)-1H-indol-5-yl]-amide}, 67

Compound 67 was synthesized as described for Compound 47 in Example 27 through Example 42, except instead of 34 and 1,2-ethylenediamine, 5-nitroindole-2-carboxylic acid ethyl ester and 1,3-diaminopropane were used, respectively. Yield: 52% of compound 67. MS: 273.67 ([M+2H$^+$]/2). $^1$H-NMR (DMSO d$_6$) 12.02 (s, 1H), 11.61 (s, 1H); 10.28 (s, 1H); 8.66–8.60 (m, 2H); 8.28 (s, 1H); 8.09 (d, 1H), 7.77–7.70 (m, 3H); 7.53–7.37 (m, 5H); 7.14 (d, 1H); 3.40–3.33 (m, 6H, overlapping with water); 3.23–3.17 (m, 2H); 1.78–1.73 (m, 2H).

Example 63

Synthesis of 1H-Indole-2,5-dicarboxylic acid 5-{[2-(N'-methyl-guanidino)-ethyl]-amide} 2-({2-[3-(N'-methyl-guanidino)-propylcarbamoyl]-1H-indol-5-yl}-amide), 68

Compound 68 was synthesized as described for Compound 48 in Example 27 through Example 43, except instead of 34 and 1,2-ethylenediamine, 5-nitroindole-2-carboxylic acid ethyl ester and 1,3-diaminopropane were used, respectively. Yield: 34% of compound 68. MS: 287.66 ([M+2H$^+$]/2). $^1$H-NMR (DMSO d$_6$) 12.02 (s, 1H); 11.60 (s, 1H) 10.27 (s, 1H); 8.70–8.2 (m, 2H); 8.27 (s, 1H); 8.09 (s, 1H); 7.78–7,74 (dd, 1H); 7.65–7.37 (m, 4H); 7.15 (d, 1H); 3.48–3.26 (m, 6H overlapping with water); 3.24–3.18 (m, 2H); 2.74–2.73 (d, 6H); 1.78–1.73 (m, 2H).

Example 64

Synthesis of 1H-Indole-2,5-dicarboxylic acid 2-{[2-(N',N''-dimethyl-guanidino)-ethyl]-amide} 5-({2-[3-(7N',N''-dimethyl-guanidino)-propylcarbamoyl]-1H-indol-5-yl}-amide), 69

Compound 69 was synthesized as described for Compound 49 in Example 27 through Example 44, except instead of 34 and 1,2-ethylenediamine, 5-nitroindole-2-carboxylic acid ethyl ester and 1,3-diaminopropane were used, respectively. Yield: 37% of compound 69. MS: 301.68 ([M+2H$^+$ 1/2). $^1$H-NMR (DMSO d$_6$) 12.02 (s, 1H); 11.61 (s, 1H) 10.27 (s, 1H); 8.78–8.70 (m, 2H); 8.28 (s, 1H); 8.10 (s, 1H); 7.77–7.73 (dd, 1H); 7.62–7.34 (m, 4H); 7.18 (d, 1H); 3.50–3.42 (m, 2H); 3.37–3.21 (m, 6H, overlapping with water); 2.76–2.74 (m, 12H); 1.82–1.75 (m, 2H).

Example 65

Synthesis of N-(2-Guanidino-ethyl)-N'-[2-(2-guanidino-ethylcarbamoyl)-1H-indol-5-yl]-terephthalamide, 70

Compound 70 was synthesized as described for Compound 47 in Example 27 through Example 42, except instead of 32 and 34, 94 and 5-nitroindole-2-carboxylic acid ethyl ester were used, respectively. Yield: 60% of compound 70. MS: 247.11 ([M+2H$^+$]/2). $^1$H-NMR (DMSO d$_6$) 11.65 (s, 1H); 10.30 (s, 1H); 8.85 (t, 1H); 8.70 (t, 1H); 8.15–7.95 (m, 4H); 7.70 (m, 2H); 7.55–7.35 (m, 2H); 7.15 (s, 1H); 3.50–3.25 (m, 8H, overlapping with water).

Example 66

Synthesis of N-(2-Guanidino-ethyl)-N'-[2-(2-guanidino-ethylcarbamoyl)-1H-indol-7-yl]-terephthalamide, 71

Compound 71 was synthesized as described for Compound 47 in Example 27 through Example 42, except instead of 3 and 4, 94 and 7-nitroindole-2-carboxylic acid ethyl ester were used, respectively. Yield: 36.5 mg (46%) of compound 71. MS: 247.10 ([M+2H$^+$]/2). $^1$H-NMR (DMSO d$_6$) 11.69 (S, 1 h); 10.28 (S, 1H); 8.92 (t, 1H); 8.84 (t, 1H); 8.10–8.03 (m, 4H); 7.86–7.83 (dd, 1H), 7.82–7.74 (m, 2H); 7.46–7.43 (d, 1H); 7.25–7.24 (d, 1H); 7.08–7.03 (t, 1H); 3.48–3.33 (m, 8H, overlapping with water).

Example 67

Synthesis of 1H-Indole-2,5-dicarboxylic acid 5-[(3-guanidino-propyl)-amide] 2-{[2-(3-guanidino-propylcarbamoyl)-1H-indol-6-yl-]-amide}, 72

Compound 72 was synthesized as described for Compound 47 in Example 26 through Example 42, except that in Example 26, instead of (2-amino-ethyl)-carbamic acid tert-butyl ester, (3-amino-propyl)-carbamic acid tert-butyl ester was used and in Example 34, instead of 1,2-ethylenediamine, 1,3-propylenediamine was used. Yield: 34% of compound 72. MS: 280.68 ([M+2H$^+$]/2). $^1$H-NMR (DMSO d$_6$) 12.03 (s, 1H), 11.62 (s, 1H), 10.35 (s, 1H), 8.60 (t, 1H), 8.51 (t, 1H), 8.26 (s, 1H), 8.07 (s, 1H), 7.85–7.70 (m, 3H), 7.60–6.60 (m, 13H), 3.30–3.00 (m, 8H), 1.85–1.65 (m, 4H).

Example 68

Synthesis of 1H-Indole-2,5-dicarboxylic acid 5-[(3-(N'-methyl-guanidino)-propyl)-amide] 2-{[2-(3-(N'-methyl-guanidino)-propylcarbamoyl)-1H-indol-6-yl-]-amide}, 73

Compound 73 was synthesized as described for Compound 48 in Example 26 through Example 43 using guanylation Method B, except in Example 26 instead of (2-amino-ethyl)-carbamic acid tert-butyl ester, (3-amino-propyl)-carbamic acid tert-butyl ester was used and in Example 34 instead of 1,2-ethylenediamine, 1,3-propylenediamine was used. Yield: 26% of compound 73. MS: 294.69 ([M+2H$^+$]/2). $^1$H-NMR (DMSO d$_6$) 12.04 (s, 1H), 11.63 (s, 1H), 10.38 (s, 1H), 8.66 (t, 1H), 8.56 (t, 1H), 8.28 (s, 1H), 8.08 (s, 1H), 7.80–7.30 (m, 13H), 7.14 (s, 1H), 3.38–3.28 (m, 4H), 3.26–3.14 (m, 4H), 2.75 (s, 3H), 2.74 (s, 3H), 1.86–1.68 (m, 4H).

Example 69

Synthesis of 1H-Indole-2,5-dicarboxylic acid 5-[(3-(N N',N''-dimethyl-guanidino)-propyl)-amide] 2-{[2-(3-(N',N''-dimethyl-guanidino)-propylcarbamoyl)-1H-indol-6-yl-]-amide}, 74

Compound 73 was synthesized as described for Compound 49 in Example 26 through Example 44 using guanylation Method B, except that in Example 26 instead of (2-amino-ethyl)-carbamic acid tert-butyl ester, (3-amino-propyl)-carbamic acid tert-butyl ester was used, and in Example 34, instead of 1,2-ethylenediamine, 1,3-propylenediamine was used. Yield: 27% of compound 74. MS: 308.70 ([M+2H$^+$]/2). $^1$H-NMR (DMSO d$_6$) 12.02 (s, 1H), 11.63 (s, 1H), 10.35 (s, 1H), 8.71 (t, 1H), 8.61 (t, 1H), 8.29 (s, 1H), 8.08 (s, 1H), 7.70 (dd, 1H), 7.60–7.40 (m, 10H), 7.15 (s, 1H), 3.36–3.20 (m, 8H), 2.77 (s, 6H), 2.75 (s, 6H), 1.86–1.70 (m, 4H).

Example 70

Synthesis of 1H-Indole-2,5-dicarboxylic acid 5-[(3-guanidino-propyl)-amide] 2-{[2-(3-guanidino-propylcarbamoyl)-1H-indol-5-yl-]-amide}, 75

Compound 75 was synthesized as described for Compound 47 in Example 26 through Example 42, except in Example 26 instead of (2-amino-ethyl)-carbamic acid tert-butyl ester, (3-amino-propyl)-carbamic acid tert-butyl ester was used and in Example 33 instead of Compound 34 Compound 1 was used and in Example 34 instead of 1,2-ethylenediamine, 1,3-propylenediamine was used. Yield: 49% of compound 75. MS: 280.66 ([M+2H$^+$]/2). $^1$H-NMR (DMSO d$_6$) 12.01 (s, 1H), 11.61 (s, 1H), 10.29 (s, 1H), 8.64 (t, 1H), 8.51 (t, 1H), 8.25 (s, 1H), 8.10 (s, 1H), 7.90–7.90 (m, 3H), 7.60–6.60 (m, 13H), 3.40–3.30 (m, 4H), 3.25–3.10 (m, 4H), 1.90–1.70 (m, 4H).

Example 71

Synthesis of 1H-Indole-2,5-dicarboxylic acid S-[(3-(N'-methyl-guanidino)-propyl)-amide] 2-[[2-(3-(N'-methyl-guanidino)-propylcarbamoyl)-1H-indol-5-yl-]-amide), 76

Compound 76 was synthesized as described for Compound 48 in Example 26 through Example 43 using guanylation Method B, except that in Example 26 instead of (2-amino-ethyl)-carbamic acid tert-butyl ester, (3-amino-propyl)-carbamic acid tert-butyl ester was used; in Example 33 instead of Compound 34 Compound 1 was used; and in Example 34 instead of 1,2-ethylenediamine, 1,3-propylenediamine was used. Yield: 31% of compound 76. MS: 294.67 ([M+2H$^+$]/2). $^1$H-NMR (DMSO d$_6$) 12.02 (s, 1H), 11.62 (s, 1H), 10.30 (s, 1H), 8.70 (t, 1H), 8.55 (t, 1H), 8.27 (s, 1H), 8.10 (s, 1H), 7.80–7.30 (m, 13H), 7.17 (s, 1H), 3.40–3.30 (m, 4H), 3.28–3.16 (m, 4H), 2.75 (s, 3H), 2.74 (s, 3H), 1.86–1.70 (m, 4H).

Example 72

Synthesis of 1H-Indole-2,5-dicarboxylic acid 5-[(3-(N',N''-dimethyl-guanidino)-propyl)-amide] 2-{[2-(3-(N',N''-dimethyl-guanidino)-propylcarbamoyl)-1H-indol-5-yl-]-amide}, 77

Compound 77 was synthesized as described for Compound 49 in Example 26 through Example 44 using guanylation Method B, except that in Example 26 instead of (2-amino-ethyl)-carbamic acid tert-butyl ester, (3-amino-propyl)-carbamic acid tert-butyl ester was used and in Example 33 instead of 34, 101 was used and in Example 34 instead of 1,2-ethylenediamine, 1,3-propylenediamine was used. Yield: 52% of compound 77. MS: 308.69 ([M+2H$^+$]/2). $^1$H-NMR (DMSO d$_6$) 12.04 (s, 1H), 11.63 (s, 1H), 10.32 (s, 1H), 8.83 (t, 1H), 8.65 (t, 1H), 8.30 (s, 1H), 8.11 (s, 1H), 7.77 (dd, 1H), 7.70–7.30 (m, 10H), 7.21 (s, 1H), 3.40–3.20 (m, 8H), 2.77 (s, 6H), 2.76 (s, 6H), 1.84–1.70 (m, 4H).

Example 73

Synthesis of 1H-Indole-2,5-dicarboxylic acid 5-[(2-guanidino-ethyl)-amide] 2-{[2-(2-guanidino-ethylcarbamoyl)-1H-indol-7-yl-]-amide}, 78

Compound 78 was synthesized as described for Compound 47 in Example 26 through Example 42, except in Example 33 instead of 3,7-nitro-1H-indole-2-carboxylic acid ethyl ester was used. Yield: 40% of compound 78. MS: 266.62 ([M+2H$^+$]/2). $^1$H-NMR (DMSO d$_6$) 12.11 (s, 1H), 11.79 (s, 1H), 10.26 (s, 1H), 8.91 (t, 1H), 8.72 (t, 1H), 8.36 (s, 1H), 8.00–6.70 (m, 17H), 3.50–3.30 (m, 8H).

Example 74

Synthesis of 1H-Indole-2,5-dicarboxylic acid 5-[(2-amino-ethyl)-amide] 2-{[5-(2-amino-ethylcarbamoyl)-1-isobutyl-1H-pyrrol-3-yl]-amide}, 79

Compound 26 was reduced to its amine by hydrogenation according to the procedure for 36. The amine was then coupled with compound 3, followed by deprotection with TFA/anisole according to the similar procedure for the preparation of compound 41 to give compound 79 in 78% yield.

Example 75

Synthesis of 1H-Indole-2,5-dicarboxylic acid 5-[(2-guanidino-ethyl)-amide] 2-{[5-(2-guanidino-ethylcarbamoyl)-1-isobutyl-1H-pyrrol-3-yl]-amide), 80

Compound 80 was prepared from 79 with 1H-pyrazole-1-carboxamidine hydrochloride according to the procedure for compound 47. Yield: 61%. MS 269.65 ([M+2H$^+$]/2). $^1$H-NMR (DMSO-d$_6$) 11.92 (s, 1H), 10.52 (s, 1H), 8.61 (t, 1H), 8.26 (s, 1H), 8.21 (t, 1H), 7.74 (dd, 1H), 7.69 (t, 1H), 7.62 (t, 1H), 7.47 (d, 1H), 7.42 (s, 1H), 7.29 (d, 1H), 6.97 (d, 1H), 4.12 (d, 2H), 3.48–3.26 (m, 8H), 1.98 (dt, 1H), 0.81 (d, 6H).

Example 76

1H-Indole-2,5-dicarboxylic acid 2-({1-isobutyl-5-[2-(N'-methyl-guanidino)-ethylcarbamoyl]-1H-pyrrol-3-yl}amide) 5-{[2-(N'-methyl-guanidino)-ethyl]-amide}, 81

Compound 81 was prepared from 79 with 42 according to the general procedure for guanidylation method A. Yield: 31%. MS 283.67 (([M+2H$^+$]/2). $^1$H-NMR (DMSO-d$_6$) 11.93 (s, 1H), 10.53 (s, 1H), 8.64 (t, 1H), 8.26 (br s, 2H), 7.75 (dd, 1H), 7.66–7.53 (m, 2H), 7.48–7.42 (m, 2H), 7.30 (d, 1H), 6.97 (d, 1H), 4.12 (d, 2H), 3.47–3.25 (m, 8H), 2.74 (d, 6H), 1.96 (dt, 1H), 0.81 (d, 6H).

Example 77

1H-Indole-2,5-dicarboxylic acid 5-[(2-guanidino-ethyl)-amide] 2-{[2-(2-guanidino-ethylcarbamoyl)-1H-indol-5-yl]-amide}, 82

Compound 82 was synthesized as described for Compound 62 in Example 57, except in Example 34 instead of 1,3-diaminopropane, 1,2-ethylenediamine was used. Yield: 46% of compound 82. MS: 266.69 ([M+2H$^+$]/2). $^1$H-NMR (DMSO-d$_6$) 11.98 (s, 1H), 11.62 (s, 1H), 10.25 (s, 1H), 8.65 (t, 1H), 8.59 (t, 1H), 8.26 (s, 1H), 8.10 (s, 1H), 7.75 (d, 1H), 7.6–7.38 (m, 5H), 7.10 (d, 2H), 3.4 (m, 4H).

Example 78

5-{5-(2-Amino-ethylcarbamoyl)-1H-indole-2-carbonyl]-amino}-1H-indole-2-carboxylic acid ethyl ester, 83

To a solution of 33 (100 mg, 0.2 mmol) in DMF (3 mL) was added freshly reduced 102 (66 mg, 0.3 mmol). The solution was kept at 55 C for 18 hours and then the solvents were removed in vacuo. The crude material was then suspended in anisole (400 μL) and trifluoroacetic acid (1.8 mL) added. After 30 minutes at ambient temperature the product was precipitated by the addition of ether (45 mL). The precipitate was purified by reverse-phase HPLC and converted to hydrochloride salt by the addition of 2 ml 4 M HCl in dioxane to 4 ml of methanolic solution of the trifluoroacetate and precipitating twice with cold Et$_2$O. The precipitate was lyophilized to yield 60 mg (64%) of Compound 83.
MS: 434.13 (M+H$^+$). $^1$H-NMR (DMSO-d$_6$) 12.0 (s, 1H), 11.87 (s, 1H), 10.25 (s, 1H), 8.57 (t, 1H), 8.26 (s, 1H), 8.11 (s, 1H), 7.84–7.73 (m, 4H), 7.59–7.41 (m, 4H), 7.14 (s, 1H), 4.31 (q, 2H), 3.50 (m, 2H), 2.98 (m, 2H), 1.32 (t, 3H).

Example 79

5-{[5-(2-Amino-ethylcarbamoyl)-1H-indole-2-carbonyl]-amino}-1H-indole-2-carboxylic acid, 84

Compound 83 (35 mg, 0.074 mmol) was dissolved in MeOH (1.5 mL) and then 1 M NaOH (0.75 mL, 0.75 mmol) was added. The reaction was stirred at 55 C for 16 hours and then the reaction was neutralized by addition of 1 M HCl (0.75 mL, 0.75 mmol) and the mixture concentrated in vacuo. The residue was purified by reverse-phase HPLC and converted to the hydrochloride salt by the addition of 2 ml 4 M HCl in dioxane to 4 ml of methanolic solution of the trifluoroacetate and precipitating twice with cold Et$_2$O. The precipitate was lyophilized to yield 12.6 mg (39%) of Compound 84.

MS: 406.23 (M+H$^+$). $^1$H-NMR (DMSO-d$_6$) 12.95 (br s, 1H), 12.02 (s, 1H), 11.75 (s, 1H), 10.29 (s, 1H), 8.64 (t, 1H), 8.31 (s, 1H), 8.13 (s, 1H), 7.97 (br s, 2H), 7.77 (d, 1H), 7.60–7.40 (m, 4H), 7.08 (s, 1H), 3.52 (m, 2H), 2.48 (m, 2H).

Example 80

1H-Indole-2,5-dicarboxylic acid 5-[(2-amino-ethyl)-amide] 2-{[2-(2-amino-ethylcarbamoyl)-1H-indol-5-yl]-amide}, 88

Compound 85 (prepared by the procedure described for the preparation of 35, 90 mg, 0.25 mmol) was dissolved in MeOH (50 mL) and ethyl acetate (25 mL) in a Parr flask and then 10% Pd—C (Degussa type, 50 mg) was added. The reaction was shaken at 50 psi for 45 mins and then the Pd—C filtered off. The solution was concentrated in vacuo to yield crude 86 which was used without further purification. The crude 86 was dissolved in DMF (3 mL) and added to 204 (100 mg, 0.2 mmol) and reacted at 55 C for 16 hours. The reaction product 87 was then precipitated by the addition of 45 mL ether. The crude 87 was suspended in anisole (400 mL) and trifluoroacetic acid (1.8 mL) was added. After 30 minutes at ambient temperature the product was precipitated by the addition of ether (45 mL). The precipitate was purified by reverse-phase HPLC and converted to the dihydrochloride salt by the addition of 2 ml 4 M HCl in dioxane to 4 ml of methanolic solution of the ditrifluoroacetate and precipitating twice with cold Et$_2$O. The precipitate was lyophilized to yield 20 mg (19%) of Compound 88.

MS: 224.59 ([M+2H$^+$]/2). $^1$H-NMR (DMSO-d$_6$) 12.01 (s, 1H), 11.64 (s, 1H), 10.26 (s, 1H), 8.78 (t, 1H), 8.63 (t, 1H), 8.29 (s, 1H), 8.09 (s, 1H), 7.96 (br s, 6H), 7.76 (d, 1H), 7.52–7.38 (m, 4H), 7.16 (s, 1H), 3.51 (m, 4H), 2.98 (m, 4H).

Example 81

Synthesis of 1H-Indole-2,5-dicarboxylic acid 5-[2-acetimidoylaminoethyl)amide] 2-{[2-(2-acetimidoylaminoethylcarbamoyl)-1H-indole-5-yl]amide}dihydrochloride, 89

A solution of 717 mg (5.80 mmol) ethyl acetamidate.HCl and 750 mg (5.80 mmol) DIEA in 5 ml DMF was added to a stirred solution of 193 mg (0.29 mmol) Compound 88 ditrifluoroacetate and 750 mg (5.80 mmol) DIEA at 0° C. The solution was stirred overnight while warming up to room temperature. The solvent and the excess amine were evaporated under reduced pressure, the residue was dissolved in MeOH and precipitated twice with cold Et$_2$O. The precipitate was purified by reverse-phase HPLC and converted to dihydrochloride salt by the addition of 2 ml 4 M HCl in dioxane to 4 ml of methanolic solution of the ditrifluoroacetate and precipitating twice with cold Et$_2$O. The precipitate was lyophilized to yield 48 mg (28%) of Compound 89. MS: 531.26 (M+H$^+$), $^1$H-NMR (DMSO-d$_6$): 12.06 (s, 1H), 11.70 (s, 1H), 10.32 (s, 1H), 9.69 (m, 2H), 9.22 (m, 2H), 8.87 (t, 1H), 8.76 (m, 3H), 8.33 (s, 1H), 8.16 (s, 1H), 7.81 (dd, 1H), 7.58 (d, 1H), 7.54 (m, 3H), 7.21 (s, 1H), 3.54 (m, 4H), 3.45 (m, 4H), 2.20 (s, 6H).

Example 82

Synthesis of 1H-Indole-2,5-dicarboxylic acid 5-{[2-(2,3-dimethylisothioureido)ethyl]amide} 2-({2-[2-(2,3-dimethylisothioureido)ethylcarbamoyl]-1H-indol-5-yl}amide)dihydrochloride, 90

To a solution of 300 mg (0.44 mmol) Compound 88 ditrifluoroacetate and 341 mg (2.64 mmol) DIEA in 5 ml DMF was added 97 mg (1.32 mmol) methyl isothiocyanate and the resulting solution was allowed to stand at room temperature for 3 days. The solvent and the excess amine were evaporated under reduced pressure, the residue was dissolved in 4 ml DMF and 4 ml MeI, and the solution was heated at 50° C. for 48 hr. The solvent and the excess MeI were evaporated under reduced pressure, the residue was dissolved in a minimum amount of MeOH and precipitated twice with cold ether. The precipitate was used as such in Examples 83 and 84. An analytical sample was purified by reverse-phase HPLC and converted to dihydrochloride salt by the addition of 1 ml 4 M HCl in dioxane to 2 ml of methanolic solution of the ditrifluoroacetate and precipitating twice with cold Et$_2$O. The precipitate was lyophilized for biological testing. Yield: 300 mg (98%). MS: 623.60 (M+H$^+$), $^1$H-NMR (DMSO-d$_6$): 1.2.05 (s, 1H), 11.70 (s, 1H), 10.30 (s, 1H), 9.53 (m, 1H), 9.33 (m, 1H), 9.01 (m, 1H), 8.89 (m, 1H), 8.76 (m, 1H), 8.29 (m, 1H), 8.16 (s, 1H), 7.80 (d, 1H), 7.54 (m, 3H), 7.45 (d, 1H), 7.18 (d, 1H), 3.60 (m, 8H), 3.00 (m, 6H), 2.71 (s, 3H), 2.64 (s, 3H).

Example 83

Synthesis of 1H-Indole-2,5-dicarboxylic acid 2-{[2-(N'-ethyl-N'-methylguanidino)ethyl]amide} 5-({2-[2-(N'-ethyl-N''-methylguanidino)ethylcarbamoyl]-1H-indol-5-yl}amide), dihydrochloride 91

To a solution of 150 mg (0.18 mmol) Compound 90 in 1 ml MeOH was added 1 ml 2M solution of EtNH$_2$ in MeOH. The solution was stirred and heated at 30° C. for 3 days. The volatiles were removed, the residue was dissolved in MeOH and precipitated twice with Et$_2$O. The precipitate was purified by reverse-phase HPLC and converted to dihydrochloride salt by the addition of 1 ml 4 M HCl in dioxane to 2 ml of methanolic solution of the ditrifluoroacetate and precipitating twice with cold Et$_2$O. The precipitate was lyophilized to yield 4.3 mg (3%) of Compound 91. MS: 617.38 (M+H$^+$), $^1$H-NMR (DMSO-d$_6$): 12.03 (s, 1H), 11.67 (s, 1H), 10.28 (s, 1H), 8.80 (t, 1H), 8.72 (t, 1H), 8.29 (s, 1H), 8.15 (s, 1H), 7.79 (dd, 1H), 7.53 (m, 4H), 7.17 (s, 1H), 3.46 (m, 8H, overlapping with water), 3.26 (m, 4H), 2.80 (d, 6H), 1.16 (td, 6H).

Example 84

Synthesis of 1H-Indole-2,5-dicarboxylic acid 2-({2-[N'-(2-hydroxyethyl)-N''-methylguanidino]ethyl}amide) 5-({2-(2-[N'-(2-hydroxyethyl)-N''-methylguanidino]ethylcarbamoyl)-1H-indol-5-yl}amide]dihydrochloride, 92

To a solution of 150 mg (0.18 mmol) Compound 90 in 2 ml MeOH was added 220 mg (3.6 mmol) ethanolamine. The solution was stirred and heated at 30° C. for 3 days. The volatiles were removed, the residue was dissolved in MeOH and precipitated twice with Et$_2$O. The precipitate was purified by reverse-phase HPLC and converted to dihydrochloride salt by the addition of 1 ml 4 M HCl in dioxane to 2 ml of methanolic solution of the ditrifluoroacetate and precipitating twice with cold Et$_2$O. The precipitate was lyophilized to yield 9 mg (7%) of Compound 92. MS: 649.36 (M+H$^+$), $^1$H-NMR (DMSO-d$_6$): 12.05 (s, 1H), 11.68 (s, 1H), 10.31 (s, 1H), 8.84 (t, 1H), 8.74 (t, 1H), 8.31 (s, 1H), 8.15 (s, 1H), 7.79 (dd, 1H), 7.57 (m, 4H), 7.19 (s, 1H), 3.56 (t, 4H) 3.49 (m, 6H, overlapping with water), 2.81 (d, 6H).

Example 85

Synthesis of N-(2-tert-Butoxycarbonylamino-ethyl)-terephthalamic acid, 94

1.8 g (10 mmol) terephthalic acid monomethyl ester (93 was heated with 8 mL ethylenediamine at 55 C° for 2.5 hr. The excess ethylenediamine was evaporated in vacuo, the residue was re-dissolved and re-evaporated twice in DMF to give 94 as white solid which was not soluble in DMF. It was suspended in 50 mL DMF, 2.37 g (11 mmol) Boc$_2$O was added and the suspension was vigorously stirred overnight at ambient temperature while it became a clear solution. The solvent was evaporated, the oily residue was dissolved in 100 mL 0.5 M NaOH solution, the insoluble material was filtered off and the clear filtrate was cooled to 0 C° and was acidified with 1 M HCl solution to pH 3 (about 45 mL HCl was necessary). The white precipitate was filtered off, washed 3 times with water and dried. Yield 2.5 g (81%) 94.

Example 86

Synthesis of (2-(4-[5-(2-Carbamimidoyl-ethylcarbamoyl)-1-cyclopropylmethyl-1H-pyrrol-3-ylcarbamoyl]-benzoylamino}-ethyl)-carbamic acid tert-butyl ester, 98

A solution of 185 mg (0.6 mmol) 94 in 1 mL DMF was activated to 95 by adding 114 µL (0.66 mmol) trifluoroacetic acid pentafluorophenyl ester followed by 114 µL (0.66 mmol) diisopropylethylamine and stirring at ambient temperature for 1 hr. To this solution 0.9 mmol 97 in 3 mL DMF (prepared from 238.5 mg of 96 as described in Dyatkina et al., J. Med. Chem., 45(4):805–817, 2002) was added and the mixture was heated overnight under argon at 55 C°. The solvent was evaporated; the oily residue was triturated with ether to give 98 in quantitative yield.

Example 87

Synthesis of N-(2-Amino-ethyl)-N'-[5-(2-carbamimidoyl-ethylcarbamoyl)-1-cyclopropylmethyl-1H-pyrrol-3-yl]-terephthalamide, 99

310 mg (0.55 mmol) 98 was dissolved in a mixture of 1 mL anisol and 4 mL trifluoroacetic acid and was agitated occasionally by swirling for 30 minutes at ambient temperature. 40 mL of cold ether was added, the precipitate was centrifuged, the ether phase was discarded, and the precipitate washed with ether (1×) then was re-precipitated from 5 mL methanol with 40 mL ether and dried to give 377 mg (96%) 99 as bis-TFA salt. MS: 220.61 (M+2H$^+$).

Example 88

Synthesis of N-[5-(2-Carbamimidoyl-ethylcarbamoyl)-1-cyclopropylmethyl-1H-pyrrol-3-yl]-N'-(2-guanidino-ethyl)-terephthalamide, 100

To a solution of 150 mg (0.23 mmol) 99 in 5 mL DMF 336.4 mg (2.3 mmol) pyrazole-1-carboxamidine hydrochloride and 396 µL (2.3 mmol) diisopropylethylamine was added. The solution was stirred overnight at ambient temperature. Next morning the solvent was evaporated, the oily residue was dissolved in 20 mL aqueous 0.1% TFA solution and was purified on a preparative reverse phase HPLC column using acetonitrile gradient. The fractions containing the pure product were pooled, evaporated to dryness dissolved in 3 mL methanol and treated with 1 mL 4.0M HCl in dioxane. 100 was precipitated with ether as bis-HCl salt, filtered off and dried to yield 62 mg (49%). MS: 241.70 (M+2H$^+$). $^1$H-NMR (DMSO d$_6$) 10.22 (s, 1H); 8.72 (s, 2H); 8.61 (t, 1H); 8.38 (s, 2H); 8.02 (t, 1H); 7.72 (s, 4H); 7.52 (t, 1H); 7.11 (d, 3H); 6.70 (d, 2H); 3.85 (d, 2H); 3.26–3.08 (m); 2.34 (m, 2H); 0.90 (m, 2H); 0.19–0.0 (m, 4H);

Example 89

Synthesis of [2-({2-[5-(3-Carbamimidoyl-propylcarbamoyl)-1-(3-methyl-butyl)-1H-pyrrol-3-ylcarbamoyl]-1H-indole-5-carbonyl}-amino)-ethyl]-carbamic acid tert-butyl ester, 101

1-(3-Methyl-butyl)-4-nitro-1H-pyrrole-2-carboxylic acid (3-carbamimidoyl-propyl)-amide (prepared by the methods described in Dyatkina et al. J. Med. Chem., 45:805–817, 2002) was reduced to its amine by hydrogenation according to the procedure for 97. The amine was then coupled with compound 33 according to the similar procedure for preparation of compound 95 to give compound 101 in 58% yield. MS: 609.33 (M+H$^+$).

Example 90

Synthesis of 1H-Indole-2,5-dicarboxylic acid 5-[(2-amino-ethyl)-amide] 2-{[5-(3-carbamimidoyl-propylcarbamoyl)-1-(3-methyl-butyl)-1H-pyrrol-3-yl]-amide}, 102

Compound 101 was treated with TFA/anisole according to the procedure for compound 99 to give compound 102 in quantitative yield. MS: 255.65 (M/2+H$^+$). $^1$H-NMR (DMSO-d$_6$) 11.94 (s, 1H), 10.51 (s, 1H), 9.03 (br s, 1H), 8.67–8.62 (m, 2H), 8.30 (s, 1H), 8.21 (t, 1H), 8.04 (br s, 2H), 7.78 (dd, 1H), 7.47 (d, 1H), 7.42 (s, 1H), 7.32 (d, 1H), 6.93 (d, 1H), 4.30 (t, 2H), 3.24–3.18 (m, 2H), 3.02–2.97 (m, 2H), 2.41 (t, 2H), 1.81 (dt, 2H), 1.58–1.47 (m, 3H), 1.29–1.24 (m, 2H), 0.89 (d, 6H).

Example 91

Synthesis of 1H-Indole-2,5-dicarboxylic acid 2-{[5-(3-carbamimidoyl-propylcarbamoyl)-1-(3-methyl-butyl)-1H-pyrrol-3-yl]-amide} 5-[(2-guanidino-ethyl)-amide], 103

Compound 103 was prepared from 101 with 1H-pyrazole-1-carboxamidine hydrochloride according to the procedure for compound 100. Yield: 62%. MS: 276.16 (M/2+H$^+$). $^1$H-NMR (DMSO-d$_6$) 11.93 (s, 1H), 10.50 (s, 1H), 9.02 (br s, 1H), 8.63–8.60 (m, 2H), 8.26 (s, 1H), 8.23 (t, 1H), 7.76–68 (m, 2H), 7.47 (d, 1H), 7.41 (s, 1H), 7.31 (d, 1H), 6.93 (d, 1H), 4.30 (t, 2H), 3.37–3.31 (m, 2H), 3.24–3.18 (m, 2H), 2.41 (t, 2H), 1.83 (dt, 2H), 1.58–1.47 (m, 3H), 1.29–1.24 (m, 2H), 0.89 (d, 6H).

Example 92

Synthesis of 5-Nitro-1H-indole-2-carboxylic acid, 104

Compound 1 (5 g, 21.3 mmol) was hydrolyzed in MeOH (360 ml) and 2 M aqueous NaOH (180 ml) according to the procedure for 32 to give a pale yellow powder (4.4 g, 100%). MS: 205.07 (M–H$^+$). $^1$H-NMR (DMSO d$_6$) 12.46 (s, 1H), 8.69 (d, 1H), 8.09 (d, 1H), 7.56 (d, 1H), 7.35 (s, 1H).

Example 93

Synthesis of 5-Nitro-1H-indole-2-carboxylate pentafluorophenyl ester, 105

Compound 105 was prepared from compound 104 with pentafluorophenyl trifluoroacetate according to the procedure for 3, and purified by chromatography (toluene-EtOAc 35:1). Yield: 57%.

Example 94

Synthesis of [2-({5-[(5-Nitro-1H-indole-2-carbonyl)-amino]-1H-indole-2-carbonyl}-amino)-ethyl]-carbamic acid tert-butyl ester, 106

Compound 106 was prepared from compound 86 and 105 in DMF in the presence of DIEA according to the procedure for 37. Yield: 83%.

Example 95

Synthesis of [2-({5-[(5-Amino-1H-indole-2-carbonyl)-amino]-1H-indole-2-carbonyl}-amino)-ethyl]-carbamic acid tert-butyl ester, 107

Compound 107 was prepared from compound 106 by hydrogenation according to the procedure for 36 in quantitative yield.

Example 96

Synthesis of 5-[(5-(N'-methyl-guanidine)-1H-indole-2-carbonyl)-amino]-1H-indole-2-carboxylic acid [2-(N'-methyl-guanidino)ethyl]-amide, 108

Compound 108 was prepared from compound 107, which was deprotected with TFA/anisole according to the procedure for compound 41, followed by guanidylation with 42 according to the general guanidylation methods—method A in Example 41.

Yield: 32%. MS: 245.11 (M/2+H$^+$). $^1$H-NMR (DMSO-d$_6$) 11.91 (s, 1H), 11.58 (s, 1H), 10.22 (s, 1H), 9.50 (s, 1H), 8.75 (br s, 1H), 8.06 (s, 1H), 7.65 (br s, 1H), 7.45–7.32 (m, 7H), 7.11 (s, 1H), 6.99 (d, 1H), 3.42 (s, 1H), 3.41–3.26 (m, 4H), 2.82 (s, 1H), 2.73 (br s, 3H).

Example 97

Synthesis of 5-Aminoacetylamino-1H-indole-2-carboxylic acid [2-carboxylic acid (2-aminoethyl)-amide-1H-indol-5-yl]-amide, 109

Compound 106 (0.25 g, 0.491 mmol) was reduced to its amine 107 by hydrogenation. A mixture of above amine 107, tert-butoxycarbonylaminoacetic acid (92.2 mg, 0.515 mmol), HBTU (0.195 g, 0.515 mmol), HOBt (79 mg, 0.515 mmol), and DIEA (94 µl, 0.54 mmol) in DMF (10 ml) was stirred at room temperature for 16 h. After evaporation of solvent, the residue was dissolved in MeOH (5 ml) and diluted with cold ether (50 ml). The precipitate was centrifuged and organic phase was poured out. This was repeated by using same amount of MeOH and ether. This product was treated with TFA/anisole according to the procedure for 41 to give its amine 109 in 95% yield. MS: 217.59 (M/2+H$^+$).

Example 98

Synthesis of 5-({5-[2-N'-Methyl-guanidino)-acetylamino]-1H-indole-2-carbonyl}-amino)-1H-indole-2-carboxylic acid [2-(N'-methyl-guanidino)ethyl]-amide, 110

Compound 109 was reacted with 42 according to the general guanidylation methods—method A in Example 41 to afford compound 110. Yield: 35%. MS: 273.63 (M/2+H$^+$). $^1$H-NMR (DMSO-d$_6$) 11.71 (s, 1H), 11.62 (s, 1H), 10.17 (s, 1H), 10.15 (s, 1H), 8.75 (br s, 1H), 8.10 (s, 1H), 8.02 (s, 1H), 7.71–7.29 (m, 7H), 7.15 (s, 1H), 4.06 (d, 2H), 3.42–3.28 (m, 4H), 2.77 (d, 3H), 2.73 (d, 3H).

Example 99

Synthesis of 5-[(5-Nitro-1H-indole-2-carbonyl)-amino]-1H-indole-2-carboxylic acid [2-(N'-methyl-guanidino)ethyl]-amide, 111

Compound 106 was treated with TFA/anisole according to the procedure for compound 41 and then reacted with 1H-pyrazole-1-carboxamidine hydrochloride according to the procedure for compound 47. Yield: 86%. MS: 449.15 (M+H$^+$). $^1$H-NMR (DMSO-d$_6$) 12.48 (s, 1H), 11.64 (s, 1H), 10.43 (s, 1H), 8.73–8.71 (m, 2H), 8.11–8.06 (m, 2H), 7.72–7.68 (m, 2H), 7.62–7.58 (d, 1H), 7.42–7.39 (m, 2H), 7.20–7.04 (m, 4H), 3.42 (t, 2H), 3.33–3.26 (m, 2H).

Example 100

Synthesis of 5-[(5-Amino-1H-indole-2-carbonyl)-amino]-1H-indole-2-carboxylic acid [2-(N'-methyl-guanidino)ethyl]-amide, 112

Compound 112 was obtained from compound 111 by hydrogenation according to procedure for compound 36. Yield: 95%. MS: 419.18 (M+H$^+$), 210.09 (M/2+H$^+$). $^1$H-NMR (DMSO-d$_6$) 12.06 (s, 1H), 11.62 (s, 1H), 10.30 (s, 1H), 10.20 (br s, 3H), 8.74 (t, 1H), 8.10 (s, 1H), 7.73–7.68 (m, 2H), 7.56–7.38 (m, 6H), 7.21–7.15 (m, 2H), 3.17 (br s, 4H).

Example 101

Synthesis of 5-Nitro-1H-indole-2-carboxylic acid [5-(2-carbamimidoyl-ethylcarbamoyl)-1-isobutyl-1H-pyrrol-3-yl]-amide, 113

1-Isobutyl-4-nitro-1H-pyrrole-2-carboxylic acid (2-carbamimidoyl-ethyl)amidine (Dyatkina et al. *J. Med. Chem.*, 45:805–817, 2002.) was reduced to its amine by hydrogenation according to the procedure for 36. The amine was directly reacted with 105 according to the procedure for 106 to give compound 113. Yield: 84%. $^1$H-NMR (DMSO-$d_6$): 12.35 (s, 1H), 10.62 (s, 1H), 8.95 & 8.55 (2 br. s, 3H), 8.73 (s, 1H), 8.30 (t, 1H), 8.07 (d, 1H), 7.59 (d, 1H), 7.56 (s, 1H), 7.30 (s, 1H), 6.96 (s, 1H), 4.11 (d, 2H), 3.50 (q, 2H), 2.62 (t, 2H), 1.98 (m, 1H), 0.81 (d, 6H).

Example 102

Synthesis of 5-(3-Amino-propionylamino)-1H-indole-2-carboxylic acid [5-(2-carbamimidoyl-ethylcarbamoyl)-1-isobutyl-1H-pyrrol-3-yl]-amide, 114

Compound 113 was reduced to its amine by hydrogenation according to the procedure for 36. The amine was then reacted with 3-tert-butoxycarbonylaminopropionic acid in the presence of HBTU, HOBt, and DIEA in dry DMF, followed by de-Boc protection according to the procedure for 109 to give 114 in quantitative yield. MS: 241.15 (M/2+H$^+$).

Example 103

Synthesis of 5-(3-Guanidino-propionylamino)-1H-indole-2-carboxylic acid [5-(2-carbamimidoyl-ethylcarbamoyl)-1-isobutyl-1H-pyrrol-3-yl]-amide, 115

Compound 114 was treated with 1H-pyrazole-1-carboxamidine hydrochloride according to the procedure for 47 to give compound 115. Yield: 26%. MS: 262.17 (M/2+H$^+$). $^1$H-NMR (DMSO-$d_6$): 11.51 (s, 1H), 10.25 (s, 1H), 9.93 (s, 1H), 8.89 & 8.60 (2br s, 3H), 8.25 (t, 1H), 7.99 (s, 1H), 7.51 (t, 1H), 7.37 (d, 1H), 7.26 (d, 1H), 7.25 (s, 1H), 7.19 (d, 1H), 6.92 (d, 1H), 4.11 (d, 2H), 2.59 (t, 2H), 1.98 (m, 1H), 0.80 (d, 6H).

Example 104

Synthesis of [2-({1Isobutyl-4-[(5-nitro-1H-indole-2-carbonyl)-amino]-1H-pyrrole-2-carbonyl}-amino)-ethyl]-carbamic acid tert-butyl ester, 116

Compound 21 was reduced by hydrogenation according to the procedure for compound 36, and then reacted with 105 according to the procedure for 106 to give compound 116. Yield: 82%. $^1$H NMR (DMSO-$d_6$): 12.30 (s, 1H), 10.58 (s, 1H), 8.74 (d, 1H), 8.08 (d, 1H), 8.05 (d, 1H), 7.59 (d, 1H), 7.54 (s, 1H), 7.28 (d, 1H), 6.88 (d, 1H), 4.11 (d, 2H), 3.20 (q, 2H), 3.06 (q, 2H), 1.37 (s, 9H), 0.80 (d, 6H).

Example 105

Synthesis of 5-(3-Amino-propionylamino)-1H-indole-2-carboxylic acid [5-(2-amino-ethylcarbamoyl)-1-isobutyl-1H-pyrrol-3-yl]-amide, 117

Compound 116 was reduced by hydrogenation according to the procedure for compound 36, and then reacted with 3-tert-butoxycarbonylaminopropionic acid in DMF in the presence of HBTU, HOBt, and DIEA, followed by deprotection with TFA/anisole according to the procedure for 108. Compound 117 was obtained in 96% yield. MS: 227.62 (M/2+H$^+$).

Example 106

Synthesis of 5-(3-Guanidino-propionylamino)-1H-indole-2-carboxylic acid [5-(2-guanidino-ethylcarbamoyl)-1-isobutyl-1H-pyrrol-3-yl]-amide, 118

Compound 118 was prepared from 117 with 1H-pyrazole-1-carboxamidine hydrochloride according to the procedure for 47 in 28% yield. MS: 269.68 (M/2+W). $^1$H NMR (DMSO-$d_6$): 11.52 (s, 1H), 10.25 (s, 1H), 9.93 (s, 1H), 8.15 (t, 1H), 7.99 (s, 1H), 7.48 (m, 2H), 7.37 (d, 1H), 7.26 (d, 1H), 7.19 (d, 1H), 6.94 (d, 1H), 4.11 (d, 2H) 3.28 (m, 6H), 2.59 (t, 2H), 1.98 (m, 1H), 0.80 (d, 6H).

Example 107

Synthesis of 1-Isobutyl-4-nitro-pyrrole-1H-2-carboxylic acid, 119

1-Isobutyl-4-nitro-1H-pyrrole-2-carboxylic acid ethyl ester was hydrolyzed with 2 N NaOH in MeOH according to the procedure for compound 32 to give compound 119. Yield: 93%.

Example 108

Synthesis of 1-Isobutyl-4-nitro-1H-pyrrole-2-carboxylate pentafluorophenyl ester, 120

Compound 120 was prepared from compound 119 with pentafluorophenyl trifluoroacetate according to the procedure for 33 and purified by chromatography eluted with toluene-EtOAc (60:1). Yield: 86%.

Example 109

Synthesis of (3-[(6-Nitro-1H-indole-2-carbonyl)-amino]-propyl)-carbamic acid tert-butyl ester, 121

Compound 121 was prepared from compound 34 with 1,3-diaminopropane, followed by Boc-protection according to the procedure for compound 35. Yield: 95%.

Example 110

Synthesis of [3-({6-[(1-Isobutyl-4-Nitro-pyrrole-2-carbonyl)-amino]-1H-indole-2-carbonyl}-amino)-propyl]-carbamic acid tert-butyl ester, 122

Compound 121 was reduced by hydrogenation according to the procedure for compound 36. The amine obtained was then reacted with 120 according to the procedure for compound 37. Yield: 89%.

Example 111

Synthesis of 4-(2-Aminopropionylamino)-1-isobutyl-pyrrol-2-carboxylic acid [2-carboxylic acid (2-aminopropyl)-amide-1H-indol-6-yl]-amide, 123

Compound 122 was reduced to its amine by hydrogenation according to the procedure for compound 36. The amine was then reacted with 3-tert-butoxycarbonylaminopropionic acid in DMF in the presence of HBTU, HOBt, and DIEA, followed by deprotection with TFA/anisole according to the procedure for 109. Compound 123 was obtained in 86% yield.

Example 112

Synthesis of 6-({4-[2-Guanidino-acetylamino]-1-isobutyl-pyrrole-2-carbonyl)-amino}-1H-indole-2-carboxylic acid (3-guanidinopropyl)-amide, 124

Compound 123 was reacted with 42 according to the general guanidylation methods—method A in Example 41 to afford compound 124. Yield: 48%. MS: 276.68 (M/2+H$^+$). $^1$H-NMR (DMSO-d$_6$) 11.51 (s, 1H), 10.16 (s, 1H), 9.85 (s, 1H), 8.57 (t, 1H), 7.98 (d, 1H), 7.77 (t, 1H), 7.63 (t, 1H), 7.48 (d, 1H), 7.28–7.23 (m, 2H), 7.08 (d, 1H), 7.93 (d, 1H), 4.11 (d, 2H), 3.40 (dd, 2H), 3.32 (dd, 2H), 3.19 (dd, 2H), 2.55 (t, 2H), 1.79 (dt, 1H), 1.76–1.72 (m, 2H), 0.78 (d, 6H).

Example 113

Synthesis of resin bound 4-hydroxy-benzamide, 125

2.5 g (2.55 mmol) MBHA resin (S=1.02) was swelled in DMF for 5 minutes. 1.06 g (7.65 mmol) 4-hydroxybenzoic acid and 1.03 g (7.65 mmol) HOBt was dissolved in DMF to which 1.18 mL (7.65 mmol) DIC was added. The clear mixture was poured to the resin and was agitated gently for 2 hrs. The completeness of the coupling reaction was checked with Kaiser test. The resin was drained, washed with DMF (5×). A mixture of 10 mL DMF and 5 mL ethanolamine was added and was agitated overnight at room temperature (18 hrs). Next morning the resin was drained, washed with DMF (3×), DCM (3×), 50% TFA/DCM (2×), DCM (2×), DMF (2×), DCM (2×), methanol (2×), ether (2×) and it was dried to get 2.8 g phenol resin, 125. The degree of substitution was S=0.89 mmol/g resin (calculated from the weight increase).

Example 114

Synthesis of resin bound 5-nitro-1H-indole-2-carboxylic acid, 126

1.0 g (5 mmol) 5-nitro-indole-2-carboxylic acid (104) was suspended in 20 mL DCM-DMF 1:1. 0.78 mL (5 mmol) DIC was added followed by 100 mg (0.8 mmol) DMAP. The suspension became clear within 5 minutes. The clear solution was added to the dry, 2.8 g (2.5 mmol) phenol resin, 125 and the mixture was agitated overnight (18 hrs) at room temperature. Next day the resin was drained, washed with DMF (3×). The un-reacted phenolic OH groups were blocked by acetylation with 20% acetic anhydride in DCM plus 0.5 mL DIEA. The resin was then washed with DMF (3×), DCM (3×), methanol (2×), ether (2×) and was dried resulting in 3.1 g 126. The degree of substitution was about 0.38 mmol/g resin—based on the weight increment.

Example 115

Synthesis of resin bound 5-amino-1H-indole-2-carboxylic acid, 127

0.4 g 126 (0.15 mmol) was swelled and washed twice with DMF. 1.8 g SnCl$_2$.2H$_2$O dissolved in 4 mL DMF was added to the drained resin which was agitated for 5 hrs at ambient temperature. The resin was then drained, washed with DMF, twice with DMF-H$_2$O 1:1, finally five times with DMF, drained and used immediately as described in Example 116

Example 116

Synthesis of resin bound 5-[(5-Nitro-benzofuran-2-carbonyl)-amino]-1H-indole-2-carboxylic acid, 129

To the solution of 93.2 mg (0.45 mmol) 5-nitrobenzofuran-2-carboxylic acid (128) in 6 mL DMF 209.0 mg (0.45 mmol) PyBroP and 157 μL (0.9 mmol) diisopropylethylamine was added and the clear solution was stirred for 10 minutes at room temperature. The activated acid was transferred to resin 127 which was agitated for 5 hrs. The resin was drained, washed twice with DMF. The analytical sample showed no complete reaction and therefore the activation/coupling reaction was repeated once again the same way using fresh reagents. The resin was drained, washed five times with DMF to give 129 which was used immediately as described in Example 117.

Example 117

Synthesis of resin bound 5-[(5-amino-benzofuran-2-carbonyl)-amino]-1H-indole-2-carboxylic acid, 130

Compound 129 was reduced as described for Compound 126 in Example 115, to give 130 which was used immediately as described in Example 118.

Example 118

Synthesis of resin bound 5-{[5-(2-Amino-acetylamino)-benzofuran-2-carbonyl]-amino}-1H-indole-2-carboxylic acid, 131

78.8 mg (0.45 mmol) Boc-Gly-OH in 4 mL DMF was pre-activated with 162 mg HBTU and 156 μL diisopropylethylamine for 2 minutes at room temperature. The activated amino acid was transferred to 130 which was agitated overnight at room temperature. Next day the resin was drained, washed four times with DMF, three times with DCM. The resin was treated twice with 6 mL of 25% TFA, 2% anisol in DCM for 2 minutes and 30 minutes, respectively, then it was washed three times with DCM, three times with DMF, three times with methanol, twice with ether and was dried overnight in high vacuum to give 0.51 g 131.

Example 119

Synthesis of resin bound 5-{[5-(2-guanidino-acetylamino)-benzofuran-2-carbonyl]-amino}-1H-indole-2-carboxylic acid, 132

170 mg (0.05 mmol) 131 was treated overnight with 73.5 mg (0.5 mmol) pyrazole-1-carboxamidine hydrochloride and 172 µL diisopropylethylamine dissolved in 2 mL DMF. Next day the resin was drained, washed five times with DMF to give 132 which was treated immediately to cleave the compound off, as described below in Example 121.

Example 120

Synthesis of 5-{[5-(2-amino-acetylamino)-benzofuran-2-carbonyl]-amino}-1H-indole-2-carboxylic acid (2-amino-ethyl)-amide, 133

To 340 mg (0.05 mmol) 131 resin 8 mL 1,2-ethylenediamine was added. The resin was agitated for 1 hr at ambient temperature then it was filtered off, washed twice with DMF. The filtrates were pooled and were evaporated to dryness. The remaining oily residue was dissolved in DMF and evaporated again in order to get rid of the amine traces. The crude material was dissolved in 5 mL aqueous 0.1% TFA solution and was purified on a preparative reverse phase HPLC column using acetonitrile gradient. The fractions containing the pure product were pooled, evaporated to dryness dissolved in 3 mL methanol and treated with 1 mL 4.0M HCl in dioxane. 133 was precipitated with ether as bis-HCl salt, filtered off and dried to yield 44.8 mg (88%). MS: 435.19 (M+H$^+$).

Example 121

Synthesis of 5-{[5-(2-guanidino-acetylamino)-benzofuran-2-carbonyl]-amino}-1H-indole-2-carboxylic acid (2-amino-ethyl)-amide, 134

132 (0.05 mmol) was treated with ethylenediamine as described for Compound 133 in Example 120. Yield: 19.9 mg (72%) of compound 134. MS: 477.22 (M+H$^+$).

Example 122

Synthesis of 5-{[5-(2-guanidino-acetylamino)-benzofuran-2-carbonyl]-amino}-1H-indole-2-carboxylic acid (2-guanidino-ethyl)-amide, 135

To a solution of 22.4 mg (0.044 mmol) 133 in 4 mL DMF 73.5 mg (0.5 mmol) pyrazole-1-carboxamidine hydrochloride and 172 µL diisopropylethylamine was added and the mixture was agitated overnight. Next morning the DMF was evaporated, the oily residue was dissolved in 5 mL aqueous 0.1% TFA solution and was purified on a preparative reverse phase HPLC column using acetonitrile gradient. The fractions containing the pure product were pooled, evaporated to dryness dissolved in 3 mL methanol and treated with 1 mL 4.0M HCl in dioxane. 135 was precipitated with ether as bis-HCl salt, filtered off and dried to yield 10.2 mg (32%). MS: 519.24 (M+H$^+$).

Example 123

Synthesis of 5-{[5-(2-amino-acetylamino)-1H-indole-2-carbonyl]-amino}-1H-indole-2-carboxylic acid (2-amino-ethyl)-amide, 136

Compound 136 was synthesized as described for Compound 133 in Example 116 through Example 120, except instead of 5-nitrobenzofuran-2-carboxylic acid 5-nitroindole-2-carboxylic acid was used. Yield: 24.6 mg (97%) of compound 136. MS: 434.20 (M+H$^+$).

Example 124

Synthesis of 5-{[5-(2-guanidino-acetylamino)-1H-indole-2-carbonyl]-amino}-1H-indole-2-carboxylic acid (2-amino-ethyl)-amide, 137

Compound 137 was synthesized as described for Compound 134 in Example 116 through Example 121, except instead of 5-nitrobenzofuran-2-carboxylic acid, 5-nitroindole-2-carboxylic acid was used. Yield: 44.2 mg (87%) of compound 137. MS: 476.22 (M+H$^+$).

Example 125

Synthesis of 5-{[5-(2-guanidino-acetylamino)-1H-indole-2-carbonyl]-amino}-1H-indole-2-carboxylic acid (2-guanidino-ethyl)-amide, 138

Compound 137 was synthesized as described for Compound 135 in Example 116 through Example 122, except instead of 5-nitrobenzofuran-2-carboxylic acid 5-nitroindole-2-carboxylic acid was used. Yield: 15.4 mg (59%) of compound 138. MS: 518.24 (M+H$^+$).

Example 126

Synthesis of 5-(2-Acetyloxyethylcarbamoyl)-1H-indole-2-carboxylic acid 150

To a solution of compound 30 in DMF, 1 eq. of ethanolamine is added and the solution is heated at 55° C. overnight. The volatiles are removed in vacuo and the residue is dissolved in a solution of MeOH and aq. 2M NaOH and heated at 65° C. overnight. MeOH is removed in vacuo, the mixture is diluted with water, cooled over ice, and brought to pH 3 with 5% HCl. The resulting precipitate is washed with H$_2$O and dried. The resulting powder is dissolved in DMF, treated with excess AcCl in the presence of excess Et$_3$N for 2 hr and poured into ice-water. The precipitate is filtered, and dried to give compound 150.

Example 127

Synthesis of 6-{[5-(2-Acetoxyethylcarbamoyl)-1H-indole-2-carbonyl]amino}-1H-indole-2-carboxylic acid methyl ester, 151

Compound 151 is synthesized as described for compound 39 in Example 33 except instead of compound 3, compound 150 is used.

Example 128

Synthesis of 1H-Indole-2,5-dicarboxylic acid 5-[(2-hydroxyethyl)amide] 2-{[2-(2-hydroxyethylcarbamoyl)-1H-indole-6-yl]amide}, 152

Compound 152 is synthesized as described for compound 40 in Example 34 except instead of compound 39, compound 151 and instead of ethylenediamine, ethanolamine is used.

Example 129

Synthesis of 1H-Indole-2,5-dicarboxylic acid 5-[(2-aminooxyethyl)amide] 2-{[2-(2-aminooxyethylcarbamoyl)-1H-indole-6-yl]amide}, 153

A suspension of compound 152 and a slight excess of N-hydroxyphthalimide in anhydrous THF is cooled to 0° C. under Ar. A slight excess of $Ph_3P$ and diethyl azodicarboxylate are added and the mixture is stirred at 0° C. for 2 hr. The mixture is concentrated, the product is purified by flash column chromatography and dissolved in a 1:1 mixture of EtOH and $NH_4OH$, stirred at room temperature overnight and filtered. The product is washed with $H_2O$ and dried to give 153.

Example 130

Synthesis of 1H-Indole-2,5-dicarboxylic acid 5-[(2-guanidinooxyethyl)amide] 2-{[2-(2-guanidinooxyethylcarbamoyl)-1H-indole-6-yl]amide}, 154

Compound 154 is synthesized as described for compound 47 in Example 42 except instead of compound 41, compound 153 is used.

Example 131

Synthesis of 1H-Indole-2,5-dicarboxylic acid 5-[(2-carbamimidoyloxyethyl)amide] 2-{[2-(2-carbamimidoyloxyethylcarbamoyl)-1H-indol-6-yl]amide}, 155

Compound 155 is synthesized as described for compound 47 in Example 42 except instead of compound 41 compound 152 is used.

Example 132

Synthesis of {2-[(6-Nitro-1H-indole-2-carbothioyl)amino]ethyl}carbamic acid tert-butyl ester, 156

To a suspension of 35 in toluene is added Lawesson's Reagent. The suspension is heated at reflux while stirring for 1 h. The reaction mixture is cooled over ice to precipitate the product. The product is then filtered, washed with hexane, and dried to give 156.

Example 133

Synthesis of 1H-Indole-2,5-dicarboxylic acid 5-[(2-amino-ethyl)-amide 2-{[2-(2-amino-ethylthiocarbamoyl)-1H-indol-6-yl]-amide}, 159

Compound 157 is synthesized as described for compound 36 in Example 31, except instead of 35, 156 is used.

Compound 158 is synthesized as described for compound 37 in Example 32, except instead of 36, 157 is used.

Compound 159 is synthesized as described for compound 41 in Example 35, except instead of 37, 158 is used.

Example 134

Synthesis of 1H-Indole-2,5-dicarboxylic acid 5-[(2-guanidino-ethyl)-amide 2-{[2-(2-guanidino-ethylthiocarbamoyl)-1H-indol-6-yl]-amide}, 160

Compound 160 is synthesized as described for compound 47 in example 42, except instead of 41, 159 is used.

Example 135

Synthesis of 1H-Indole-2,5-dicarboxylic acid 2-{[2-(4,5-dihydro-1H-imidazol-2-yl)-1H-indol-6-yl]-amide}-5-[(2-amino-ethyl)-amide], 165

To a solution of compound 156 in DMF is added methyl iodide. The reaction mixture is stirred overnight under Argon. DMF and methyl iodide are removed in vacuo and the product residue co-evaporated once with DMF to give 161. The product is used without additional purification.

Compound 161 is dissolved in a 4:1 solution of TFA and anisole and reacted at room temperature for 30 min. TFA and anisole are removed in vacuo and the residue co-evaporated 1× with DMF. The residue is then dissolved in DMF and reacted at 55° C. under Argon. DMF is removed in vacuo and the residue is taken up in MeOH (5 mL), precipitated with ether (45 mL), centrifuged, washed once with ether, and dried to give 162. The product is used without further purification.

Compound 163 is synthesized as described for compound 36 in Example 31, except instead of 35, 162 is used.

Compound 164 is synthesized as described for compound 37 in Example 32, except instead of 3, 163 is used.

Compound 165 is synthesized as described for compound 41 in Example 35, except instead of 37, 164 is used.

Example 136

Synthesis of 1H-Indole-2,5-dicarboxylic acid 2-{[2-(4,5-dihydro-1H-imidazol-2-yl)-1H-indol-6-yl]-amide}-5-[(2-guanidino-ethyl)-amide], 166

Compound 166 is synthesized as described for compound 47 in example 42, except instead of 4, 165 is used.

Example 137

Synthesis of 1H-Indole-2,5-dicarboxylic acid 5-[(2-(1-methylpyridiniu-2-yl)amino-ethyl)-amide] 2-{[2-(2-(1-methylpyridiniu-2-yl)amino-ethylcarbamoyl)-1H-indol-6-yl]-amide}, 170

Compound 170 was synthesized as described for Compound 47 in Example 42, except instead of 1H-pyrazole-1-carboxamidine, 2-chloro-1-methyl-pyridinium iodide was used. Yield: 32% of Compound 170. MS: 315.66 ([M+2H$^+$]/2). $^1$H-NMR (DMSO d$_6$) 12.10 (s, 1H), 11.69 (s, 1H), 10.41 (s, 1H), 8.99 (t, 1H), 8.85 (t, 1H), 8.56 (m, 2H), 8.27 (s, 1H), 8.21 (s, 1H), 8.19 (s, 1H), 8.10 (s, 1H), 7.99–7.94 (m, 2H), 7.76–7.73 (dd, 1H), 7.57–7.54 (m, 2H), 7.47–7.39 (m, 5H), 7.12 (d, 1H), 6.91 (t, 2H), 3.84–3.83 (d, 6H), 3.61 (m, 4H), 3.53 (m, 4H).

Example 138

Synthesis of 1H-Indole-2,5-dicarboxylic acid 5-[(2-guanidino-ethyl)-amide] 2-{[2-(guanidinomethyl-carbamoyl)-1H-indol-6-yl]-amide}, 171

6-Nitro-1H-indole-2-carboxylic acid 191

4.4 g (20 mmol) 6-Nitro-1H-indole-2-carboxylic acid methyl ester (190) was dissolved in 80 mL methanol and was treated with 30 mL 1M NaOH overnight at 55 C°. The methanol was evaporated, the remaining aqueous solution was diluted to 100 mL and was acidified to pH 2 using concentrated HCl. The precipitate was filtered off, washed three times with water then dried to give 3.92 g (95%) 191 as yellow powder. The NMR was consistent with the structure. 191 was used without further purification.

6-Nitro-1H-indole-2-carboxylic acid pentafluorophenyl ester 192

Compound 192 was synthesized as described for Compound 105 in Example 93, except instead of 104, 191 was used. It was used without isolation.

{[(6-Nitro-1H-indole-2-carbonyl)-amino]-methyl}-carbamic acid tert-butyl ester 194

To 3.0 mmol 192 in 5 mL DMF 548 mg (3.0 mmol) aminomethyl-carbamic acid tert-butyl ester hydrochloride was added and the mixture was stirred overnight at room temperature. The DMF was evaporated, the remaining oil was triturated first with ether then with water when it solidified. The solid material was filtered off, washed twice with water and was dried. Yield: 516 mg (52%). MS: 333.16 (M−H$^+$). $^1$H-NMR (DMSO d$_6$) 12.35 (s, 1H), 9.25 (s, 1H), 8.31 (s, 1H), 7.85 (d, 2H), 7.5–7.27 (m, 2H), 4.56 (s, 2H), 1.39 (s, 9H).

1H-Indole-2,5-dicarboxylic acid 5-[(2-guanidino-ethyl)-amide] 2-{[2-(guanidinomethyl-carbamoyl)-1H-indol-6-yl]-amide}, 171

Compound 171 was synthesized as described for Compound 47 in Examples 31, 32, 35 and 42 (Scheme 2, Scheme 3), except instead of 35 in Example 31, 194 was used. MS: 259.63 ([M+2H$^+$]/2). $^1$H-NMR (DMSO d$_6$) 12.06 (s, 1H), 11.75 (s, 1H), 10.40 (s, 1H), 9.66 (t, 1H), 8.65 (t, 1H), 8.30 (s, 1H), 8.13 (s, 1H), 7.78–7.73 (m, 2H), 7.62–7.58 (m, 2H), 7.49–7.44 (m, 2H), 7.21 (s, 1H), 4.66 (t, 2H), 3.42–3.33 (m, 4H, obscured by water).

Example 139

Synthesis of 1H-Indole-2,5-dicarboxylic acid 2-{[2-(2-guanidino-ethylcarbamoyl)-1H-indol-6-yl]-amide} 5-guanidinomethyl-amide, 172

5-[(tert-Butoxycarbonylamino-methyl)-carbamoyl]-1H-indole-2-carboxylic acid 196

To a solution of 1 g (2.5 mmol) 30 in 10 mL DMF 685 mg (3.75 mmol) aminomethyl-carbamic acid tert-butyl ester hydrochloride and 645 µL DIEA (3.75 mmol) was added and the mixture was stirred overnight. The DMF was evaporated and the resulting oil was triturated with water. The solid 195 was filtered off, washed twice with water and was saponified immediately with 3 mL 1 M NaOH in 25 mL methanol at room temperature overnight. The methanol was evaporated, the remaining aqueous solution was diluted to 100 mL and was acidified to pH 2 using concentrated HCl. The precipitate was filtered off, washed three times with water then dried to give 710 mg (85%) 196 as white powder. MS: 332.14 (M−H$^+$).

1H-Indole-2,5-dicarboxylic acid 2-{[2-(2-guanidino-ethylcarbamoyl)-1H-indol-6-yl]-amide} 5-guanidinomethyl-amide 172

Compound 172 was synthesized as described for Compound 47 in Examples 33, 34, 35 and 42 (Scheme 2, Scheme 3), except instead of 33 in Example 33, 196 was used. MS: 259.65 ([M+2H$^+$]/2). $^1$H-NMR (DMSO d$_6$) 12.10 (s, 1H), 11.65 (s, 1H), 10.35 (s, 1H), 9.55 (t, 1H), 8.66 (t, 1H), 8.33 (s, 1H), 8.28 (m, 1H), 8.08 (s, 1H), 7.78 (dd, 1H), 7.67 (m, 1H), 7.58 (m, 2H), 7.53–7.42 (m, 2H), 7.12 (s, 1H), 4.66 (t, 2H), 3.42–3.28 (m, 4H, obscured by water).

Example 140

Synthesis of 1H-Indole-2,5-dicarboxylic acid 5-guanidinomethyl-amide 2-{[2-(guanidinomethyl-carbamoyl)-1H-indol-6-yl]-amide}, 173

Compound 173 was synthesized as described for Compound 47 in Examples 31, 32, 35 and 42 (Scheme 2, Scheme 3), except instead of 35 in Example 31 and 33 in Example 32, 194 and activated (as described in Example 28 for 3) 196 were used, respectively. MS: 252.63 ([M+2H$^+$]/2). $^1$H-NMR (DMSO d$_6$) 12.11 (s, 1H), 10.38 (s, 1H), 9.56 (m, 2H), 8.33–8.28 (m, 3H), 8.12 (s, 1H), 7.8–7.77 (m, 1H), 7.59 (m, 2H), 7.55–7.43 (m, 2H), 7.19 (s, 1H), 4.66 (m, 4H).

Example 141

Synthesis of 1H-Indole-2,5-dicarboxylic acid 5-[(2-guanidino-ethyl)-amide] 2-{[2-(2-guanidino-ethyl-carbamoyl)-benzo[b]thiophen-5-yl]-amide}, 174

Compound 174 was synthesized as described for Compound 47 in Examples 33, 34, 35 and 42 (Scheme 2, Scheme 3), except instead of 34 in Example 33, 5-nitro-benzo[b]thiophene-2-carboxylic acid methyl ester (see D. L. Boger, B. E. Fink, M. P. Hedrick, *J. Am. Chem. Soc.*, 2000, 122, 6382–6394) was used. MS: 275.11 ([M+2H$^+$]/2). $^1$H-NMR (DMSO d$_6$) 12.11 (s, 1H), 10.59 (s, 1H), 9.03 (t, 1H), 8.65 (t, 1H), 8.47 (s, 1H), 8.30 (s, 1H), 8.16 (s, 1H), 8.00–7.61 (m, 4H), 7.50–7.47 (m, 1H), 3.3 (m, 8H, obscured by water).

Example 142

Synthesis of 1H-Indole-2,5-dicarboxylic acid 5-[(2-guanidino-ethyl)-amide] 2-{[2-(2-guanidino-ethyl-carbamoyl)-1H-benzoimidazol-5-yl]-amide), 175

Compound 175 was synthesized as described for Compound 47 in Example 33, 34, 35 and Example 42 (Scheme 2, Scheme 3), except instead of 34 in Example 33, 5-nitro-1H-benzoimidazole-2-carboxylic acid methyl ester (see D. L. Boger, B. E. Fink, M. P. Hedrick, *J. Am. Chem. Soc.*, 2000, 122, 6382–6394) was used. MS: 267.13 ([M+2H$^{30}$]/2). $^1$H-NMR (DMSO d$_6$) 12.15 (s, 1H), 10.65 (s, 1H), 9.15 (t, 1H), 8.70 (t, 1H), 8.34–8.32 (m, 2H), 7.86–7.76 (m, 4H), 7.68–7.63 (m, 1H), 7.49–7.46 (m, 1H), 3.40–3.30 (m, 8H, obscured by water).

Example 143

Synthesis of 1H-Indole-2,5-dicarboxylic acid 2-{[2-(2-guanidino-ethylcarbamoyl)-1H-indol-6-yl]-amide} 5-[(2-guanidino-ethyl)-methyl-amide], 176

N-Methyl-N'-trityl-ethane-1,2-diamine, 197

To a solution of 5 g (67.45 mmol) $N^1$-methyl-ethane-1,2-diamine in 50 mL DMF a solution of 16.72 g (60 mmol) trityl-chloride in 50 mL DMF was added slowly over a period of 10 minutes at room temperature. The mixture was stirred overnight then it was evaporated to dryness, the oil was dissolved in 100 mL ethylacetate, was washed three times with water, dried with sodium sulfate then was evaporated. The components of the oil were separated on a silicagel column using chloroform-methanol gradient elution to give 2.13 g (10%) 197.). $^1$H-NMR (CDCl$_3$) 7.48–7.44 (m, 6H), 7.27–7.21 (m, 6H), 7.18–7.12 (m, 3H), 3.44 (s, 1H), 2.78–2.74 (m, 2H), 2.42–2.38 (m, 5H).

5-{Methyl-[2-(trityl-amino)-ethyl]-carbamoyl}-1H-indole-2-carboxylic acid ethyl ester, 198

To a solution of 1 g (2.5 mmol) 30 in 3 mL DMF a solution of 0.89 g (2.8 mmol) 197 in 8 mL DMF was added, followed by 430 µL (2.5 mmol) DIEA. The mixture was heated at 55 C° under argon for 1 day. The DMF was evaporated, the oil was dissolved in 50 mL ether. The organic phase was washed twice with water, dried with sodium sulfate and was evaporated to give 198 as solid foam in quantitative yield. MS: 532.30 (M+H$^+$).

5-{Methyl-[2-(trityl-amino)-ethyl]-carbamoy}-1H-indole-2-carboxylic acid, 199

1.3 g (2.4 mmol) 198 was saponified with 5 mL 1M NaOH in 50 mL methanol at room temperature overnight. The methanol was evaporated, the solution was diluted to about 100 mL with cold icy water and was acidified to pH 2 using cold 1 M HCl. The product formed a gel which was extracted with 100 mL ethylacetate, the organic phase was washed once with water and twice with brine, was dried with sodium sulfate and was evaporated to dryness to give a brownish solid foam in quantitative yield. MS: 502.25 (M–H$^+$).

1H-Indole-2,5-dicarboxylic acid 2-{[2-(2-guanidino-ethylcarbamoyl)-1H-indol-6-yl]-amide} 5-[(2-guanidino-ethyl)-methyl-amide], 176

Compound 176 was synthesized as described for Compound 47 in Example 31, 32, 35 and Example 42 (Scheme 2, Scheme 3), except instead of 33 in Example 32, activated (as described in Example 28 for 3) 199 was used. MS: 273.63 ([M+2H$^+$]/2). $^1$H-NMR (DMSO d$_6$) 12. (s, 1H), 11.64 (s, 1H), 10.37 (s, 1H), 8.72 (t, 1H), 8.11 (s, 1H), 7.76 (t, 1H), 7.57–7.44 (m, 6H), 7.13 (s, 1H), 3.46–3.32 (m, 8H, obscured by water), 3.00 (s, 3H).

Example 144

Synthesis of Benzo[b]thiophene-2,5-dicarboxylic acid 5-[(2-guanidino-ethyl)-amide]2-{[2-(2-guanidino-ethylcarbamoyl)-benzo[b]thiophen-5-yl]-amide}, 177

Compound 177 was synthesized as described for Compound 47 in Examples 33, 34, 35 and 42 (Scheme 2, Scheme 3), except instead of 34 and 33 in Example 33, 5-nitro-benzo[b]thiophene-2-carboxylic acid methyl ester and 5-(2-tert-butoxycarbonylamino-ethylcarbamoyl)-benzo[b]thiophene-2-carboxylic acid pentafluorophenyl ester were used, respectively. MS: 283.61 ([M+2H$^+$]/2). $^1$H-NMR (DMSO d$_6$) 10.99 (s, 1H), 9.08 (t, 1H), 8.98 (t, 1H), 8.66 (s, 1H), 8.57 (d, 1H), 8.19 (s, 1H), 8.14 (d, 1H), 8.01–7.97 (m, 2H), 7.88–7.76 (m, 4H) 3.44–3.32 (m, 8H, obscured by water).

Example 145

Synthesis of 1H-Indole-2,5-dicarboxylic acid 5-[(2-guanidino-ethyl)-amide] 2-{[2-(2-guanidino-ethylcarbamoyl)-benzo[b]thiophen-6-yl]-amide}, 178

Compound 178 was synthesized as described for Compound 47 in Examples 33, 34, 35 and 42 (Scheme 2, Scheme 3), except instead of 34 in Example 33, 6-nitro-benzo[b]thiophene-2-carboxylic acid methyl ester was used. MS: 275.12 ([M+2H$^+$]/2). $^1$H-NMR (DMSO d$_6$) 12.15 (s, 1H), 10.72 (s, 1H), 9.04 (t, 1H), 8.68 (t, 1H), 8.60 (d, 1H), 8.32 (s, 1H), 8.13 (s, 1H), 7.92–7.83 (m, 2H), 7.80–7.75 (m, 5H), 7.66 (d, 1H), 7.49 (d, 1H), 3.42–3.36 (m, 8H, obscured by water).

Example 146

Synthesis of 1H-Indole-2,5-dicarboxylic acid 5-{[2-(N'-cyanoguanidino)ethyl]amide}-2-({2-[2-(N'-cyanoguanidino)ethylcarbamoyl]-1H-indol-6-yl}amide), 179

To a solution of 206 mg (0.46 mmol) compound 41 in 5 ml DMF, 238 mg (1.84 mmol) DIEA and 438 mg (1.84 mmol) diphenyl cyanocarbonimidate were added and the solution was allowed to stand at room temperature overnight. The next morning, the solvent was removed under reduced pressure, the residue was dissolved in a minimum amount of MeOH and precipitated with cold Et$_2$O. The mixture was centrifuged, the supernatant was decanted and the precipitation was repeated. The precipitate was dissolved in 5 ml 7M solution of NH$_3$ in MeOH and heated overnight at 60° C. in a glass vial with a teflon screw-cap. Then the solvent was removed under reduced pressure and purified by reverse-phase HPLC to give 25 mg 179. MS: 582.23 (M+H$^+$). $^1$H-NMR (DMSO-d$_6$) 11.96 (s, 1H), 11.59 (s, 1H), 10.27 (s, 1H), 8.48 (t, 2H), 8.23 (s, 1H), 8.47 (s, 1H), 7.74 (d, 1H), 7.57 (m, 2H), 7.45 (m, 2H), 7.07 (s, 1H), 6.83 (m, 4H), 6.74 (m, 4H).

Example 147

Synthesis of 6-Nitro-1H-indole-2-carboxylic acid{2-[(pyridine-2-carboximidoyl)amino]ethyl}amide, 200

To a solution of 144 g (0.58 mmol) of compound 35a in 2 ml DMF, 75 mg (0.58 mmol) DIEA and 171 mg (0.48 mmol) S-(2-naphthylmethyl)-2-pyridylthioimidate.HBr were added and the solution was heated at 55° C. for 3 days. Then the solvent was removed under reduced pressure and the residue was purified by reverse-phase HPLC to yield 35 mg of 200. MS: 353.09 (M+H$^+$).

Example 148

Synthesis of 1H-Indole-2,5-dicarboxylic acid 5-[(2-guanidinoethyl)amide] 2-[(2-{2-[(pyridine-2-carboximidoyl)amino]ethylcarbamoyl}-1H-indol-6-yl)amide], 180

Compound 180 was synthesized as described for compound 47 following Examples 31, 32, 35 and 42, except that 35 mg of compound 200 was used in place of compound 35 to yield 7.5 mg compound 180. MS: 297.65 (M+2H$^+$/2). $^1$H-NMR (DMSO-d$_6$) 12.02 (s, 1H), 11.65 (s, 1H), 10.33 (s, 1H), 10.14 (m, 1H), 9.81 (m, 1H), 9.51 (m, 1H), 8.82 (d, 1H), 8.77 (t, 1H), 8.61 (t, 1H), 8.27 (s, 1H), 8.24 (s, 1H), 8.16 (t, 1H), 8.08 (s, 1H), 7.81–7.75 (m, 2H), 7.60–7.42 (m, 4H), 7.10 (s, 1H), 3.72 (m, 2H), 3.65 (m, 2H), 3.42 (m, 2H), 3.39 (m obscured by H$_2$O, 2H).

Example 149

Synthesis of 1H-Indole-2,5-dicarboxylic acid 2-{[2-(3-carbamimidoylpropylcarbamoyl)-1H-indol-6-yl]amide} 5-[(2-guanidinoethyl)amide], 181

Compound 34 was hydrolyzed as described for compound 6, activated as described for compound 30 and 500 mg (1.34 mmol) of this activated ester was reacted with 225 mg (2.7 mmol) 4-aminobutyronitrile (see McKay, A. F.; Garmaise, D. L.; Gaudry, R.; Baker, H. A.; Paris, G. Y.; Kay, R. W.; Just, G. E.; Schwartz, R. *J. Am. Chem. Soc.* 1959, 81, 4328–4335) as described for compound 31 producing 300 mg (1.10 mmol) of the corresponding nitrile, which was treated with 3 ml saturated HCl/EtOH at room temperature overnight. The volatiles were removed under reduced pressure and the residue was treated with 6 ml 7N NH$_3$/MeOH overnight. The volatiles were again removed and the resulting amidine was converted to compound 181 as described for compound 47 following examples 31, 32, 35 and 42 and using this amidine in place of compound 35 to yield 75 mg compound 181. MS: 266.13 (M+2H$^+$/2). $^1$H-NMR (DMSO-d$_6$) 12.02 (s, 1H), 11.61 (s, 1H), 10.32 (s, 1H), 9.00 (s, 1H), 8.61 (m, 2H), 8.53 (s, 1H), 8.27 (s, 1H), 8.08 (s, 1H), 7.77 (d, 1H), 7.58 (d, 2H), 7.49 (d, 2H), 7.43 (d, 2H), 7.11 (s, 1H) 3.42 (m obscured by H$_2$O, 4H), 2.45 (m obscured by DMSO, 4H), 1.88 (p, 2H).

Example 150

Synthesis of 1H-Indole-2,5-dicarboxylic acid 5-[(2-guanidinoethyl)amide] 2-{[2-(2-methylaminoethylcarbamoyl)-1H-indol-6-yl]amide}, 182

Compound 182 was synthesized as described for compound 47 except N-methylethylenediamine was used in place of ethylenediamine in example 34. MS: 252.63 (M+2H$^+$/2).

Example 151

Synthesis of 1H-Indole-2,5-dicarboxylic acid 2-{[2-(2-dimethylaminoethylcarbamoyl)-1H-indol-6-yl]amide} 5-[(2-guanidinoethyl)amide], 183

Compound 183 was synthesized as described for compound 47, except N,N-dimethylethylenediamine was used in place of ethylenediamine in example 34. MS: 259.63 (M+2H$^+$/2).

Example 152

Synthesis of 1H-Indole-2,5-dicarboxylic acid 5-{[2-(guanidino)ethyl]amide} 2-({2-[2-(N'-cyanoguanidino)ethylcarbamoyl]-1H-indol-6-yl}amide), 184

Compound 184 was synthesized as described for compound 179 except compound 40 was used in place of compound 41 and examples 35 and 42 were employed before the purification step. MS: 279.13 (M+2H$^+$/2). $^1$H-NMR (DMSO-d$_6$) 12.01 (s, 1H), 11.60 (s, 1H), 10.30 (s, 1H), 8.59 (t, 1H), 8.52 (t, 2H), 8.26 (s, 1H), 8.06 (s, 1H), 7.76 (d, 1H), 7.59–7.56 (m, 2H), 7.49 (d, 1H), 7.42 (d, 1H), 7.07 (s, 1H).

FORMULATION EXAMPLES

The following are representative pharmaceutical formulations containing a compound of Formula (I).

Example 1

Tablet Formulation

The following ingredients are mixed intimately and pressed into single scored tablets.

| Ingredient | Quantity per tablet, mg |
| --- | --- |
| compound of this invention | 400 |
| cornstarch | 50 |
| croscarmellose sodium | 25 |
| lactose | 120 |
| magnesium stearate | 5 |

Example 2

Capsule Formulation

The following ingredients are mixed intimately and loaded into a hard-shell gelatin capsule.

| Ingredient | Quantity per capsule, mg |
| --- | --- |
| compound of this invention | 200 |
| lactose, spray-dried | 148 |
| magnesium stearate | 2 |

Example 3

Suspension Formulation

The following ingredients are mixed to form a suspension for oral administration.

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 ml |
| colorings | 0.5 mg |
| distilled water | q.s. to 100 ml |

Example 4

Injectable Formulation

The following ingredients are mixed to form an injectable formulation.

| Ingredient | Amount |
|---|---|
| compound of this invention | 0.2 mg–20 mg |
| sodium acetate buffer solution, 0.4 M | 2.0 ml |
| HCl (1N) or NaOH (1N) | q.s. to suitable pH |
| water (distilled, sterile) | q.s. to 20 ml |

Example 5

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| | |
|---|---|
| compound of the invention | 500 mg |
| Witepsol ® H-15 | balance |

BIOLOGICAL EXAMPLES

Example 1

Minimum Inhibitory Concentration (MIC) Assays

The assays described below were used to measure the minimum inhibitory concentration (MIC) of a compound necessary to inhibit visible growth of the organism tested. These assays are adapted from NCCLS protocols M7-A4 and M27-A (NCCLS vol 17:9 and vol 17:2) as modified by Sandven, S., *Clin. Micro.* (1999) 37:12, p. 3856–3859. MIC values for *Aspergillus* species were determined using NCCLS protocol M38-P.

Inoculum Preparation, Incubation and Reading Results

All compounds were dissolved in 100% DMSO to a stock concentration of 10 mM and used fresh stock compounds in powder form were kept frozen until needed and used freshly. When used for test purposes, compounds were diluted in the appropriate media depending on the organism being tested.

For yeast and *aspergillus* species, seven 1:2 serial dilutions of compound in appropriate media buffered with MOPS at pH 7.0 were prepared such that the final starting test compound concentrations were 44.4 µM for yeast and 50 µM *aspergillus* species. For bacteria, dilutions were made in growth media used for the particular bacteria being tested.

Yeast

Five well-separated colonies from a 24 h Sabouraud Dextrose plate incubated at 35° C. were picked and resuspended into 2 mL of normal saline. The O.D.$_{.530}$ was read and the culture was adjusted to 0.5 McFarland units with normal saline. A 1:2000 dilution was made with RPMI 1640 media buffered with MOPS at pH 7.0 and 100 µL of this inoculum preparation was added to an equal volume of test compound-containing media. 25 µL of the redox indicator Alamar Blue (Biosource International) was added to each well and the plates were incubated for 48 h at 35° C. Wells having yeast growth changed color from blue to pink. Accordingly, the MIC was calculated based on the well with the lowest concentration which did not change color from blue to pink, e.g., growth was inhibited.

Bacteria

Inoculums are made in the same manner as yeast except all dilutions are made in normal saline, with a final dilution of 1:200 and an inoculum of 10 µL. Solid and liquid media, as well as plate incubation times for the various organisms tested, are listed in Table 1 below.

TABLE 1

| Organism | Liquid Media | Solid Media | 96 Well Plate | Definition |
|---|---|---|---|---|
| VRE | BHI | BHIA | No vancomycin – 16 h | BHI—Brain Heart Infusion |
| *Moraxella catarrhalis* | BHI | BHIA | 16 h | BHI—Brain Heart Infusion |
| *Bacillus cereus* | CAMHB | BHIA | 16 h | BHI—Brain Heart Infusion |
| *Pseudemonas aeruginosa* | CAMHB | BHIA | 16 h | BHI—Brain Heart Infusion |
| *Staphylococcus aureus* | CAMHB | BHIA | 16 h | CAMHB—Cation adjusted Muller Hinton broth |
| *Haemophilus influenzae* | HTM | Chocolate Agar | 24 h | Chocolate Agar—Nutrient agar +5% heat lysed Sheep blood |
| *Streptococcus pneumoniae* | CAMHB + 5% LHB | MHA + 5% SB | 24 h | LHB—Lysed Horse Blood |
| *Aspergillus* | RPMI | SABDEX slants | 48 h | SABDEX—Sabouraud Dextrose Agar |

TABLE 1-continued

| Organism | Liquid Media | Solid Media | 96 Well Plate | Definition |
|---|---|---|---|---|
| Candida species | RPMI | SABDEX | 48 h | SABDEX—Sabouraud Dextrose Agar |

Compounds of this invention were tested in the assay described above and were found to have antibacterial activity. Compounds which have MIC of about 45.5 µM or less include compounds 10, 18, 19, 20, 21, 22, 23, 24, 25, 29, 41, 47, 48, 49, 50, 52, 53, 54, 55, 56, 57, 58, 59, 60, 61, 62, 63, 64, 66, 67, 68, 69, 72, 73, 74, 75, 76, 77, 80, 81, 82, 89, 90, 91, 92, 100, 103, 107, 108, 110, 115, 124, 171, 174, 180, and 181

Filamentous Fungi

Inoculums are made by incubating *Aspergillus* species for 7 days at 35° C. on potato dextrose agar slants. Slants are then covered with 1.0 mL of 0.85% saline, one drop of Tween 20 is added and colonies are teased with a sterile transfer loop to create a suspension which is allowed to sit for 5 min so heavier particles can drop out. The upper suspension is separated and adjusted to an optical density of 0.09 to 0.11. The resulting suspension is diluted 1:50, which yields 2× the final inoculum needed. Micro dilution trays are prepared as with yeast and incubated for 48 h at 35° C. For our purposes the MIC is defined as the lowest compound concentration at which 75% inhibition of growth is observed after 48 h.

Compounds of this invention were tested in the assay described above and were found to have antifungal activity. Compounds which have MIC of about 50 µM or less include compounds 9, 10, 18, 19, 20, 21, 22, 23, 24, 25, 47, 48, 49, 50, 52, 53, 54, 55, 56, 57, 58, 59, 60, 61, 62, 63, 64, 67, 68, 69, 70, 72, 73, 74, 75, 76, 77, 80, 81, 82, 89, 91, 92, 100, 103, 108, 110, 115, 135, 138, 170, 171, 172, 173, 174, 175, 176, 177, 178, 180, 181, 182, 183, and 184.

Example 2

Topoisomerase Inhibition Assays

*Candida albicans* topoisomerases I and II (cTop1 and cTop2) were isolated according to Fostel et al. (1992) and Shen et al. (1992). Human topoisomerases I and II (hTop1 and hTop2) were purchased from Topogen (Columbus, Ohio).

Inhibition of Topoisomerase I

Effects of GL compounds on DNA relaxation by topoisomerase I were studied using gel electrophoresis. Negatively supercoiled plasmid DNA (pARG, 8 kb) was used as the substrate. The reaction for *C. albicans* toposiomerase I was performed in 25 mM Tris HCl, pH 7.5, 50 mM NaCl, 2.5 mM MgCl2, 0.5 mM EDTA and 50 ug/mL BSA at 35° C. The reaction was stopped at any given time by adding SDS to a final concentration of 0.5%. Subsequently, proteinase K was added to 250 ug/mL and the mixture was incubated at 60° C. for 30 min. The reaction mixture was further extracted with phenol followed by phenol:isoamyl alcohol:chloroform (25:1:24). Samples were loaded on 0.8% agarose gel and subject to electrophoresis using 1×TBE. Different DNA intercalators were used for better gel resolution. Ethidium bromide was sometimes added to both the gel and the running buffer to 0.25 ug/mL. In other cases, chloroquine was added to 0.25 ug/mL to separate the DNA topoisomers.

Inhibition of Topoisomerase II

Effects of GL compounds on topoisomerase II were investigated by monitoring decatenation reactions using entangled kinetoplast DNA (Topogen). The decatenation reaction was performed in 10 mM Tris HCl, pH 7.5, 50 mM NaCl, 50 mM KCl, 5 mM $MgCl_2$, 0.1 mM EDTA and 0.5 mM ATP. The reaction was stopped at any given time by adding SDS to a final concentration of 1%. Subsequently, proteinase K was added to 250 ug/mL and the mixture was incubated at 60° C. for 30 min. The reaction mixture was further extracted with phenol followed by phenol:isoamyl alcohol:chloroform (25:1:24). Samples were loaded on 0.8% agarose gel and subject to electrophoresis using 1×TBE. Ethidium bromide was added to both the gel and the running buffer to 0.25 ug/mL.

Example 3

DNA Binding Properties of Compounds of this Invention

DNA Thermal Melting Studies

Interactions between DNA and compounds of this invention were investigated using thermal melting techniques. DNA interactions were monitored in a buffer containing 10 mM HEPES, pH 7.2, 0.1 mM EDTA, and 50 mM NaCl. DNA thermal melting was monitored by UV absorbance at 260 nm on a Cary 100 Bio UV/vis spectrophotometer. A 12 base-pair AT-rich DNA oligonucleotide (Oligo 1: CGAT-TATTAAGC) was used at 5 µM and mixed with compounds at various ratios. Temperature was typically varied from 15 to 95° C. with a ramp rate of 0.2° C./min. To determine the melting temperature (Tm) where half of the double-stranded DNA molecules dissociate into two separated strands, the first-order derivatives of the absorption-temperature curve were calculated using the Varian software, and the maximum of derivatives corresponds to the melting temperature. The melting temperature determined by the derivative methods were verified using a standard hyperchromicity method provided by the Varian software. The Tm value was reported as the difference between melting temperatures in the presence and in the absence of compounds.

Determination of Drug-DNA Binding Constants

An ethidium bromide displacement assay was used to determine the dissociation constant for binding of compounds to oligo 1. The assay was described in Dyatkina et al. *J. Med. Chem.*, 45:805–817, 2002.

Circular Dichroism Studies

Because of the electronic interactions between ligand and DNA, ligand binding can often induce circular dichroism ("CD") signals that are absent when DNA or ligand is alone in solution. DNA binding of compounds of this invention is determined using CD spectroscopy by methods well known in the art.

Example 4

In Vivo Properties

The in vivo properties of the compounds of the present invention are tested in animal models of infection. In animal model studies, the compound's effect on increasing the survival of infected animals, the compound's effect on infected organ systems, and other biological properties of the compounds are determined.

Effect on Survival

In a murine model of systemic aspergillosis, six-week-old female CD-1 mice (Charles River Laboratories) are infected with approximately 8.4×10⁶ conidia of a strain of *Aspergillus fumigatus* on day 0 by intravenous inoculation in a lateral tail vein. The infected mice are treated with compounds of this invention beginning on day 0, 1, 2, 3 or 4, and continue for between 2 to 30 or more additional days. The infected mice are treated once, twice, three times or four times a day. Alternatively, the infected mice are treated once every two, three, or four days. Groups of mice being treated receive various doses of compounds of this invention ranging from 0.1 to 50 mg per kg of body weight, for example, 1.0 mg/kg for one group, 3.3 mg/kg for the second group, and 10.0 mg/kg for the third group. Mice in control groups receive various doses of a known antifungal compound, for example, amphotericin B (AmB) at 0.8 mg/kg for one group, and AmB at 3.3 mg/kg for another group. A group of untreated mice serves as untreated controls. The compounds of this invention and the known antifungal compound are administered intraperatoneally (i.p.), intravenously (i.v.) intramuscularly (i.m,), intranasally, orally or subcutaneously, and are given once, twice, three times or four times daily for the duration of the experiment starting on day 0, 1, 2, 3 or 4.

Mortality is recorded through the course of infection, for example, through fourteen days of infection. Mortality is plotted on Kaplan-Meier plots and P-values are determined using well known statistical analysis methods, including the log rank test of comparative survival.

Effect on Infected Organ Systems

In the murine model of systemic aspergillosis described above, surviving mice are euthanized at pre-selected time points. The fungal burdens remaining in the organs, e.g., the brain and kidneys are determined by quantitative plating of organ homogenates on nutrient containing agar plates, for example, on potato dextrose agar plates. The plates are incubated for one to fourteen days. The colony forming units (CFU) recovered from the organ are determined to identify the effect of the compounds of this invention on the infected organ system. For example, a lower CFU value obtained from the brain of a treated animal when compared to the value obtained from the brain of a non-treated or control animal indicates a lower aspergillis brain burden from the treated animal. The results obtained are analyzed using statistical methods well known in the art. For example, the P values are determined by using the Mann-Whitney test of comparative CFU values obtained from treated, untreated, and treatment with AmB. Compounds of the present invention that lower the aspergillis brain burden are useful in treating central nervous system (CNS) fungal infections. These compounds may cross the blood-brain barrier.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed:

1. A compound of Formula (I):

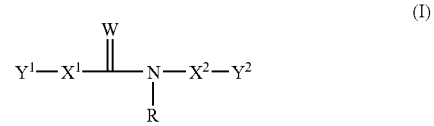

wherein:

$X^1$ and $X^2$ are independently arylene, substituted arylene, heteroarylene, or substituted heteroarylene provided that $X^1$ and $X^2$ are not both pyrrolene;

$Y^1$ is

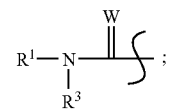

$Y^2$ is

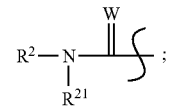

W is O or S;

R is hydrogen or $C_1$–$C_6$ alkyl;

$R^1$, $R^2$, $R^5$ and $R^{22}$ are independently

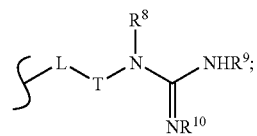

L is selected from the group consisting of a bond, $C_1$–$C_6$ alkylene, and cycloalkylene;

T is a bond such that when both T is a bond and L is a bond, T and L together is a bond;

$R^3$ and $R^{21}$ are independently hydrogen or $C_1$–$C_6$ alkyl;

$R^8$ is hydrogen or alkyl;

$R^9$ and $R^{10}$ are independently hydrogen, hydroxyl, alkyl, substituted alkyl, alkenyl, substituted alkenyl, cycloalkyl, cycloalkenyl or heterocyclic, or $R^9$ and $R^{10}$ together with the atoms to which they are attached form a heterocyclic or heteroaryl ring, or $R^{11}$ and $R^{12}$ together with the atoms to which they are attached form a heterocyclic or heteroaryl ring;

or an acid addition salt thereof;

with the proviso that the compound of Formula (I) is not one of the following compounds:

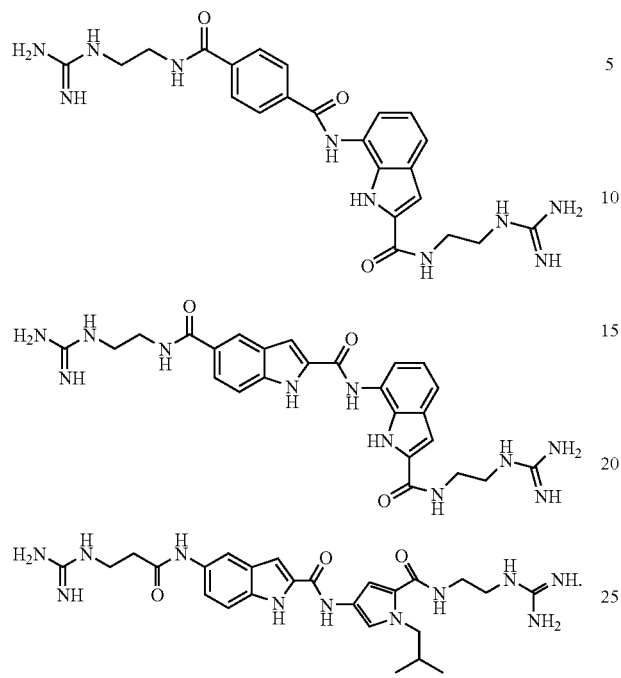

2. The compound of claim 1 wherein $X^1$ and $X^2$ are independently selected from a group consisting of the following moieties:

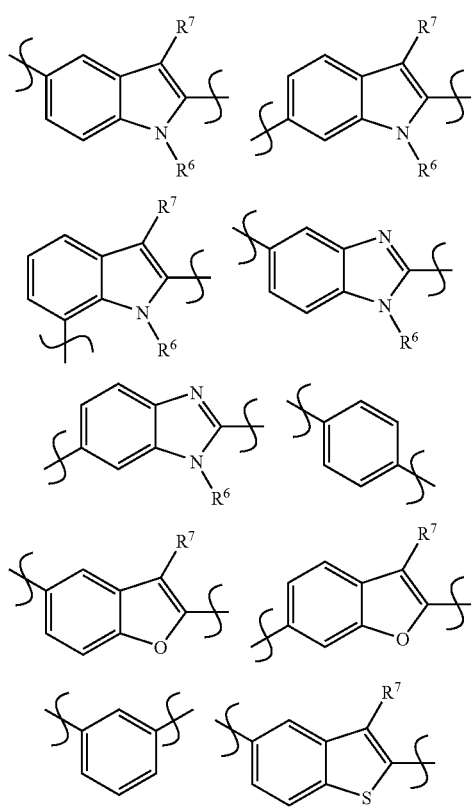

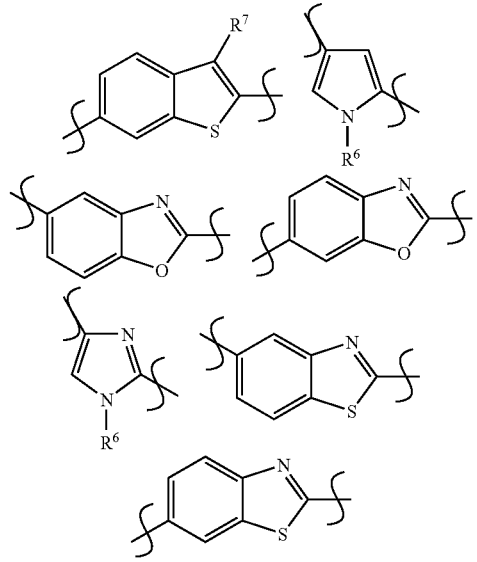

wherein
  $R^6$ is hydrogen, alkyl or substituted alkyl; and
  $R^7$ is hydrogen, halo, alkyl, substituted alkyl, aryl, substituted aryl, heteroaryl, substituted heteroaryl, sulfonyl, hydroxyl, alkoxy or acyl.

3. The compound of claim 2 wherein W is O.

4. The compound of claim 3, wherein at least one of $X^1$ and $X^2$ is selected from the group consisting of the following moieties:

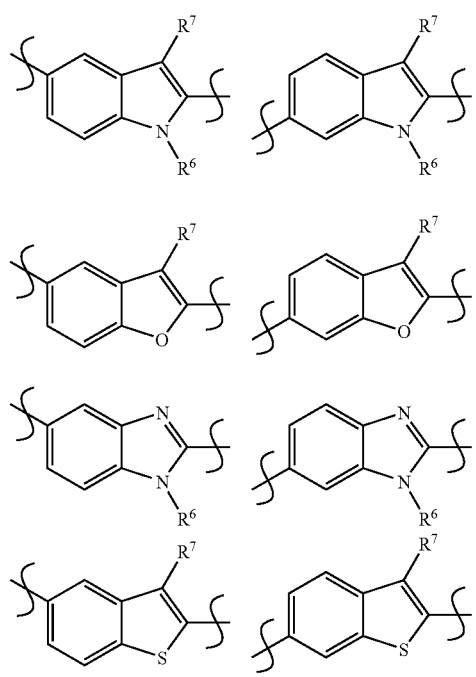

wherein
  $R^6$ is hydrogen, alkyl or substituted alkyl; and
  $R^7$ is hydrogen, halo, alkyl, substituted alkyl, aryl, substituted aryl, heteroaryl, substituted heteroaryl, sulfonyl, hydroxyl, alkoxy or acyl.

5. The compound of claim 4, wherein $R^1$ and $R^2$ are independently selected from the group consisting of the following moieties:

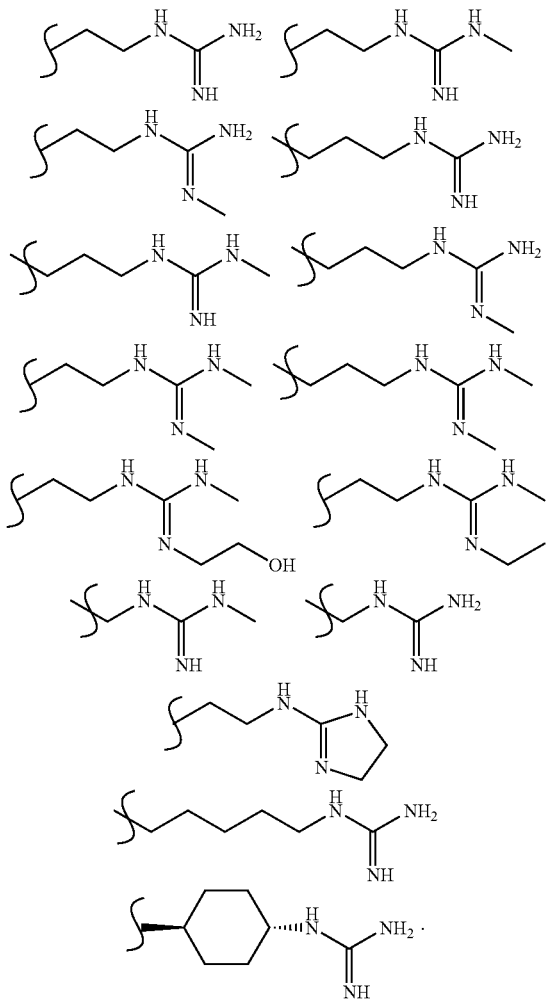

6. The compound of claim 5, wherein at least one of $X^1$ and $X^2$ is selected from the group consisting of:

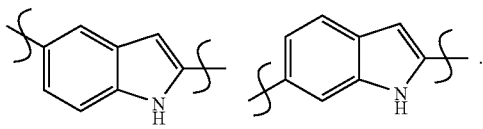

7. A compound selected from a group consisting of:

1H-Indole-2,5-dicarboxylic acid 2-[(2-guanidino-ethyl)-amide] 5-{[2-(2-guanidino-ethyl-carbamoyl)-1H-indol-5-yl]-amide}, 10;

1H-Indole-2,5-dicarboxylic acid 2-[(4-guanidinomethyl-cyclohexylmethyl)-amide] 5-({2-[(4-guanidinomethyl-cyclohexylmethyl)-carbamoyl}-1H-indol-5-yl}-amide), 18;

1H-Indole-2,5-dicarboxylic acid 2-[(5-guanidino-pentyl)-amide] 5-{[2-(5-guanidino-pentylcarbamoyl)-1H-indol-5-yl]-amide}, 20;

1H-Indole-2,5-dicarboxylic acid 2-[(4-guanidino-cyclohexyl)-amide] 5-{[2-(4-guanidino-cyclohexylcarbamoyl)-1H-indol-5-yl]-amide}, 21;

1H-Indole-2,5-dicarboxylic acid 2-(4-guanidinomethyl-benzylamide) 5-{[2-(4-guanidinomethyl-benzylcarbamoyl)-1H-indol-5-yl]-amide}, 22;

1H-Indole-2,5-dicarboxylic acid 2-[(2-guanidinoethyl)-amide] 5-{[5-(2-guanidino-ethylcarbamoyl)-1-isobutyl-1H-pyrrol-3-yl]-amide}, 29;

1H-Indole-2,5-dicarboxylic acid 5-[(2-guanidino-ethyl)-amide] 2-{[2-(2-guanidino-ethylcarbamoyl)-1H-indol-6-yl]-amide}, 47;

1H-Indole-2,5-dicarboxylic acid 5-{[2-(N'-methyl-guanidino)-ethyl]-amide} 2-({2-[2-(N'-methyl-guanidino)-ethylcarbamoyl]-1H-indol-6-yl}-amide), 48;

1H-Indole-2,5-dicarboxylic acid 2-{[2-(N',N''-dimethylguanidino)ethyl]amide} 5-({2-[2-(N',N''-dimethylguanidino)ethylcarbamoyl]-1H-indol-6-yl}amide)dihydrochloride, 49;

1H-Indole-2,5-dicarboxylic acid 5-{[2-(4,5-dihydro-1H-imidazol-2-ylamino)-ethyl]amide} 2-({2-[2-(4,5-dihydro-1H-imidazol-2-ylamino)-ethylcarbamoyl]-1H-indol-6-yl}-amide), 50;

1H-Indole-2,5-dicarboxylic acid 2-{[2-(2-guanidinoethylcarbamoyl)-1H-indol-6-yl]amide} 5-[(3-guanidinopropyl)amide]dihydrochloride, 52;

1H-Indole-2,5-dicarboxylic acid 2-({2-[2-(N'-methylguanidino)ethylcarbamoyl]-1H-indole-6-yl}amide) 5-{[3-(N'-methylguanidino)propyl]amide}dihydrochloride, 53;

1H-Indole-2,5-dicarboxylic acid 2-({2-[2-(N',N''-dimethylguanidino)ethylcarbamoyl]-1H-indole-6-yl}amide) 5-{[3-(N',N''-dimethylguanidino)propyl]amide}dihydrochloride, 54;

1H-Indole-2,5-dicarboxylic acid 5-{[2-(2-(N'-methylguanidino)ethyl]amide} 2-({2-[2-(N'-methylguanidino)ethylcarbamoyl]-1H-indole-5-yl}amide)dihydrochloride, 55;

1H-Indole-2,5-dicarboxylic acid 2-{[2-(N',N''-dimethylguanidino)ethyl]amide} 5-({2-[2-(N',N''-dimethylguanidino)ethylcarbamoyl]-1H-indole-5-yl}amide), 56;

1H-Indole-2,5-dicarboxylic acid 5-{[2-(4,5-dihydro-1H-imidazol-2-ylamino)ethyl]amide} 2-({2-[2-(4,5-dihydro-1H-imidazol-2-ylamino)ethylcarbamoyl]-1H-indole-5-yl}amide)dihydrochloride, 57;

1H-Indole-2,5-dicarboxylic acid 2-{[2-(2-guanidinoethylcarbamoyl)-1H-indol-5-yl]amide} 5-[(3-guanidinopropyl)amide]dihydrochloride, 58;

1H-Indole-2,5-dicarboxylic acid 2-({2-[2-(N'methylguanidino)ethylcarbamoyl]-1H-indol-5-yl)amide) 5-{[3-(N'methylguanidino)propyl]amide}hydrochloride, 59;

1H-Indole-2,5-dicarboxylic acid 2-({2-[2-(N',N''-dimethylguanidino)ethylcarbamoyl]-1H-indol-5-yl)amide) 5-{[3-(N',N''-dimethylguanidino)-propyl]amide}hydrochloride, 60;

1H-Indole-2,5-dicarboxylic acid 2-{[2-(2-carbamimidoylethylcarbamoyl)-1H-indol-5-yl]amide} 5-[(2-guanidinoethyl)amide]dihydrochloride, 61;

1H-Indole-2,5-dicarboxylic acid 5-[(2-guanidino-ethyl)-amide] 2-{[2-(3-guanidino-propylcarbamoyl)-1H-indol-6-yl]-amide}, 62;

1H-Indole-2,5-dicarboxylic acid 5-{[2-(N'-methyl-guanidino)-ethyl]-amide} 2-({2-[3-(N'-methyl-guanidino)-propylcarbamoyl]-1H-indol-6-yl}-amide), 63;

1H-Indole-2,5-dicarboxylic acid 2-{[2-(N',N"-dimethyl-guanidino)-ethyl]-amide} 5-({2-[3-(N',N"-dimethyl-guanidino)-propylcarbamoyl]-1H-indol-6-yl}-amide)), 64;

1H-Indole-2,5-dicarboxylic acid 5-[(2-guanidino-ethyl)-amide] 2-{[2-(3-guanidino-propylcarbamoyl)-1H-indol-5-yl]-amide}, 67;

1H-Indole-2,5-dicarboxylic acid 5-{[2-(N'-methyl-guanidino)-ethyl]-amide} 2-({2-[3-(N'-methyl-guanidino)-propylcarbamoyl]-1H-indol-5-yl}-amide), 68;

1H-Indole-2,5-dicarboxylic acid 2-{[2-(N',N"-dimethyl-guanidino)-ethyl]-amide} 5-({2-[3-(N',N"-dimethyl-guanidino)-propylcarbamoyl]-1H-indol-5-yl}-amide), 69;

N-(2-Guanidino-ethyl)-N'-[2-(2-guanidino-ethylcarbamoyl)-1H-indol-5-yl]-terephthalamide, 70;

1H-Indole-2,5-dicarboxylic acid 5-[(3-guanidino-propyl)-amide] 2-{[2-(3-guanidino-propylcarbamoyl)-1H-indol-6-yl-]-amide}, 72;

1H-Indole-2,5-dicarboxylic acid 5-[(3-(N'-methyl-guanidino)-propyl)-amide] 2-{[2-(3-(N'-methyl-guanidino)-propylcarbamoyl)-1H-indol-6-yl-]-amide}, 73;

1H-Indole-2,5-dicarboxylic acid 5-[(3-(N',N"-dimethyl-guanidino)-propyl)-amide] 2-{[2-(3-(N',N"-dimethyl-guanidino)-propylcarbamoyl)-1H-indol-6-yl-]-amide}, 74;

1H-Indole-2,5-dicarboxylic acid 5-[(3-guanidino-propyl)-amide] 2-{[2-(3-guanidino-propylcarbamoyl)-1H-indol-5-yl-]-amide}, 75;

1H-Indole-2,5-dicarboxylic acid 5-[(3-(N'-methyl-guanidino)-propyl)-amide] 2-{[2-(3-(N'-methyl-guanidino)-propylcarbamoyl)-1H-indol-5-yl-]-amide}, 76;

1H-Indole-2,5-dicarboxylic acid 5-[(3-(N',N"-dimethyl-guanidino)-propyl)-amide] 2-{[2-(3-(N',N"-dimethyl-guanidino)-propylcarbamoyl)-1H-indol-5-yl-]-amide}, 77;

1H-Indole-2,5-dicarboxylic acid 5-[(2-guanidino-ethyl)-amide] 2-{[5-(2-guanidino-ethylcarbamoyl)-1-isobutyl-1H-pyrrol-3-yl]-amide}, 80;

1H-Indole-2,5-dicarboxylic acid 2-({1-isobutyl-5-[2-(N'-methyl-guanidino)-ethylcarbamoyl]-1H-pyrrol-3-yl}-amide) 5-{[2-(N'-methyl-guanidino)-ethyl]-amide}, 81;

1H-Indole-2,5-dicarboxylic acid 5-[(2-guanidino-ethyl)-amide] 2-{[2-(2-guanidino-ethylcarbamoyl)-1H-indol-5-yl]-amide}, 82;

1H-Indole-2,5-dicarboxylic acid 2-{[2-(N'-ethyl-N"-methylguanidino)ethyl]amide} 5-({2-[2-(N'-ethyl-N"-methylguanidino)ethylcarbamoyl]-1H-indol-5-yl}amide), dihydrochloride, 91;

N-[5-(2-Carbamimidoyl-ethylcarbamoyl)-1-cyclopropylmethyl-1H-pyrrol-3-yl]-N'-(2-guanidino-ethyl)-terephthalamide, 100;

1H-Indole-2,5-dicarboxylic acid 2-{[5-(3-carbamimidoyl-propylcarbamoyl)-1-(3-methyl-butyl)-1H-pyrrol-3-yl]-amide} 5-[(2-guanidino-ethyl)-amide], 103;

5-[(5-(N'-methyl-guanidine)-1H-indole-2-carbonyl)-amino]-1H-indole-2-carboxylic acid [2-(N'-methyl-guanidino)ethyl]-amide, 108;

5-({5-[2-(N'-Methyl-guanidino)-acetylamino]-1H-indole-2-carbonyl}-amino)-1H-indole-2-carboxylic acid [2-(N'-methyl-guanidino)ethyl]-amide, 110;

6-({4-[2-Guanidino-acetylamino]-1-isobutyl-pyrrole-2-carbonyl}-amino)-1H-indole-2-carboxylic acid (3-guanidinopropyl)-amide, 124;

5-{[5-(2-guanidino-acetylamino)-benzofuran-2-carbonyl]-amino}-1H-indole-2-carboxylic acid (2-guanidino-ethyl)-amide, 135;

5-{[5-(2-guanidino-acetylamino)-1H-indole-2-carbonyl]-amino}-1H-indole-2-carboxylic acid (2-guanidino-ethyl)-amide, 138;

1H-Indole-2,5-dicarboxylic acid 5-[(2-guanidinooxyethyl)amide] 2-{[2-(2-guanidinooxyethylcarbamoyl)-1H-indole-6-yl]amide}, 154;

1H-Indole-2,5-dicarboxylic acid 5-[(2-guanidino-ethyl)-amide] 2-{[2-(2-guanidino-ethylthiocarbamoyl)-1H-indol-6-yl]-amide}, 160;

1H-Indole-2,5-dicarboxylic acid 5-[(2-guanidino-ethyl)-amide] 2-{[2-(guanidinomethyl-carbamoyl)-1H-indol-6-yl]-amide}, 171;

1H-Indole-2,5-dicarboxylic acid 2-{[2-(2-guanidino-ethylcarbamoyl)-1H-indol-6-yl]-amide} 5-guanidinomethyl-amide, 172;

1H-Indole-2,5-dicarboxylic acid 5-guanidinomethyl-amide 2-{[2-(guanidinomethyl-carbamoyl)-1H-indol-6-yl]-amide}, 173;

1H-Indole-2,5-dicarboxylic acid 5-[(2-guanidino-ethyl)-amide] 2-{[2-(2-guanidino-ethylcarbamoyl)-benzo[b]thiophen-5-yl]-amide}, 174;

1H-Indole-2,5-dicarboxylic acid 5-[(2-guanidino-ethyl)-amide] 2-{[2-(2-guanidino-ethylcarbamoyl)-1H-benzoimidazol-5-yl]-amide}, 175;

1H-Indole-2,5-dicarboxylic acid 2-{[2-(2-guanidino-ethylcarbamoyl)-1H-indol-6-yl]-amide} 5-[(2-guanidino-ethyl)-methyl-amide], 176;

Benzo[b]thiophene-2,5-dicarboxylic acid 5-[(2-guanidino-ethyl)-amide] 2-{[2-(2-guanidino-ethylcarbamoyl)-benzo[b]thiophen-5-yl]-amide}, 177;

1H-Indole-2,5-dicarboxylic acid 5-[(2-guanidino-ethyl)-amide] 2-{[2-(2-guanidinoethyl-carbamoyl)-benzo[b]thiophen-6-yl]-amide}, 178;

1H-Indole-2,5-dicarboxylic acid 2-{[2-(3-carbamimidoylpropyl-carbamoyl)-1H-indol-6-yl]amide} 5-[(2-guanidinoethyl)amide], 181;

or an acid addition salt thereof.

8. A pharmaceutical composition comprising a pharmaceutically acceptable diluent and a therapeutically effective amount of a compound or mixture of any one of the compounds of claims 1–6 and 7.

9. A method for treating bacterial or fungal infections, wherein the method comprises administration of a therapeutically effective amount of a compound or mixture of any one of the compounds of claims 1–6 and 7.

* * * * *